US010688063B2

(12) United States Patent
Farese et al.

(10) Patent No.: US 10,688,063 B2
(45) Date of Patent: *Jun. 23, 2020

(54) TREATING AND/OR PREVENTING INSULIN-RESISTANCE RELATED WEIGHT GAIN

(71) Applicant: University of South Florida, Tampa, FL (US)

(72) Inventors: Robert Vito Farese, St. Petersburg, FL (US); Mini Paliyath Sajan, Wesley Chapel, FL (US)

(73) Assignees: University of South Florida, Tampa, FL (US); The United States Government as Represented by the Department of Veterans Affairs of General Counsel- PSG IV (024), Washington, DC (US)

( * ) Notice: Subject to any disclaimer, the term of this patent is extended or adjusted under 35 U.S.C. 154(b) by 463 days.

This patent is subject to a terminal disclaimer.

(21) Appl. No.: 15/730,423

(22) Filed: Oct. 11, 2017

(65) Prior Publication Data

US 2018/0028488 A1 Feb. 1, 2018

Related U.S. Application Data

(62) Division of application No. 14/907,840, filed as application No. PCT/US2014/048910 on Jul. 30, 2014, now Pat. No. 9,795,584.

(60) Provisional application No. 61/859,875, filed on Jul. 30, 2013.

(51) Int. Cl.
| | |
|---|---|
| *A61K 31/122* | (2006.01) |
| *A61P 3/04* | (2006.01) |
| *A61P 3/10* | (2006.01) |
| *A61K 31/341* | (2006.01) |

(52) U.S. Cl.
CPC .......... *A61K 31/122* (2013.01); *A61K 31/341* (2013.01); *A61P 3/04* (2018.01); *A61P 3/10* (2018.01)

(58) Field of Classification Search
CPC ............. A61K 31/122; A61P 3/04; A61P 3/10
See application file for complete search history.

(56) References Cited

U.S. PATENT DOCUMENTS

| | | | |
|---|---|---|---|
| 5,468,766 A | 11/1995 | Eberlein et al. | |
| 5,648,381 A | 7/1997 | Cugnon De Sevricourt et al. | |
| 8,580,769 B2 | 11/2013 | Farese | |
| 2003/0195238 A1 | 10/2003 | Gil et al. | |
| 2006/0185026 A1 | 8/2006 | Sacktor et al. | |
| 2009/0042956 A1 | 2/2009 | Bozik et al. | |
| 2009/0233995 A1 | 9/2009 | Lautt | |
| 2010/0137449 A1 | 6/2010 | Tripp et al. | |
| 2011/0229484 A1 | 9/2011 | Baumert et al. | |
| 2012/0302561 A1 | 11/2012 | Antonetti et al. | |

FOREIGN PATENT DOCUMENTS

WO 2005115372 12/2005

OTHER PUBLICATIONS

Melnikova et al 'Anti-obesity therapies' Nature Review, Drug Discovery, vol. 5, p. 369-370, 2006.*
Rojas et al., 2-Acetyl-1, 3-cyclopentanedione-oxovanadium(IV) complexes. Acidity and implications for gastrointestinal absorption, Food and Chem Tox 45, 2007, 322-327.
Merenyi et al., Preparation of 2-Acetyl-1, 3-diketones from Acid Anhydrides and Isopropenyl Acetate, Acta Chemica Scandinavica 18 (1964), pp. 1368-1372.
Farese et al., Hepatic Atypical Protein Kinase C: An Inherited Survival-Longevity Gene that Now Fuels Insulin-Resistant Syndromes of Obesity, the Metabolic Syndrome and Type 2 Diabetes Mellitus, J. Clin. Med. 3, 2014, pp. 724-740.
Sajan et al., Akt-Dependent Phosphorylation of Hepatic FoxO1 is Compartmentalized on a WD40/Propeller/FYVE Scaffold and is Selectively Inhibited by Atypical PKC in Early Phases of Diet-Induced Obesity: A Mechanism for Impairing Gluconeogenic but Not Lipogenic Enzyme Expression, Diabetes 63, Aug. 2014, pp. 1-12.
Standaert et al., Protein Kinase C-ζ as a Downstream Effector of Phosphatidylinositol 3-Kinase during Insulin Stimulation in Rat Adipocytes: Potential Role in Glucose Transport, J of Bio Chem 272:48, Nov. 28, 1997, pp. 30075-30082.
International Search Report and Written Opinion for PCT/US14/48910 dated Nov. 28, 2014.
Sajan et al., 2012, Insulin Signalling in Hepatocytes of Type 2 Diabetic Humans. Excessive Expression and Activity of $PKC_{-I}$ and Dependent Processes and Reversal by $PKC_{-I}$ Inhibitors; Diabetologia 55, pp. 1446-1457.
Farese et al., 2010, Metabolic Functions of Atypical Protein Kinase C: "Good and Bad" as Defined by Nutritional Status (Invited Review), Am J Physiol Endocrinol Metab 298, E385-394.
Sajan et al., 2012, Correction of Metabolic Abnormalities in a Rodent Model of Obesity, Metabolic Syndrome and Type 2 Diabetes by Inhibitors of Hepatic Protein Kinase C-iota. Metabolism 61:459-469.
Matsumoto et al., 2003, PKCλ in liver mediates insulin-induced SREBP-1c expression and determines both hepatic lipid content and overall insulin sensitivity. J Clin Invest 112:935-944.
Taniguchi et al., Divergent regulation of hepatic glucose and lipid metabolism by phosphoinositide 3-kinase via Akt and PKCλ/ζ. Cell Metab, 3: 343-353, 2006.
Li et al., 2010, Bifurcation of insulin signaling pathway in rat liver: mTORC1 required for stimulation of lipogenesis, but not inhibition of gluceoneogenesis. Proc Natl Acad Sci USA 107:3441-3446.
Sajan et al., 2009, Role of atypical protein kinase C in activation of sterol regulatory element binding protein-1c and nuclear factor kappa B (NFkappaB) in liver of rodents used as model of diabetes, and relationships to hyperlipidaemia and insulin resistance. Diabetologia 52:1197-1207.

(Continued)

*Primary Examiner* — Theodore R. West
(74) *Attorney, Agent, or Firm* — Thomas|Horstemeyer, LLP

(57) ABSTRACT

Provided herein are methods of preventing or reducing weight gain in a subject in need thereof by administering 2-acetylcyclopentane-1,3-dione (ACPD).

9 Claims, 28 Drawing Sheets

Specification includes a Sequence Listing.

(56) References Cited

OTHER PUBLICATIONS

Sajan et al., 2009, Critical role of atypical protein kinase C in activating hepatic SREBP-1c and NF$_K$B in obesity, J Lipid Res 50:1133-1145.

Sajan et al., Meformin action in human hepatocytes: Co-activation of atypical protein kinase C alters 5'-AMP-activated protein kinase effects on lipogenic and gluconeogenic enzyme expression, Diabetologia 56:11, Nov. 2013, pp. 2507-2516.

Farese et al., 2007, Muscle-specific knockout of protein kinase C-λ impairs glucose transport and induces metabolic and diabetic syndromes. J Clin Invest 117:2289-2301.

Pillai et al., 2011, ICA-1: A novel PKC$_{-I}$ inhibitor that abrogates cell proliferation and induces apoptosis in neuroblastoma. Internat J Biochem and Cell Biol.43:784-794.

Doornbos et al., 1999, Protein kinase Czeta is a negative regulator of protein kinase B activity. J Biol Chem 274:8589-8596.

Ding et al., 2008, PI3K activates negative and positive signals to regulate TRB3 expression in hepatic cells. Exp Cell Res 314:1566-1574.

Kitamura et al., 2004, New insights into the integrated physiology of insulin action. Rev Endocrol Metab Disord 5:143-149.

Matsumoto et al., 2007, Impaired regulation of hepatic glucose production in mice lacking the forkhead transcription factor foxo 1 in liver. Cell Metab 6:208-216.

Standaert et al., 2004, Insulin-induced activation of atypical protein kinase C, but not protein kinase B, is maintained in diabetic (ob/ob and Goto-Kakazaki) liver: Contrasting insulin signaling patterns in liver versus muscle define phenotypes of type 2 diabetic and high-fat-induced insulin-resistant states. J. Biol Chem 279:24929-24934.

Hundal et al., (2000), Mechanism by which metformin reduces glucose production in type 2 diabetes. Diabetes 49: 2063-2069, 2000.

Luna et al., (2006), Metformin improves atypical protein kinase C activation by insulin and phosphatidylinositol-3,4,5-(PO4) in diabetic muscle. Diabetologia, 49:375-382.

Sajan et al., (2010), AICAR and metformin, but not exercise, increase muscle glucose transport through AMPK-, ERK- and PDK1-dependent activation of atypical PKC. Am J Physiol Endocrinol Metab 298:E179-E192.

Zhou et al., (2001), Role of AMP-activated protein kinase in mechanism of metformin action. J Clin Invest 108:1167-1174.

Musi et al., (2002), Metformin increases AMP-activated protein kinase activity in skeletal muscle of subjects with type 2 diabetes. Diabetes 51:2074-2081.

Shaw et al., (2005), The kinase LKB1 mediates glucose homeostasis in liver and therapeutic effects of metformin. Science 310:1642-1646.

Stephenne et al., (2011), Metformin activates AMP-activated kinase in primary human hepatocytes by decreasing cellular energy status. Diabetologia 54:3101-3110.

He et al., (2009), Metformin and insulin suppress hepatic gluconeogenesis through phosphorylation of CREB binding protein. Cell 15:635-646.

Chen et al., (2002), Activation of the ERK pathway and atypical protein kinase C isoforms in exercise- and AICAR-stimulated glucose transport. J Biol Chem 277:23554-23562.

Liu et al., (2001), Insulin stimulates PKCzeta-mediated phosphorylation of insulin receptor substrate-1 (IRS-1). A self-attenuated mechanism to negatively regulate IRS proteins. J Biol Chem 276:14459-14465.

Sajan et al., (2004), Tissue-specific differences in activation of atypical protein kinase C and protein kinase B in muscle, liver, and adipocytes of insulin receptor substrate-1 knockout mice. Mol Endocrinol 18:2513-2521.

Guo et al., (2009), The Irs1 branch of the insulin signaling cascade plays a dominant role in hepatic nutrient homeostasis. Mol Cell Biol 29:5070-5083.

Yang et al., Central role of ceramide biosynthesis in body weight regulation, energy metabolism, and the metabolic syndrome, Amer J Physiol Endocrinol Metab 297:E211-E224, 2009.

Ussher et al., Inhibition of de novo ceramide synthesis reverses diet-induced insulin resistance and enhances whole-body oxygen consumption. Diabetes 59: 2453-2464, 2010.

Bikman et al., Ceramides as modulators of cellular and whole-body metabolism. J Clin Invest 121:4222-4230, 2011.

Konishi et al., The pleckstrin homology domain of RAC protein kinase associates with the regulatory domain of protein kinase Cζ, Biochem Biophys Res Commun 205:1770-1775, 1994.

Minokoshi et al., (2003), Tissue-specific ablation of the GLUT4 glucose transporter or the insulin receptor challenges assumptions about insulin action and glucose homeostasis. J Biol Chem 278:33609-33612.

Fritzius et al., (2006), A WD-FYVE protein binds to the kinases Akt and PKCZ/Λ, Biochem J 399:9-20.

Fritzius et al., (2008) Akt and Foxo1-interacting WD-repeat-FYVE protein promotes adipogenesis. The EMBO J 27:1399-1410.

Fritzius et al., (2007) WD-repeat-propeller-FYVE protein, ProF, binds VAMP2 and protein kinase CZ. FEBS J 274:1552-1566.

Weyrich et al., (2007) The Par6alpha/aPKC complex regulates Akt1 activity by phosphorylating Thr34 in the PH-domain. Mol Cell Endocrinol 268:30-36.

* cited by examiner

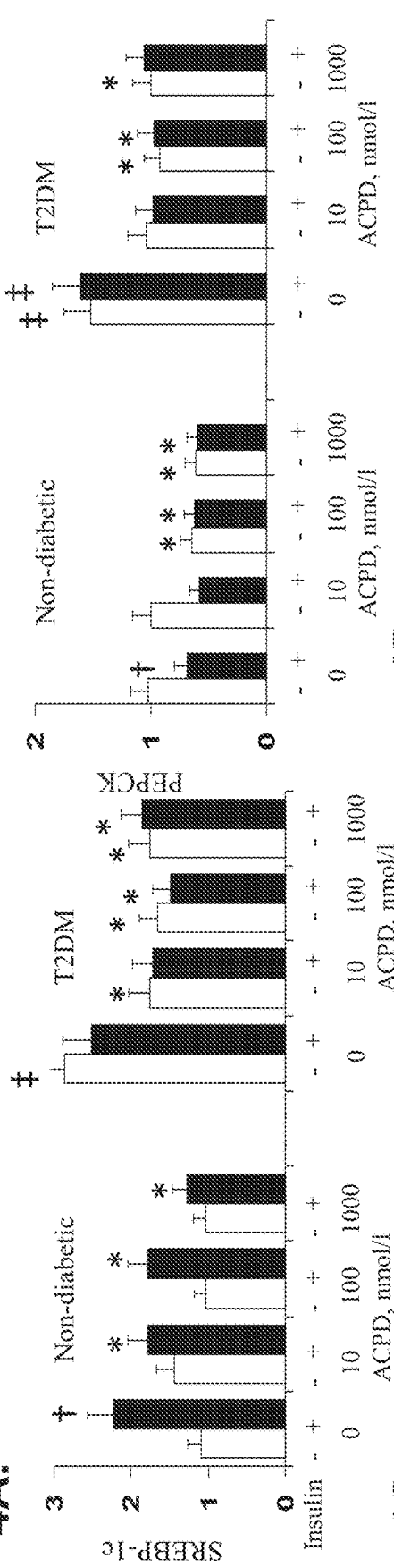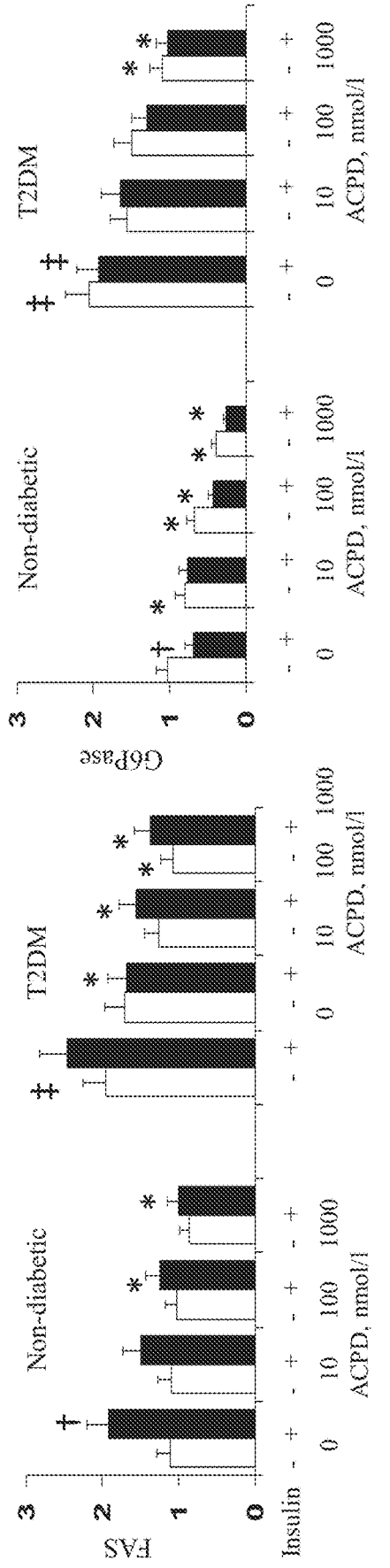
FIGS. 4A-4D

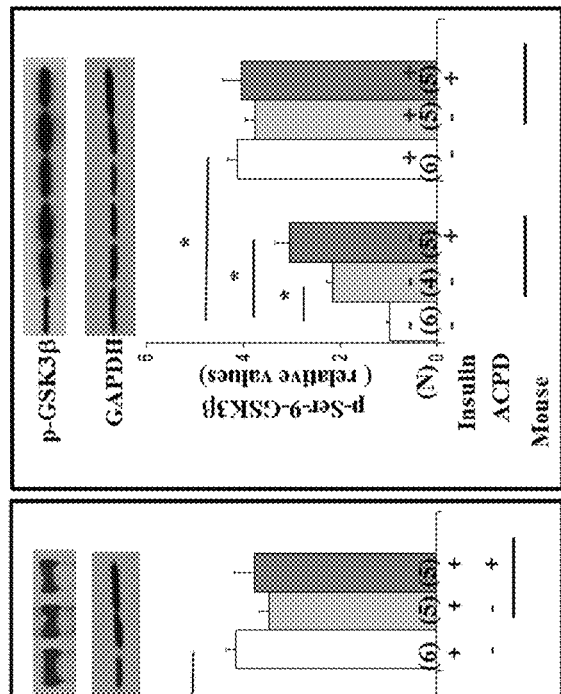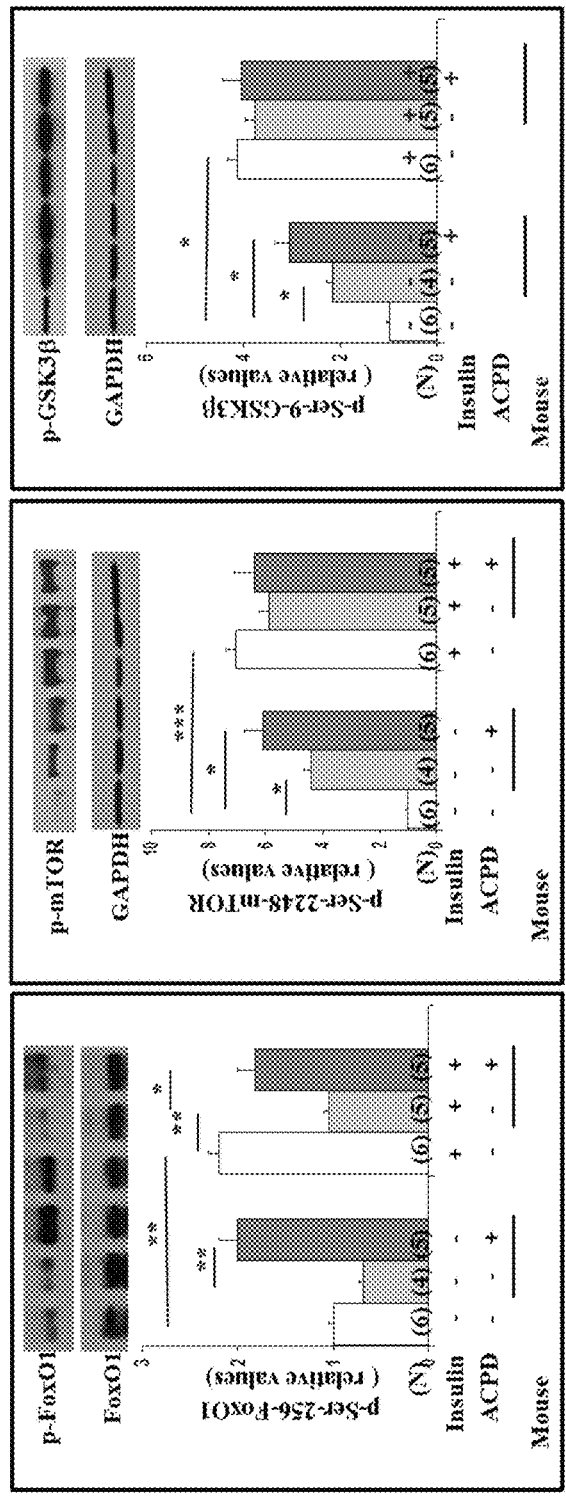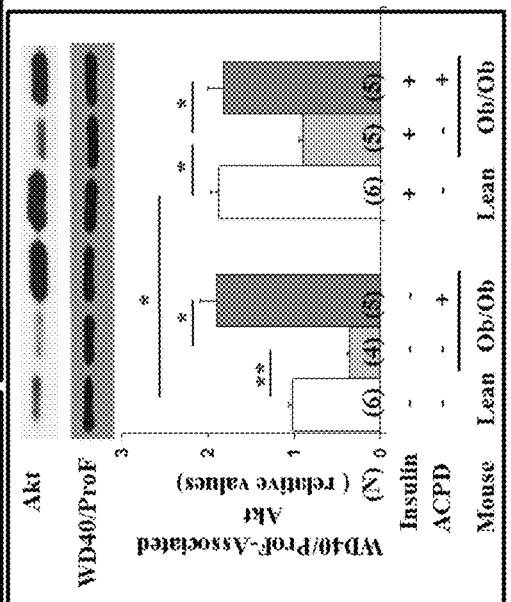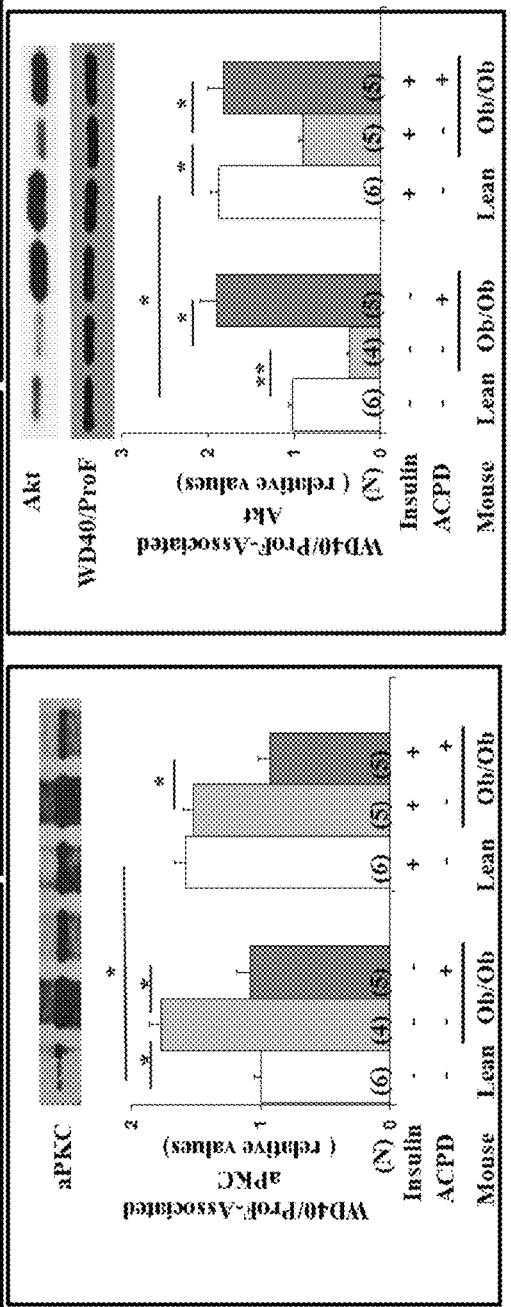
FIG. 20A  FIG. 20B  FIG. 20C  FIG. 20D  FIG. 20E

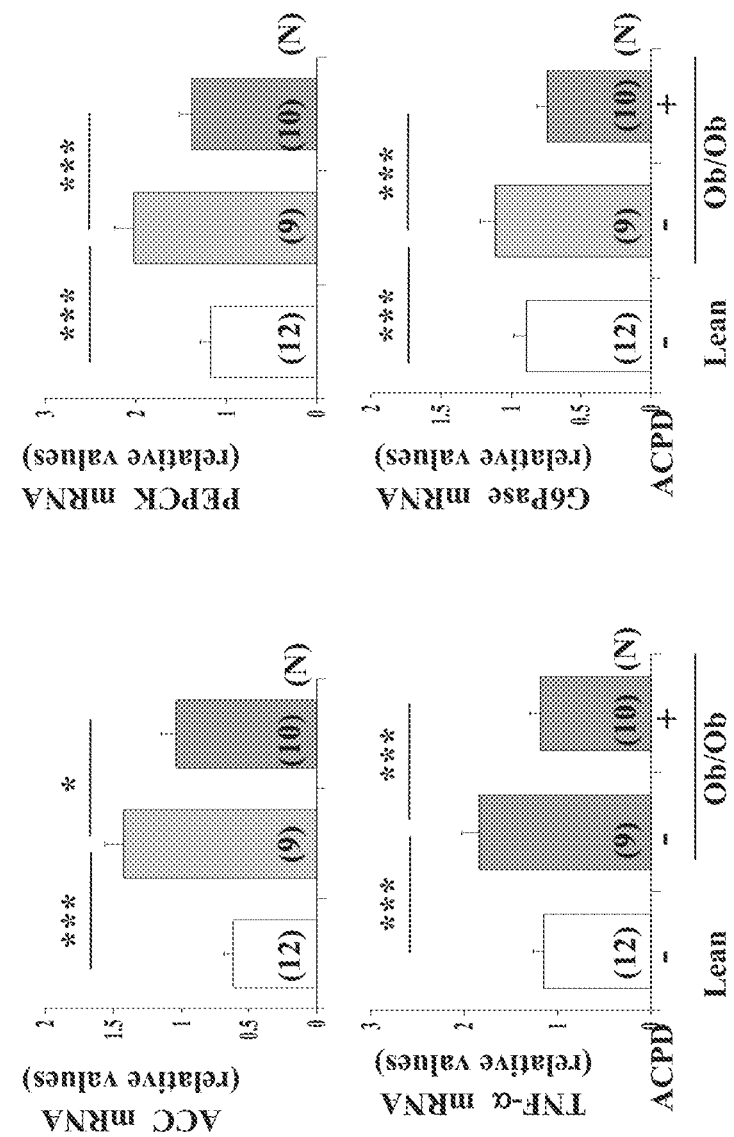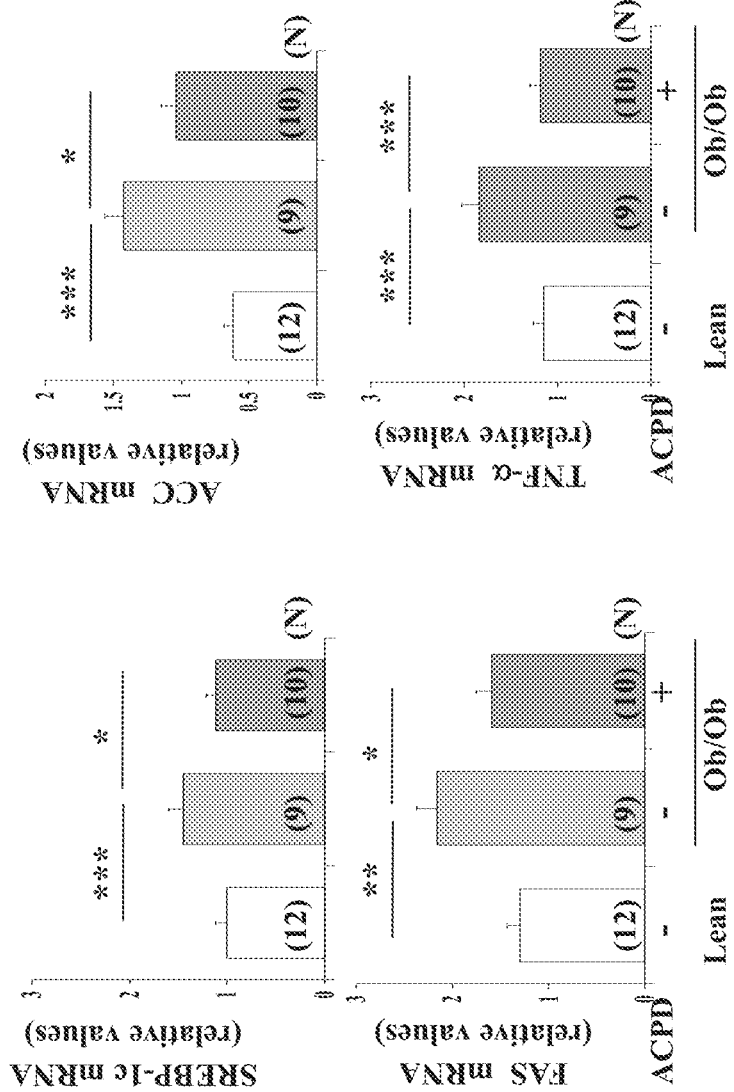
FIG. 21A FIG. 21C FIG. 21E
FIG. 21B FIG. 21D FIG. 21F

```
                        SEQUENCE LISTING

<160> NUMBER OF SEQ ID NOS: 14

<210> SEQ ID NO 1
<211> LENGTH: 29
<212> TYPE: DNA
<213> ORGANISM: Artificial Sequence
<220> FEATURE:
<223> OTHER INFORMATION: Primer Sequence

<400> SEQUENCE: 1
atcggcgcgg aagctgtcgg ggtagcgtc                                        29

<210> SEQ ID NO 2
<211> LENGTH: 27
<212> TYPE: DNA
<213> ORGANISM: Artificial Sequence
<220> FEATURE:
<223> OTHER INFORMATION: Primer Sequence

<400> SEQUENCE: 2
actgtcttgg ttgatgagct ggagcat                                          27

<210> SEQ ID NO 3
<211> LENGTH: 22
<212> TYPE: DNA
<213> ORGANISM: Artificial Sequence
<220> FEATURE:
<223> OTHER INFORMATION: Primer Sequence

<400> SEQUENCE: 3
gacagcctgc cccaggcagt ga                                               22

<210> SEQ ID NO 4
<211> LENGTH: 22
<212> TYPE: DNA
<213> ORGANISM: Artificial Sequence
<220> FEATURE:
<223> OTHER INFORMATION: Primer Sequence

<400> SEQUENCE: 4
ctggccacat ctcgagggtc ag                                               22

<210> SEQ ID NO 5
<211> LENGTH: 23
<212> TYPE: DNA
<213> ORGANISM: Artificial Sequence
<220> FEATURE:
<223> OTHER INFORMATION: Primer Sequence

<400> SEQUENCE: 5
accgacttca tgaatttgct gat                                              23

<210> SEQ ID NO 6
<211> LENGTH: 20
<212> TYPE: DNA
<213> ORGANISM: Artificial Sequence
<220> FEATURE:
<223> OTHER INFORMATION: Primer Sequence

<400> SEQUENCE: 6
```

-continued aagctgaaag ctttctgtct                                          20

<210> SEQ ID NO 7
<211> LENGTH: 22
<212> TYPE: DNA
<213> ORGANISM: Artificial Sequence
<220> FEATURE:
<223> OTHER INFORMATION: Primer Sequence

<400> SEQUENCE: 7
tgctgctcac tttccccacc ag                                       22

<210> SEQ ID NO 8
<211> LENGTH: 21
<212> TYPE: DNA
<213> ORGANISM: Artificial Sequence
<220> FEATURE:
<223> OTHER INFORMATION: Primer Sequence

<400> SEQUENCE: 8
tctccaaagt ccacaggagg t                                        21

<210> SEQ ID NO 9
<211> LENGTH: 21
<212> TYPE: DNA
<213> ORGANISM: Artificial Sequence
<220> FEATURE:
<223> OTHER INFORMATION: Primer Sequence

<400> SEQUENCE: 9
tgaaagactt gctcgagatg t                                        21

<210> SEQ ID NO 10
<211> LENGTH: 21
<212> TYPE: DNA
<213> ORGANISM: Artificial Sequence
<220> FEATURE:
<223> OTHER INFORMATION: Primer Sequence

<400> SEQUENCE: 10
aaagaactta tagccccct t                                         21

<210> SEQ ID NO 11
<211> LENGTH: 20
<212> TYPE: DNA
<213> ORGANISM: Artificial Sequence
<220> FEATURE:
<223> OTHER INFORMATION: Primer Sequence

<400> SEQUENCE: 11
acggcatgga tctcaaagac                                          20

<210> SEQ ID NO 12
<211> LENGTH: 20
<212> TYPE: DNA
<213> ORGANISM: Artificial Sequence
<220> FEATURE:
<223> OTHER INFORMATION: Primer Sequence

<400> SEQUENCE: 12
agatagcaaa tcggctgacg                                          20

<210> SEQ ID NO 13
<211> LENGTH: 20
<212> TYPE: DNA

```
<213> ORGANISM: Artificial Sequence
<220> FEATURE:
<223> OTHER INFORMATION: Primer Sequence

<400> SEQUENCE: 13
gacttcatga atttgctgat                                               20

<210> SEQ ID NO 14
<211> LENGTH: 20
<212> TYPE: DNA
<213> ORGANISM: Artificial Sequence
<220> FEATURE:
<223> OTHER INFORMATION: Primer Sequence

<400> SEQUENCE: 14
aagctgaaag ctttctgtct                                               20
```

TREATING AND/OR PREVENTING INSULIN-RESISTANCE RELATED WEIGHT GAIN

CROSS-REFERENCE TO RELATED APPLICATIONS

This application is a divisional of U.S. application Ser. No. 14/907,840, filed Jan. 27, 2016. U.S. application Ser. No. 14/907,840 is the 35 U.S.C. § 371 national stage of, and claims priority to and the benefit of, PCT application PCT/US2014/048910, filed Jul. 30, 2014, which claims priority to and the benefit of U.S. Provisional Application No. 61/859,875, filed on Jul. 30, 2013, herein incorporated by reference in their entirety.

STATEMENT REGARDING FEDERALLY SPONSORED RESEARCH OR DEVELOPMENT

This invention was made with government support under Grant Number DK065969 awarded by The National Institutes of Health. The government has certain rights in the invention.

SEQUENCE LISTING

This application contains a sequence listing filed in electronic form as an ASCII.txt file entitled Sequence Listing 292103-2270.K created on Jul. 30, 2014, and having a size of 2,954 bytes. The content of the sequence listing is incorporated herein by reference in its entirety.

BACKGROUND

Obesity is an epidemic that has become the leading preventable cause of death worldwide. Authorities internationally view obesity as one of the most serious public health problems of the 21$^{st}$ century. In 2013, the American Medical Association classified obesity as a disease. Generally, obesity is the condition in which excess body fat has accumulated to the extent that adversely affects morbidity and mortality. In the United States, obesity is estimated to cause between 112,000 and 365,000 deaths per year and reduces life expectancy by approximately six to seven years. Comorbities such as type-2 diabetes and metabolic syndrome are characterized by glucose intolerance, high blood pressure, high blood cholesterol, and high triglyceride levels.

Health complications are either caused directly by obesity or indirectly through related mechanisms sharing a common cause, such as poor diet and/or sedentary lifestyle. Health complications fall into two major categories, including those caused by the increased fat mass or an increased number of fat cells. Osteoarthritis and obstructive sleep apnea are examples of complications due to increased fat mass. Diabetes, cancer, cardiovascular disease, and non-alcoholic fatty liver disease are examples of complications due to increased number of fat cells.

Despite public health efforts to understand and correct environmental factors contributing to obesity, extensive research into understanding the factors contributing to the disease, and significant efforts to develop pharmaceutical and surgical treatments, obesity remains a significant public health and policy issue. Indeed, World Health Organization predicts that obesity may soon replace more traditional public health concerns such as under nutrition and infectious disease as the most significant cause of poor health. Given this, there exists a long-felt and unmet need to provide treatments for obesity and related disorders.

SUMMARY

Provided herein are compounds, compositions, pharmaceutical formulations, methods of treating and methods of using aPKC inhibitors for treating and/or preventing of aPKC abnormalities. In one aspect, described herein is a method of treating or preventing an aPKC abnormality in a subject in need thereof, the method containing the steps of administering an effective amount of an aPKC inhibitor or a derivative thereof to the subject, where the aPKC inhibitor has a formula according to Formula I:

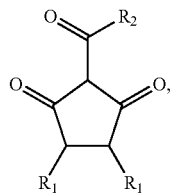

Formula I where each where each $R_1$, when taken separately, is independently selected from the group consisting of: hydrogen, halo, C—C6 alkyl, C2-C6 alkenyl, C1-C6 haloalkyl, C1-C6 alkoxy, C1-C6 haloalkoxy, C2-C6 alkynyl, C3-C8 cycloalkenyl, (C3-C8 cycloalkyl)C1-C6 alkyl, (C3-C8 cycloalkyl)C2-C6 alkenyl, (C3-C8 cycloalkyl) C1-C6 alkoxy, C3-C7 heterocycloalkyl, (C3-C7 heterocycloalkyl) C1-C6 alkyl, (C3-C7 heterocycloalkyl)C2-C6 alkenyl, (C3-C7 heterocycloalkyl)C1-C6 alkoxyl, hydroxy, carboxy, oxo, sulfanyl, C1-C6 alkylsulfanyl, aryl, heteroaryl, aryloxy, heteroaryloxy, aralkyl, heteroaralkyl, aralkoxy, heteroaralkoxy, nitro, cyano, amino, C1-C6 alkylamino, di-(C1-C6 alkyl) amino, carbamoyl, (C1-C6 alkyl)carbonyl, (C1-C6 alkoxy) carbonyl, (C1-C6 alkyl)aminocarbonyl, di-(C1-C6 alkyl) aminocarbonyl, arylcarbonyl, aryloxycarbonyl, (C1-C6 alkyl)sulfonyl, and arylsulfonyl, or, when taken together with the atoms to which they are attached, form a C5-C10-membered aromatic, heterocyclic, fused aromatic, fused heterocyclic, biaromatic, or bihetereocyclic ring, and where $R_2$ is selected from the group consisting of: hydrogen, halo, C1-C6 alkyl, tert-butyl, C2-C6 alkenyl, C1-C6 haloalkyl, C1-C6 alkoxy, C1-C6 haloalkoxy, C2-C6 alkynyl, C3-C8 cycloalkenyl, (C3-C8 cycloalkyl)C1-C6 alkyl, (C3-C8 cycloalkyl)C2-C6 alkenyl, (C3-C8 cycloalkyl) C1-C6 alkoxy, C3-C7 heterocycloalkyl, (C3-C7 heterocycloalkyl) C1-C6 alkyl, (C3-C7 heterocycloalkyl)C2-C6 alkenyl, (C3-C7 heterocycloalkyl)C1-C6 alkoxyl, hydroxy, carboxy, oxo, sulfanyl, C1-C6 alkyl furan, C2-C6 alkenyl furan, C1-C6 alkylsulfanyl, aryl, heteroaryl, aryloxy, heteroaryloxy, aralkyl, heteroaralkyl, aralkoxy, heteroaralkoxy, nitro, cyano, amino, C1-C6 alkylamino, di-(C1-C6 alkyl)amino, carbamoyl, (C1-C6 alkyl)carbonyl, (C1-C6 alkoxy)carbonyl, (C1-C6 alkyl)aminocarbonyl, di-(C1-C6 alkyl)aminocarbonyl, arylcarbonyl, aryloxycarbonyl, (C1-C6 alkyl) sulfonyl, arylsulfonyl, and 2-acetyl-3-oxobutanimidoyl cyanide.

In some embodiments of the method of treating or preventing an aPKC abnormality in a subject in need thereof described above, the derivative of Formula I is a salt or alcohol of Formula I. In further embodiments of these methods, the $R_2$ of Formula I is 2-propylfuran, (E)-2-(prop- 1-en-1-yl)furan, or tert-butyl. In other embodiments of any of the described methods of treating or preventing an aPKC abnormality in a subject in need thereof described above, the $R_1$ of Formula I, together with the atoms to which they are attached, form benzene. In any of these methods, the effective amount of Formula I or derivative thereof ranges from about 0.001 mg to about 1,000 mg. The effective amount can be administered to the subject in a dosage form formulated for oral, vaginal, intravenous, transdermal, subcutaneous, intraperitoneal, or intramuscular administration. In any of these embodiments, the aPKC abnormality treated by administration of a compound according to Formula I or a derivative thereof to a subject in need thereof is obesity, glucose intolerance, metabolic syndrome, hyperinsulinemia, hepatosteatosis, non-alcoholic cirrhosis, hypertriglyceridemia, hypercholesterolemia, polycystic ovary disease, and Alzheimer's disease.

In another aspect, provided is a method for treating or preventing an aPKC abnormality containing the steps of contacting a hepatic cell with an effective amount of an aPKC inhibitor or a derivative thereof, where the aPKC inhibitor has a formula according to Formula I:

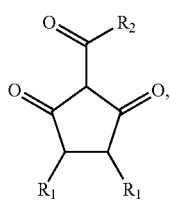

Formula I where each $R_1$, when taken separately, is independently selected from the group consisting of: hydrogen, halo, C—C6 alkyl, C2-C6 alkenyl, C1-C6 haloalkyl, C1-C6 alkoxy, C1-C6 haloalkoxy, C2-C6 alkynyl, C3-C8 cycloalkenyl, (C3-C8 cycloalkyl)C1-C6 alkyl, (C3-C8 cycloalkyl) C2-C6 alkenyl, (C3-C8 cycloalkyl) C1-C6 alkoxy, C3-C7 heterocycloalkyl, (C3-C7 heterocycloalkyl)C1-C6 alkyl, (C3-C7 heterocycloalkyl)C2-C6 alkenyl, (C3-C7 heterocycloalkyl)C1-C6 alkoxyl, hydroxy, carboxy, oxo, sulfanyl, C1-C6 alkylsulfanyl, aryl, heteroaryl, aryloxy, heteroaryloxy, aralkyl, heteroaralkyl, aralkoxy, heteroaralkoxy, nitro, cyano, amino, C1-C6 alkylamino, di-(C1-C6 alkyl)amino, carbamoyl, (C1-C6 alkyl)carbonyl, (C1-C6 alkoxy)carbonyl, (C1-C6 alkyl)aminocarbonyl, di-(C1-C6 alkyl)aminocarbonyl, arylcarbonyl, aryloxycarbonyl, (C1-C6 alkyl)sulfonyl, and arylsulfonyl, or, when taken together with the atoms to which they are attached, form a C5-C10-membered aromatic, heterocyclic, fused aromatic, fused heterocyclic, biaromatic, or bihetereocyclic ring, and where $R_2$ is selected from the group consisting of: hydrogen, halo, C1-C6 alkyl, tert-butyl, C2-C6 alkenyl, C1-C6 haloalkyl, C1-C6 alkoxy, C1-C6 haloalkoxy, C2-C6 alkynyl, C3-C8 cycloalkenyl, (C3-C8 cycloalkyl)C1-C6 alkyl, (C3-C8 cycloalkyl)C2-C6 alkenyl, (C3-C8 cycloalkyl) C1-C6 alkoxy, C3-C7 heterocycloalkyl, (C3-C7 heterocycloalkyl) C1-C6 alkyl, (C3-C7 heterocycloalkyl)C2-C6 alkenyl, (C3-C7 heterocycloalkyl)C1-C6 alkoxyl, hydroxy, carboxy, oxo, sulfanyl, C1-C6 alkyl furan, C2-C6 alkenyl furan, C1-C6 alkylsulfanyl, aryl, heteroaryl, aryloxy, heteroaryloxy, aralkyl, heteroaralkyl, aralkoxy, heteroaralkoxy, nitro, cyano, amino, C1-C6 alkylamino, di-(C1-C6 alkyl)amino, carbamoyl, (C1-C6 alkyl)carbonyl, (C1-C6 alkoxy)carbonyl, (C1-C6 alkyl)aminocarbonyl, di-(C1-C6 alkyl)aminocarbonyl, arylcarbonyl, aryloxycarbonyl, (C1-C6 alkyl)sulfonyl, arylsulfonyl, and 2-acetyl-3-oxobutanimidoyl cyanide.

In some embodiments of the method of treating or preventing an aPKC abnormality, described above, the derivative of Formula I is a salt or alcohol of Formula I. In further embodiments of these methods, the $R_2$ of Formula I is 2-propylfuran, (E)-2-(prop-1-en-1-yl)furan, or tert-butyl. In other embodiments of any of the described methods of treating or preventing an aPKC abnormality described above, the $R_1$ of Formula I, together with the atoms to which they are attached, form benzene. In any of these methods, the effective amount of Formula I or derivative thereof ranges from about 0.001 mg to about 1,000 mg. The effective amount can be administered to the subject in a dosage form formulated for oral, vaginal, intravenous, transdermal, subcutaneous, intraperitoneal, or intramuscular administration. In any of these embodiments, the aPKC abnormality treated by contacting a hepatic cell with an effective amount of an aPKC inhibitor, where the aPKC inhibitor has a Formula according to Formula I or a derivative thereof is obesity, glucose intolerance, metabolic syndrome, hyperinsulinemia, hepatosteatosis, non-alcoholic cirrhosis, hypertriglyceridemia, hypercholesterolemia, polycystic ovary disease, and Alzheimer's disease.

In a further aspect, provide is a kit containing an effective amount of aPKC inhibitor or a derivative thereof provided in a dosage form, where the aPKC inhibitor has a Formula according to Formula 1:

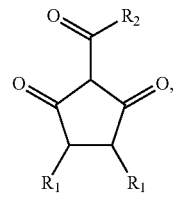

Formula I where each $R_1$, when taken separately, is independently selected from the group consisting of: hydrogen, halo, C—C6 alkyl, C2-C6 alkenyl, C1-C6 haloalkyl, C1-C6 alkoxy, C1-C6 haloalkoxy, C2-C6 alkynyl, C3-C8 cycloalkenyl, (C3-C8 cycloalkyl)C1-C6 alkyl, (C3-C8 cycloalkyl) C2-C6 alkenyl, (C3-C8 cycloalkyl) C1-C6 alkoxy, C3-C7 heterocycloalkyl, (C3-C7 heterocycloalkyl)C1-C6 alkyl, (C3-C7 heterocycloalkyl)C2-C6 alkenyl, (C3-C7 heterocycloalkyl)C1-C6 alkoxyl, hydroxy, carboxy, oxo, sulfanyl, C1-C6 alkylsulfanyl, aryl, heteroaryl, aryloxy, heteroaryloxy, aralkyl, heteroaralkyl, aralkoxy, heteroaralkoxy, nitro, cyano, amino, C1-C6 alkylamino, di-(C1-C6 alkyl)amino, carbamoyl, (C1-C6 alkyl)carbonyl, (C1-C6 alkoxy)carbonyl, (C1-C6 alkyl)aminocarbonyl, di-(C1-C6 alkyl)aminocarbonyl, arylcarbonyl, aryloxycarbonyl, (C1-C6 alkyl)sulfonyl, and arylsulfonyl, or, when taken together with the atoms to which they are attached, form a C5-C10-membered aromatic, heterocyclic, fused aromatic, fused heterocyclic, biaromatic, or bihetereocyclic ring, and where $R_2$ is selected from the group consisting of: hydrogen, halo, C1-C6 alkyl, tert-butyl, C2-C6 alkenyl, C1-C6 haloalkyl, C1-C6 alkoxy, C1-C6 haloalkoxy, C2-C6 alkynyl, C3-C8 cycloalkenyl, (C3-C8 cycloalkyl)C1-C6 alkyl, (C3-C8 cycloalkyl)C2-C6 alkenyl, (C3-C8 cycloalkyl) C1-C6 alkoxy, C3-C7 heterocycloalkyl, (C3-C7 heterocycloalkyl) C1-C6 alkyl, (C3-C7 heterocycloalkyl)C2-C6 alkenyl, (C3-

C7 heterocycloalkyl)C1-C6 alkoxyl, hydroxy, carboxy, oxo, sulfanyl, C1-C6 alkyl furan, C2-C6 alkenyl furan, C1-C6 alkylsulfanyl, aryl, heteroaryl, aryloxy, heteroaryloxy, aralkyl, heteroaralkyl, aralkoxy, heteroaralkoxy, nitro, cyano, amino, C1-C6 alkylamino, di-(C1-C6 alkyl)amino, carbamoyl, (C1-C6 alkyl)carbonyl, (C1-C6 alkoxy)carbonyl, (C1-C6 alkyl)aminocarbonyl, di-(C1-C6 alkyl)aminocarbonyl, arylcarbonyl, aryloxycarbonyl, (C1-C6 alkyl)sulfonyl, arylsulfonyl, and 2-acetyl-3-oxobutanimidoyl cyanide; and instructions fixed in a tangible medium of expression, where the instructions provide directions for administering the aPKC inhibitor or a derivative thereof to a subject having an aPKC abnormality.

In some embodiments of this aspect, the dosage form is formulated for oral, vaginal, intravenous, transdermal, subcutaneous, intraperitoneal, or intramuscular administration. In additional embodiments of this aspect, the effective amount of the aPKC inhibitor ranges from about 0.001 mg to about 1,000 mg. In other embodiments of the kit according to this aspect, the aPKC abnormality is obesity, glucose intolerance, metabolic syndrome, hyperinsulinemia, hepatosteatosis, non-alcoholic cirrhosis, hypertriglyceridemia, hypercholesterolemia, polycystic ovary disease, or Alzheimer's disease.

In another aspect, provided herein are pharmaceutical formulations for treating or preventing an aPKC abnormality in a subject in need thereof containing an effective amount of aPKC inhibitor or a derivative; and a pharmaceutically acceptable carrier, where the aPKC inhibitor has a formula according to Formula I:

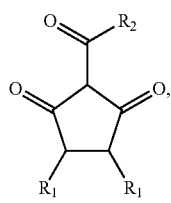

Formula I where each $R_1$, when taken separately, is independently selected from the group consisting of: hydrogen, halo, C—C6 alkyl, C2-C6 alkenyl, C1-C6 haloalkyl, C1-C6 alkoxy, C1-C6 haloalkoxy, C2-C6 alkynyl, C3-C8 cycloalkenyl, (C3-C8 cycloalkyl)C1-C6 alkyl, (C3-C8 cycloalkyl) C2-C6 alkenyl, (C3-C8 cycloalkyl) C1-C6 alkoxy, C3-C7 heterocycloalkyl, (C3-C7 heterocycloalkyl)C1-C6 alkyl, (C3-C7 heterocycloalkyl)C2-C6 alkenyl, (C3-C7 heterocycloalkyl)C1-C6 alkoxyl, hydroxy, carboxy, oxo, sulfanyl, C1-C6 alkylsulfanyl, aryl, heteroaryl, aryloxy, heteroaryloxy, aralkyl, heteroaralkyl, aralkoxy, heteroaralkoxy, nitro, cyano, amino, C1-C6 alkylamino, di-(C1-C6 alkyl)amino, carbamoyl, (C1-C6 alkyl)carbonyl, (C1-C6 alkoxy)carbonyl, (C1-C6 alkyl)aminocarbonyl, di-(C1-C6 alkyl)aminocarbonyl, arylcarbonyl, aryloxycarbonyl, (C1-C6 alkyl)sulfonyl, and arylsulfonyl, or, when taken together with the atoms to which they are attached, form a C5-C10-membered aromatic, heterocyclic, fused aromatic, fused heterocyclic, biaromatic, or biheteroecyclic ring, and where $R_2$ is selected from the group consisting of: hydrogen, halo, C1-C6 alkyl, tert-butyl, C2-C6 alkenyl, C1-C6 haloalkyl, C1-C6 alkoxy, C1-C6 haloalkoxy, C2-C6 alkynyl, C3-C8 cycloalkenyl, (C3-C8 cycloalkyl)C1-C6 alkyl, (C3-C8 cycloalkyl)C2-C6 alkenyl, (C3-C8 cycloalkyl) C1-C6 alkoxy, C3-C7 heterocycloalkyl, (C3-C7 heterocycloalkyl) C1-C6 alkyl, (C3-C7 heterocycloalkyl)C2-C6 alkenyl, (C3-C7 heterocycloalkyl)C1-C6 alkoxyl, hydroxy, carboxy, oxo, sulfanyl, C1-C6 alkylsulfanyl, aryl, heteroaryl, aryloxy, heteroaryloxy, aralkyl, heteroaralkyl, aralkoxy, heteroaralkoxy, nitro, cyano, amino, C1-C6 alkylamino, di-(C1-C6 alkyl)amino, carbamoyl, (C1-C6 alkyl)carbonyl, (C1-C6 alkoxy)carbonyl, (C1-C6 alkyl)aminocarbonyl, di-(C1-C6 alkyl)aminocarbonyl, arylcarbonyl, aryloxycarbonyl, (C1-C6 alkyl)sulfonyl, arylsulfonyl, and 2-acetyl-3-oxobutanimidoyl cyanide.

In some embodiments of this aspect, the derivative of Formula I is a salt or an alcohol of Formula I. In further embodiments of this aspect, $R_2$ of Formula I is 2-propyl-furan, (E)-2-(prop-1-en-1-yl)furan or tert-butyl. In other embodiments of this aspect, the $R_1$ of Formula I together with the atoms to which they are attached form benzene. In additional embodiments of this aspect, the effective amount ranges from about 0.001 mg to about 1,000 mg. In further embodiments of this aspect, the aPKC abnormality is selected from the group consisting of obesity, glucose intolerance, metabolic syndrome, hyperinsulinemia, hepatosteatosis, non-alcoholic cirrhosis, hypertriglyceridemia, hypercholesterolemia, polycystic ovary disease, and Alzheimer's disease.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 4A-4D show the effect of ACPD on expression of lipogenic and gluconeogenic factors in basal and insulin-stimulated hepatocytes of non-diabetic and type 2 diabetic (T2DM) humans. mRNA levels of SREBP-1c (FIG. 4A), PEPCK (FIG. 4B), FAS (FIG. 4C), and G6Pase (FIG. 4D) were measured in hepatocytes of non-diabetic and T2DM humans treated for 24 hours without (0) or with indicated concentrations of ACPD, in the presence (solid bars) and absence (open bars) of about 1 μmol/l insulin. Relative values are mean±SEM of 5 determinations. Symbols indicate: *, P<0.05, ACPD-treated basal or ACPD-treated+ insulin-stimulated value versus corresponding basal or insulin-stimulated value of the ACPD-untreated (0) group; †, P<0.05, insulin-treated value of the 0 group versus basal value of the 0 group; and ‡, P<0.05, basal or insulin-stimulated diabetic value of the 0 group versus basal or insulin-stimulated non-diabetic value of the 0 group.

Figure 5A:
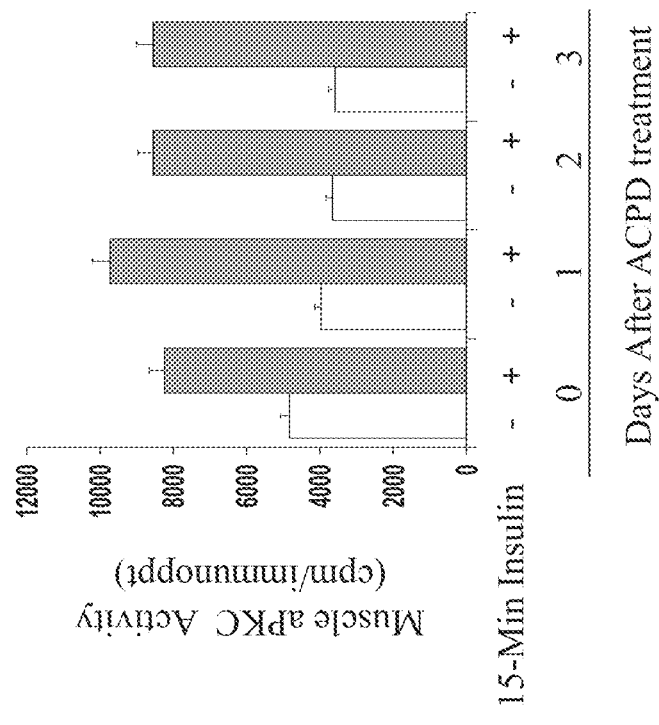
Figure 5B:
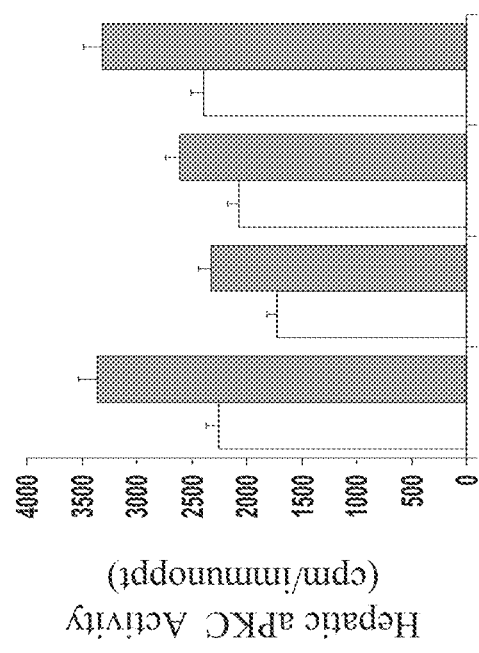

FIGS. 5A-5B show the effect of ACPD on resting/basal and insulin-stimulated aPKC activity in mouse liver (FIG. 5A) and muscle (FIG. 5B). Normal mice were treated for 24, 48, or 72 hours with a single subcutaneous injection of ACPD (10 mg/kg body weight), and, at 24, 48, or 72 hours, the mice were injected intraperitoneally with 1 U/kg body weight insulin and killed 15 minutes later. Tissues were examined for immunprecipitable total aPKC activity. Values are mean±SEM of 4 determinations.

Figures 6A, 6B, 6C, 6D:
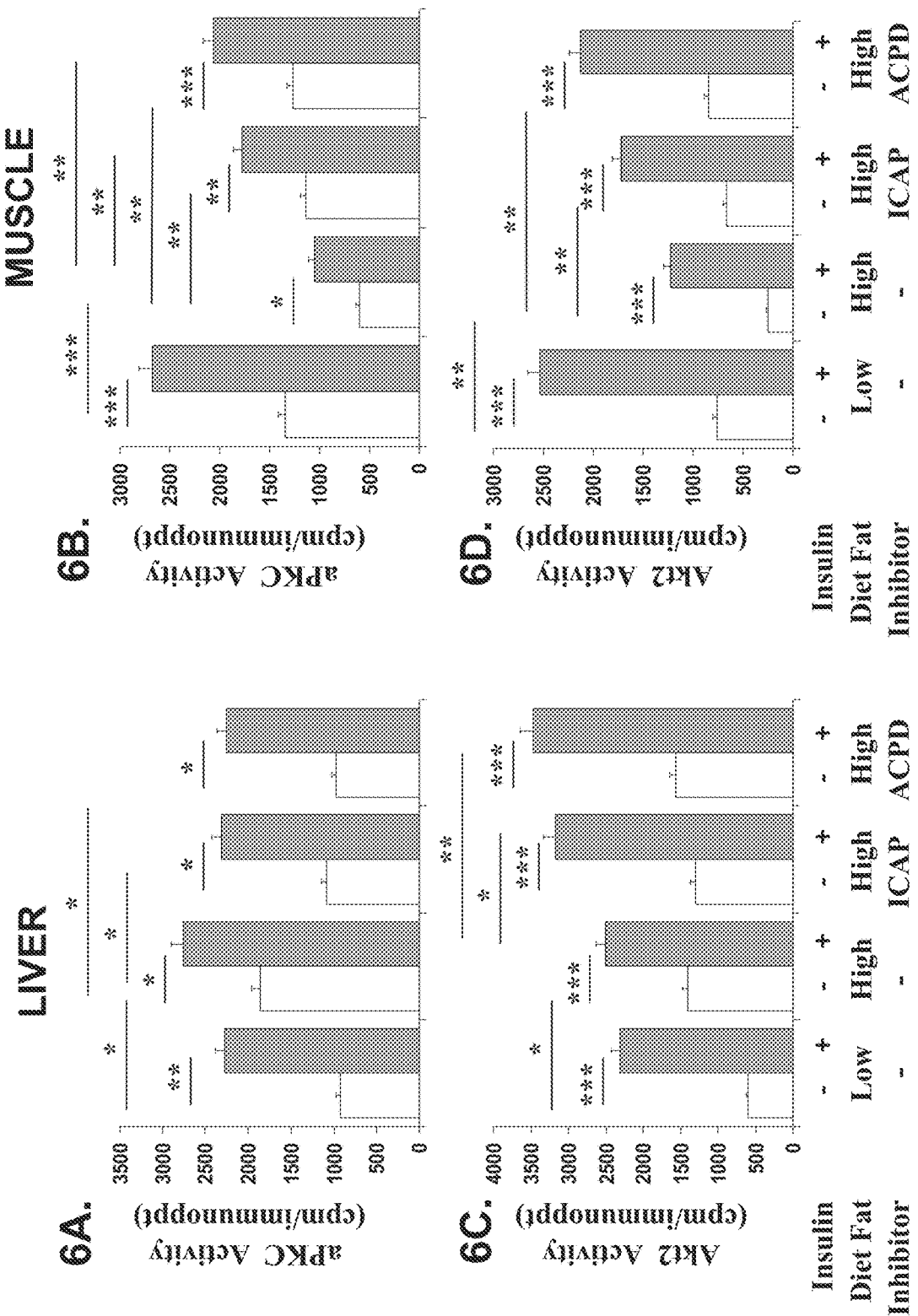

FIGS. 6A-6D show the effect of high fat feeding (HFF) and ICAP or ACPD (s.c. injection of ICAP, 1 mg/kg body weight, or ACPD; 10 mg/kg body weight) on basal and insulin-stimulated activity of aPKC (FIGS. 6A and 6B) and Akt2 (FIGS. 6C and 6D) in muscle (FIGS. 6B and 6D) and liver (FIGS. 6A and 6C). After 10 weeks of feeding a low fat diet (10% calories from fat) or a high fat diet (40% of calories from milk fat) and treatment with or without ICAP or ACPD, as indicated, mice were treated for 15 minutes with insulin (1 U/kg body weight given intraperitoneally) and then killed. Liver and muscle tissues were analyzed for immunprecipitable aPKC or Akt activity. Values are mean±SEM of 6 determinations. Asterisks indicate: *, P<0.05: ; P<0.01; and *, P<0.001.

Figures 7A, 7B, 7C, 7D:
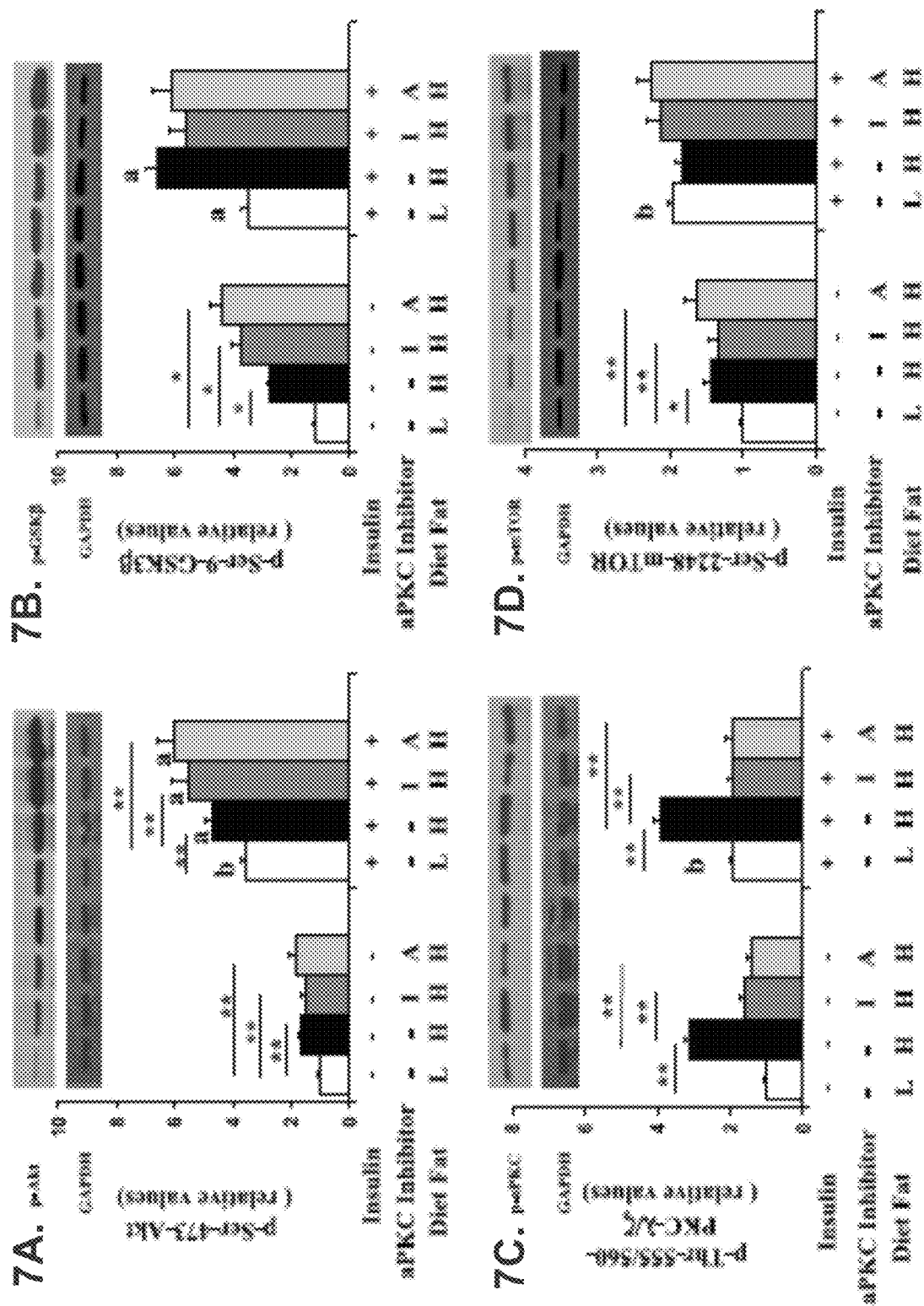
Figures 8A, 8B, 8C, 8D:
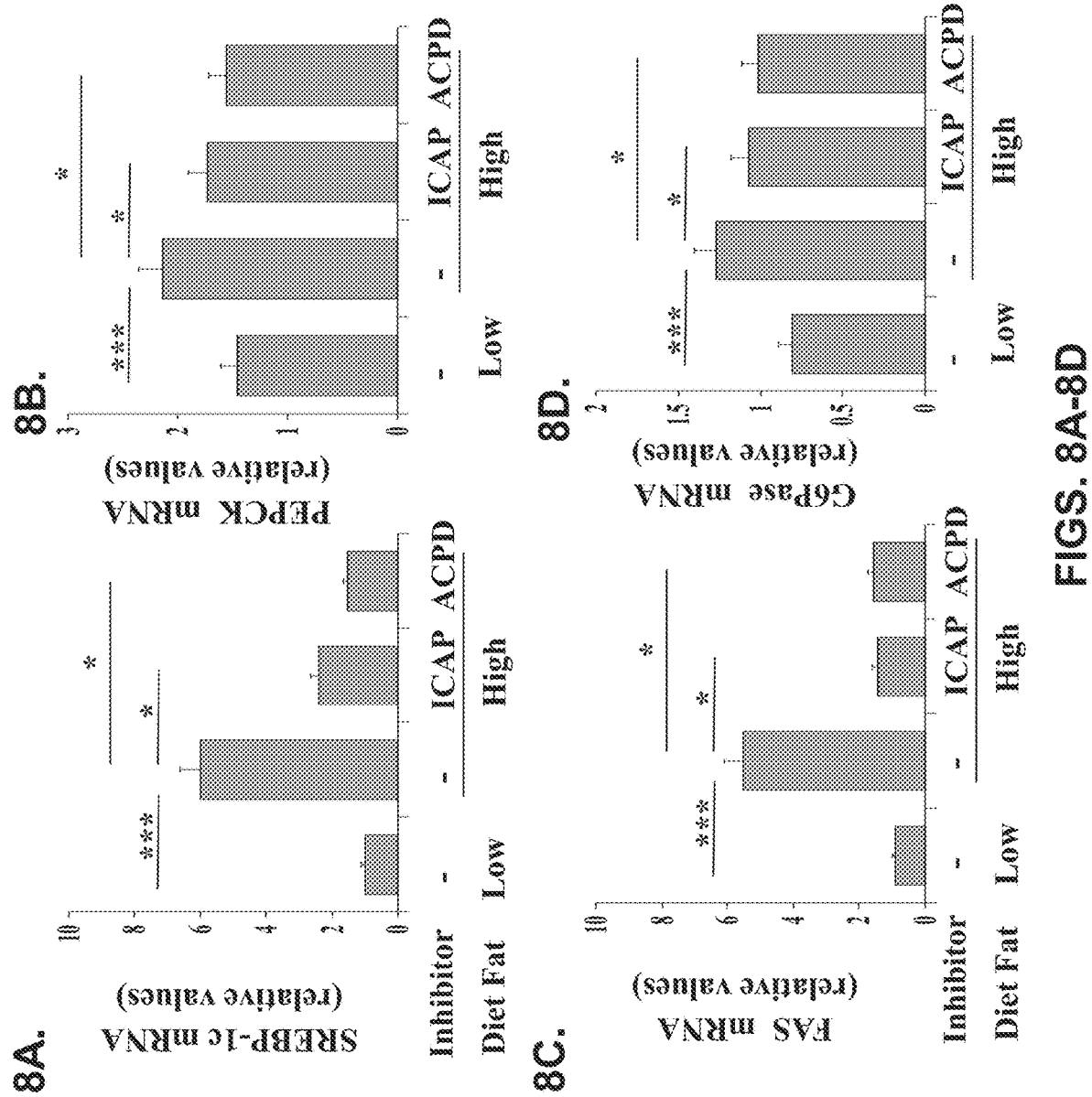

FIGS. 7A-7D demonstrate the effects of HFF diet and ICAP (I) or ACPD (A) on hepatic resting/basal and insulin stimulated phosphorylation of $Ser^{473}$-Akt (FIG. 7A), Ser9-GSK3β (FIG. 7B), $Thr^{555/560}$-PKC-λ/ζ (FIG. 7C), and $Thr^{2448}$-mTOR (FIG. 7D). Over a period of 10 weeks, mice were fed a low-fat (10% of calories from fat) (L) or high-fat (40% of calories from milk fat) (H) diets and treated with or without ICAP or ACPD and fed mice were treated for 15 min before killing with or without insulin (1 unit/kg body weight i.p.). The liver was harvested and examined for immunoreactivity of indicated signaling factors. Bar values are mean±SEM (n=6). *P<0.05; P<0.01; *P<0.001 for indicated comparisons. Letters above bars indicated the following: a, P<0.05; b, P<0.01; c, P<0.001 for insulin-stimulated versus resting/basal values in corresponding treatment groups. Representative immunoblots are shown for indicated phosphor-proteins and GAPDH loading controls FIGS. 8A-8D demonstrate the effects of a HFF diet and ICAP (I) or ACPD (A) on mRNA levels of lipogenic enzymes SREBP-1c (FIG. 8A) and FAS (FIG. 8B), as well as mRNA levels of gluconeogenic enzymes PEPCK (FIG. 8C) and G6Pase (FIG. 8D) in the livers of ad libitum-fed mice. Over a period of 10 weeks, mice consumed low-fat (L) and high-fat (H) diets and treated with or without ICAP or ACPD. After killing, liver tissue was examined for mRNA of the indicated enzymes. Values are means±SEM (n=12). Acute 15 minute insulin treatment prior to killing, as described with respect to FIGS. 7A-7D, did not alter mRNA levels and data is not shown for this treatment group. *P<0.05; P<0.01; *P<0.001 for indicated comparisons.

FIGS. 9A-9D demonstrate the effects of a HFF diet and ICAP (I) or ACPD (A) on immunoreactive protein levels of lipogenic enzymes SREBP-1c (FIG. 9A) and FAS (FIG. 9B), as well as immunoreactive protein levels of gluconeogenic enzymes PEPCK (FIG. 9C) and G6Pase (FIG. 9D) in the livers of ad libitum-fed mice. Over a 10 week period, mice consumed either a low-fat (L) or a high-fat (H) diet and were treated with or without ICAP or ACPD. After killing, liver tissue was examined for immunoreactive protein of the indicated enzymes. Values are means±SEM (n=12). An acute 15-minute insulin treatment, as described with respect to FIGS. 7A-7D, did not alter immunoreactive protein levels. This data is not shown. *P<0.05; P<0.01; *P<0.001 for indicated comparisons. Representative immunoblots are shown for indicated proteins. The levels of the active SREBP-1 c fragment were measured in nuclear preparations.

Figures 10A, 10B, 10C, 10D:
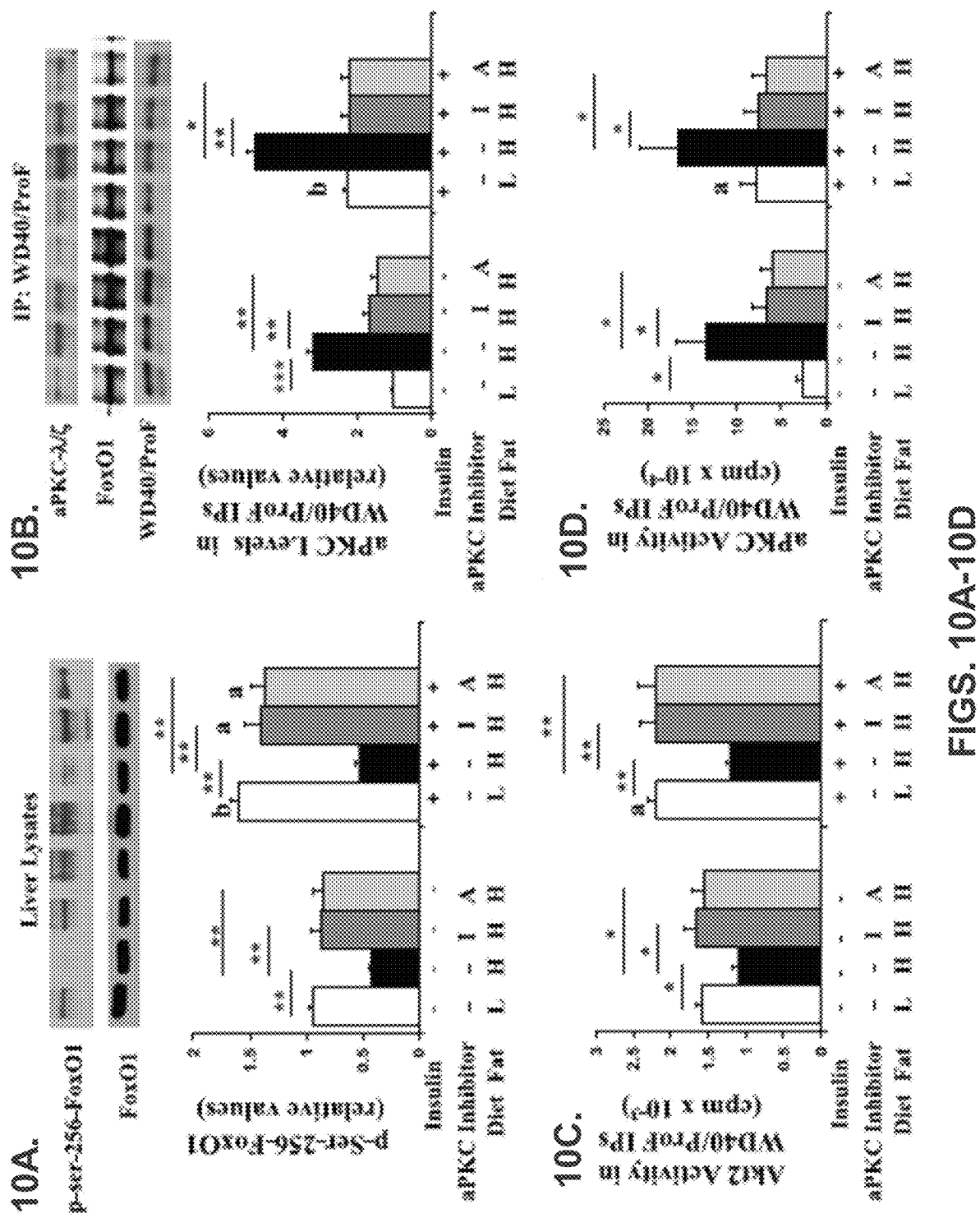

FIGS. 10A-10D demonstrate the effects of a HFF diet and ICAP (I) or ACPD (A) on phosphorylation of Ser256-FoxO1 in liver lysates (FIG. 10A); recovery of immunoreactivity of aPKC, FoxO1, and WD40/ProF in WD40/ProF immunoprecipitates (FIG. 10B); recovery of Akt enzyme activity in WD40/ProF immunoprecipitates (FIG. 10C); and recovery of aPKC enzyme activity in WD40/ProF immunoprecipitates (FIG. 10D). Over a time period of 10 weeks, mice were fed a low-fat (L) or high-fat (H) diet and treated with or without ICAP or ACPD. 15 minutes before killing, mice were treated with or without insulin (1 unit/kg body wt, injected intraperitoneally). The liver was harvested and analyzed for indicated signaling factors in liver lysates or WD40/ProF immunoprecipitates prepared from liver lysates. Bargram values are mean±SEM of six determinations. *P<0.05; P<0.01; *P<0.001 for indicated comparisons. Letters above bars indicate the following: a, P<0.05; b, P<0.01; and c, P<0.001 for insulin-stimulated versus basal/resting values in corresponding treatment groups. FoxO1 and WD40/ProF levels were not altered by treatments. Large amounts of immunoreactive immuno-g globulins precluded accurate measurement of nearby Akt in WD40/ProF immunoprecipitates.

Figures 11A, 11B, 11C, 11D, 11E:
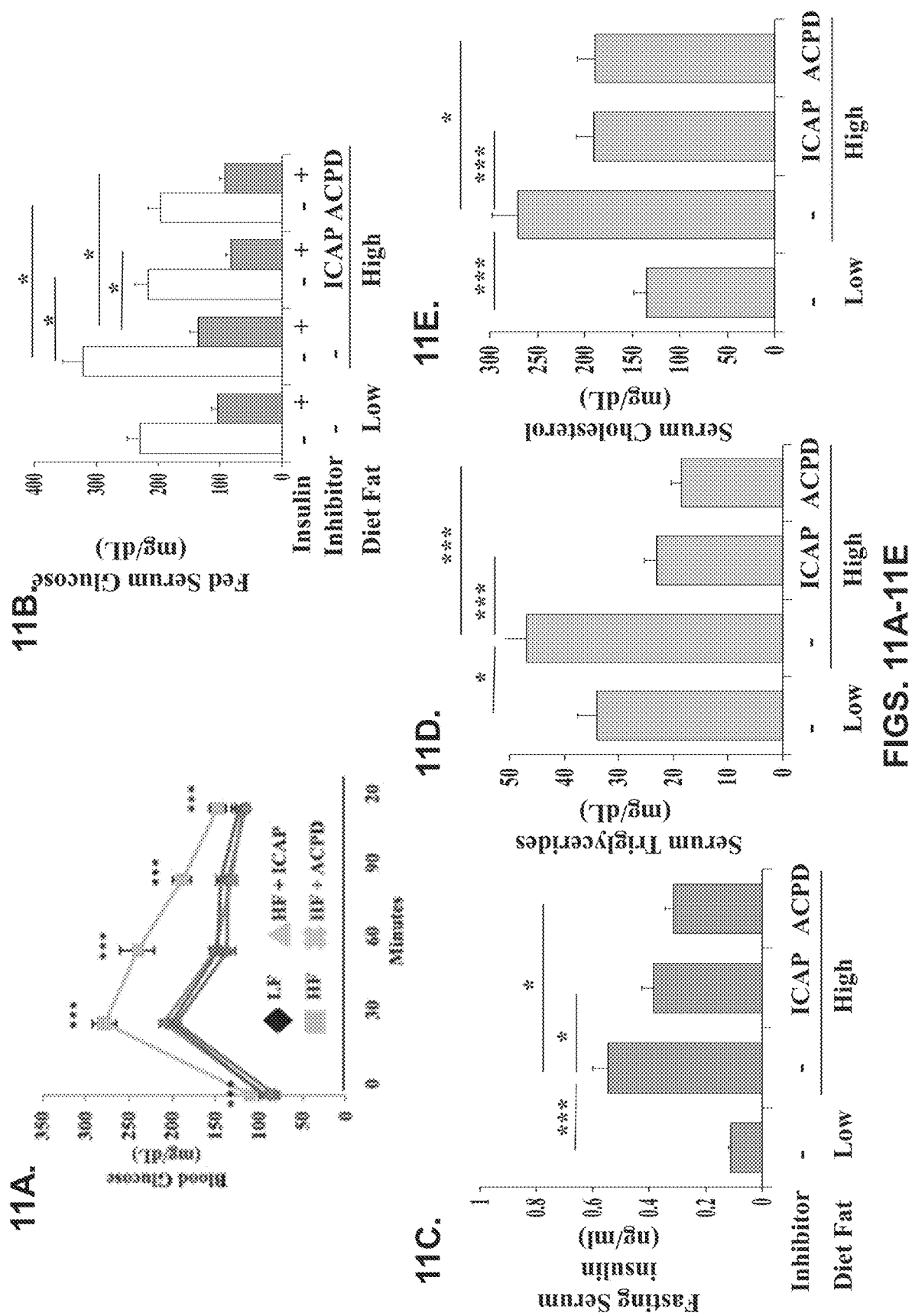

FIGS. 11A-11E show the effects of high fat feeding and ICAP or ACPD on glucose tolerance (FIG. 11A) and serum levels of glucose in fed mice (FIG. 11B), serum insulin in fasted mice (FIG. 11C), serum levels of triglycerides in fed mice (FIG. 11D), and serum levels of cholesterol in fed mice (FIG. 11E). Mice were fed a low fat diet (10% calories from fat) or a high fat diet (40% of calories from milk fat) and simultaneously treated with or without ICAP or ACPD. At 9 weeks of treatment, mice were subjected to an overnight fast followed by glucose tolerance testing (2 mg glucose/kg body weight injected intraperitoneally) with blood glucose levels measured at 0, 30, 60, 90 and 120 minutes. After 10 weeks, mice were injected with or without insulin (1 U/kg body weight given intraperotoneally) and were then killed 15 minutes post injection. Serum was analyzed for insulin, triglycerides and cholesterol. Values are mean±SEM of 12 determinations for glucose tolerance testing, and mean±SEM of 6 determinations for effects of insulin on serum glucose. Asterisks indicate: *, P<0.05: ; P<0.01; and *, P<0.001. Data regarding treatment with insulin is not shown where no significant differences between insulin treated and non-insulin treated mice were observed.

Figures 12A, 12B, 12C, 12D, 12E:
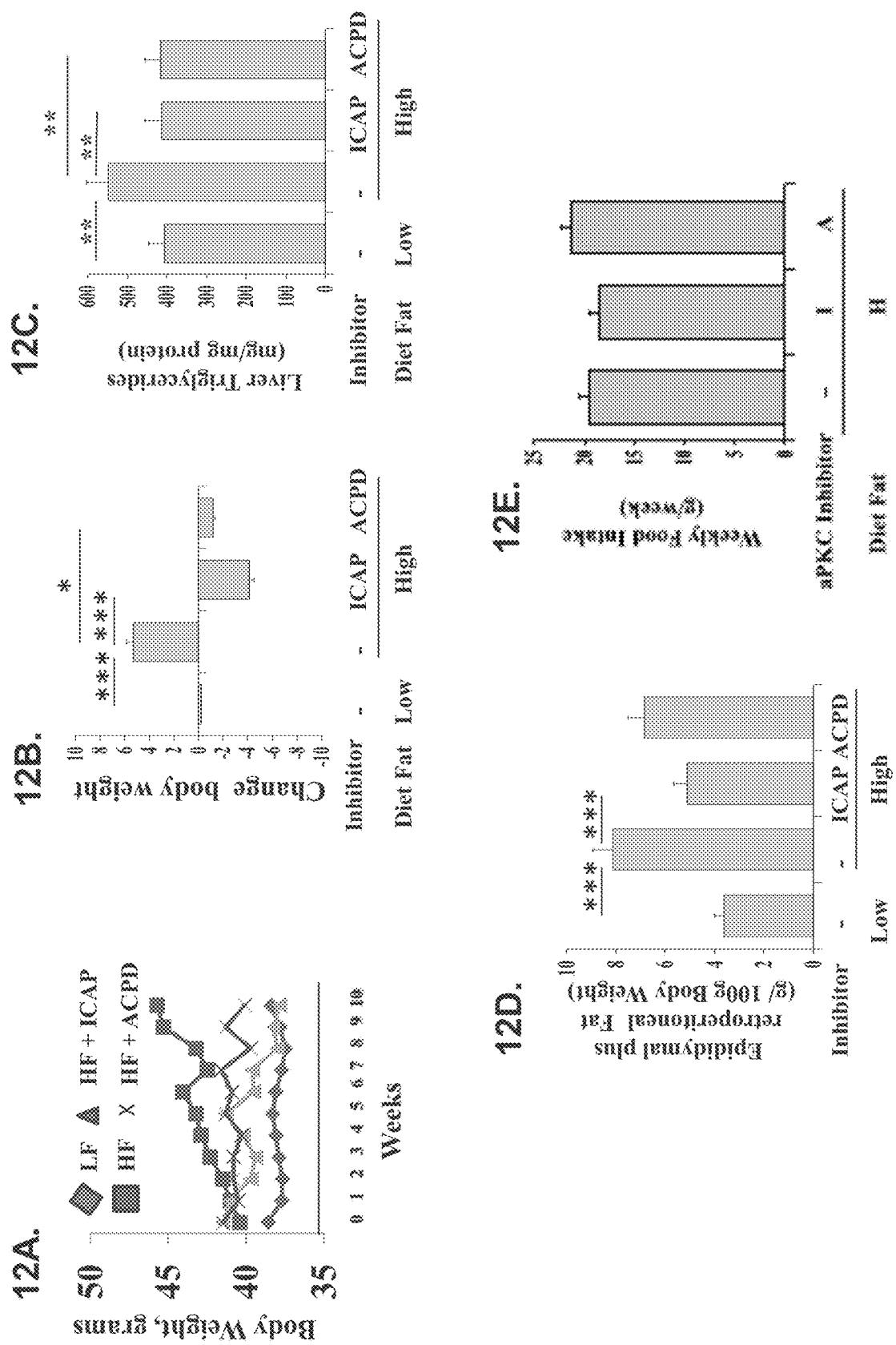

FIGS. 12A-12E show the effects of high fat feeding and ICAP or ACPD on body weight (FIG. 12A), change in body weight (FIG. 12B) levels of hepatic triglycerides (FIG. 12C), weights of epididymal plus retroperitoneal fat pads (FIG. 12D), and weekly food intake (FIG. 12E). Mice were fed a low fat diet (10% calories from fat) or a high fat diet (40% of calories from milk fat) and treated with or without ICAP or ACPD. Body weight and food intake was measured weekly. After 10 weeks, the mice were killed, and tissues were analyzed for indicated parameters. Values are mean±SEM of 12 determinations. Asterisks indicate: *, P<0.05: ; P<0.01; and *, P<0.001.

Figure 13A:
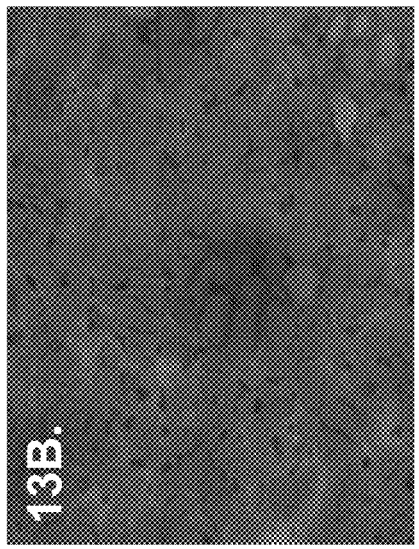
Figure 13B:
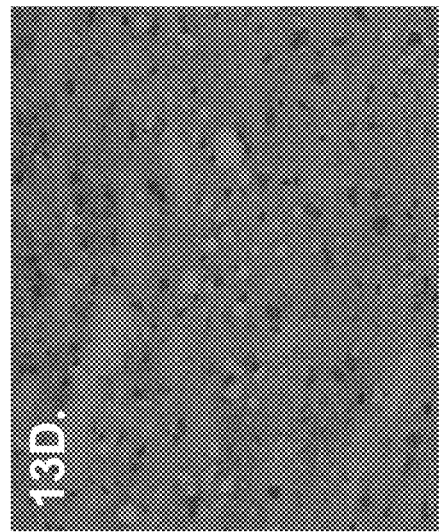
Figure 13C:
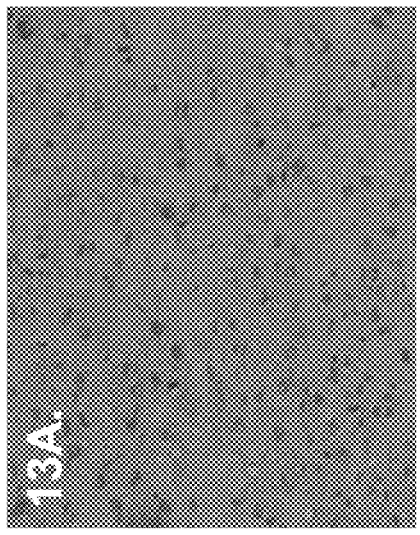
Figure 13D:
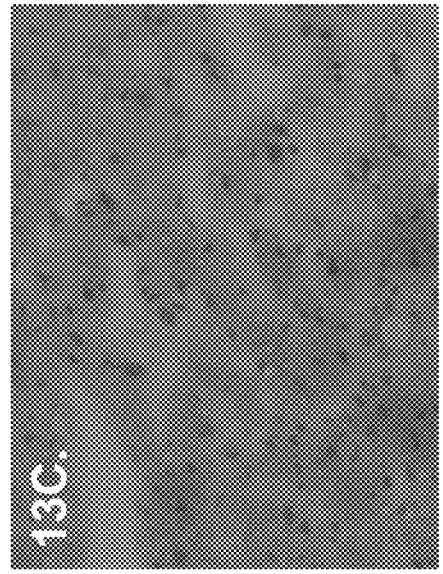

FIGS. 13A-13D demonstrate the effects of an HFF diet and ICAP (I) or ACPD (A) on hepatic fat contents as per Oil Red O staining in mice consuming a low-fat diet (FIG. 13A), a high fat diet (FIG. 13B), a high-fat diet and treated with ICAP (FIG. 13C), and a high fat-diet and treated with ACPD (FIG. 13D). Over a period of 10 weeks, mice were consuming low-fat and high-fat diets and treated with or without ICAP or ACPD.

Figure 14:
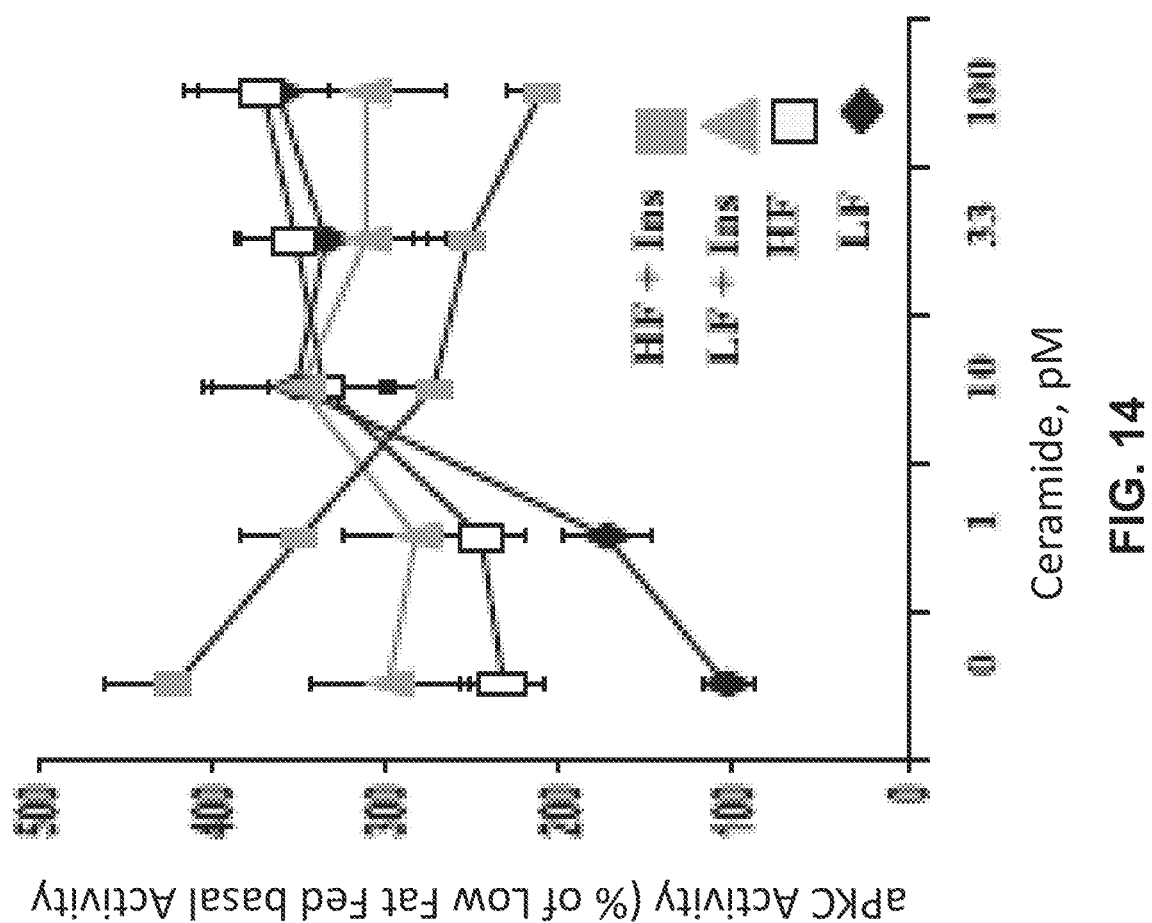

FIG. 14 demonstrates the effects of ceramide on aPKC immunoprecipitated from liver lysates obtained from mice consuming low-fat (LF) and high-fat (HF) diets for 10 weeks and treated with or without insulin (Ins) for 15 min prior to killing, as described in FIGS. 7A-7D (except that these mice were not treated with an aPKC inhibitor). Activity of aPKC with indicated concentrations of ceramide (Sigma) was measured. Values are mean±SEM of three to five determinations.

Figure 15:
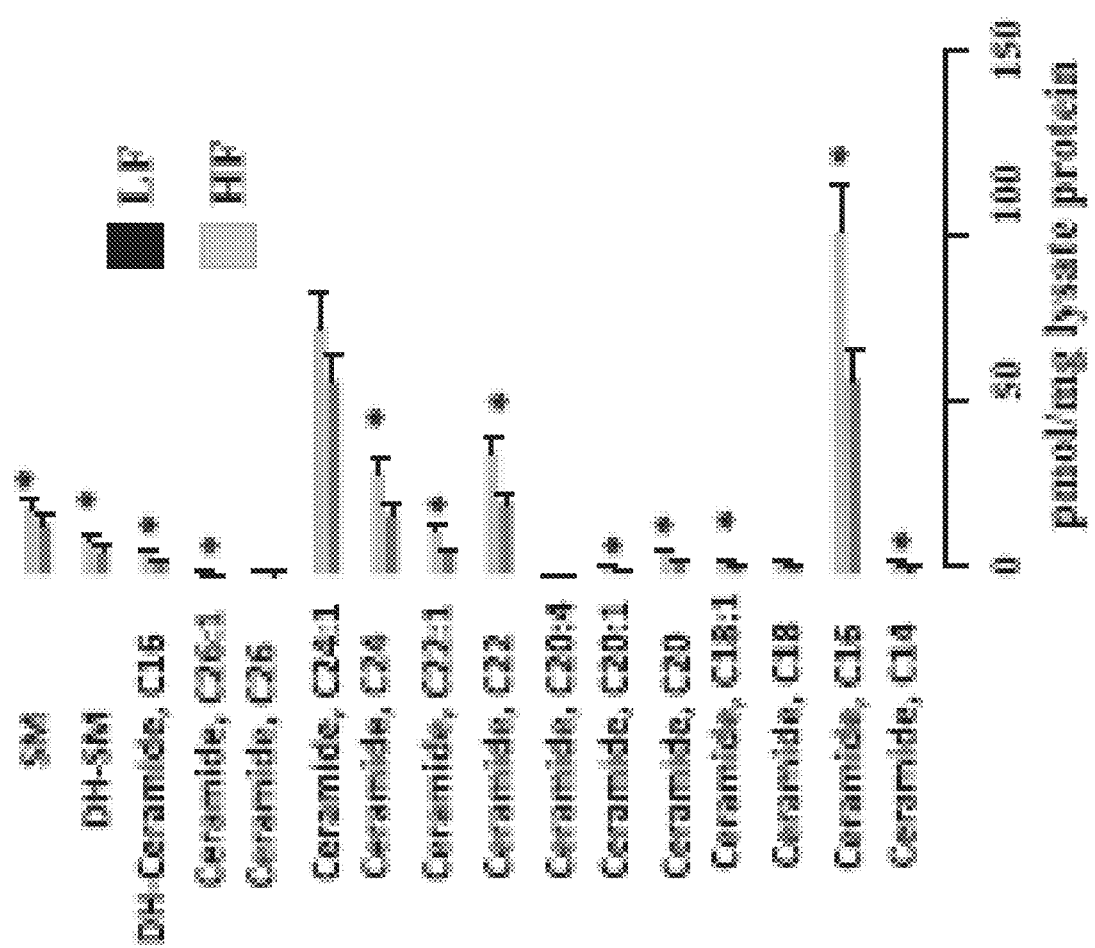

FIG. 15 demonstrates the effects of the feeding of HFF and LFF on hepatic levels of ceramide and sphingomyelin species. Over a period of 10 weeks, mice were fed a low-fat or high-fat diet but were not treated with aPKC inhibitors. Bargram values are mean±SEM of eight determinations. DH, dihydro; SM, sphingomyelin.

FIGS. 16A-16D show basal and insulin-stimulated phosphorylation of aPKC and Akt in liver (FIGS. 16A and 16C) and muscle (FIGS. 16B and 16D) of lean control (ob$^+$) mice and ob/ob mice treated without or with ACPD. Lean control (ob$^+$) mice and ob/ob mice were injected subcutaneously once daily for 10 weeks with saline vehicle or ACPD (10 mg/kg body weight given subcutaneously) in saline vehicle, as indicated, and treated acutely with (+) or without (−) insulin (1 U/kg body weight) for 15 min prior to killing. Tissues were subjected to Western analyses for p-thr555/560-PKC-ι/ζ/λ and p-ser-473-Akt to assess respective kinase activities. Representative blots are shown. Blots are representative of 5-6 determinations.

Figure 17A:
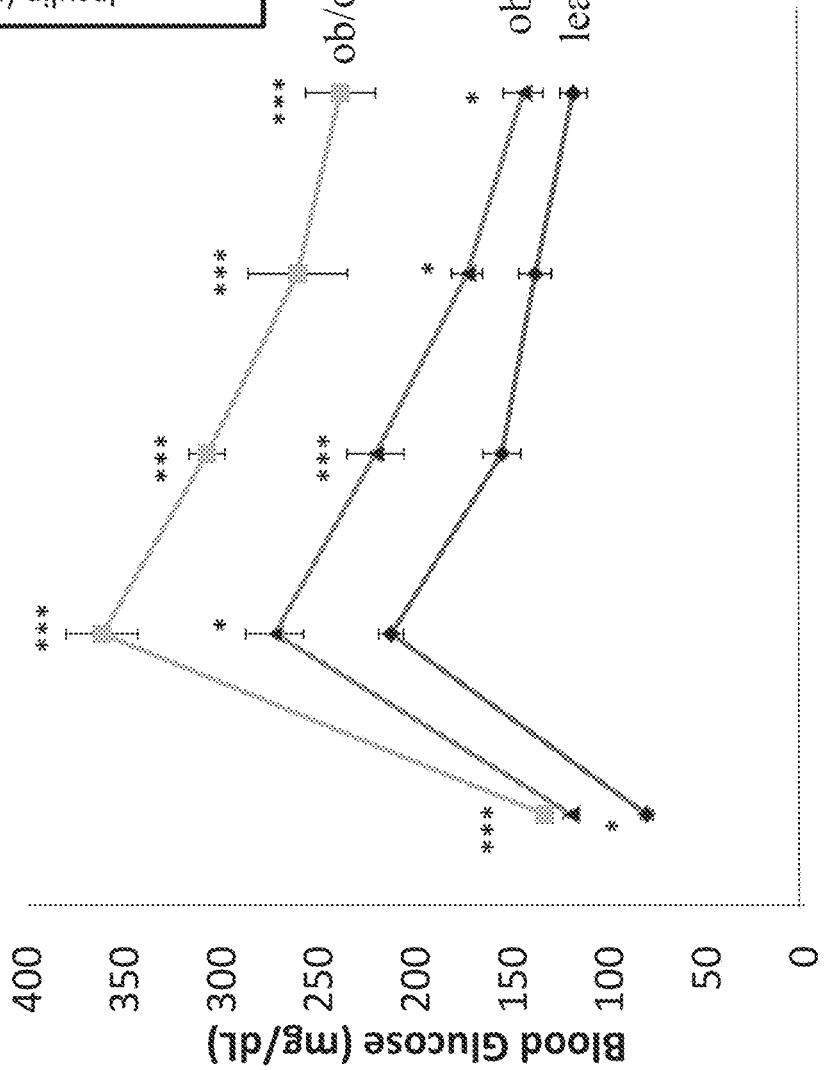
Figure 17B:
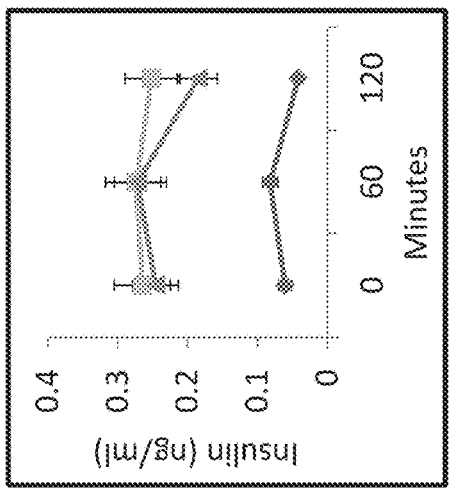

FIGS. 17A-17B show the effects of ACPD on glucose tolerance in ob/ob mice. Lean control (ob$^+$) mice and ob/ob mice were injected subcutaneously once daily for 10 weeks with saline vehicle or ACPD (10 mg/kg body weight given subcutaneously) in saline vehicle, as indicated, and, during the 9$^{th}$ week, after an overnight fast, the mice were subjected to glucose tolerance testing (2 mg glucose/kg body weight administered intraperitoneally). At the indicated times, tail vein blood was obtained for determination of serum levels of glucose (main panel) and insulin (inset). Values are mean±SEM of 10-12 determinations. Asterisks indicate: *, $P<0.05$; , $P<0.01$; and *, $P<0.001$.

FIGS. 18A-18E demonstrate the effect of ACPD on body weight (FIG. 18A), food intake (FIG. 18B), combined weight of epididymal plus retroperitoneal fat depots (FIG. 18C), serum triglycerides (FIG. 18D), and liver triglycerides (FIG. 18E) in ob/ob mice. Mice were treated with ACPD daily for 10 weeks. Insulin treatment 15 minutes prior to killing did not alter triglyceride levels. Values are mean±SEM of (N) determinations. Asterisks: *, $P<0.05$;  $P<0.01$; *, $P<0.001$.

FIGS. 19A-19D demonstrate the effects of ACPD on phosphorylation/activities of pSer$^{473}$-Akt (FIGS. 19A and 19B) and p-Thr$^{556/560}$-PKC-λ/ζ (FIGS. 19C and 19D) in resting/basal and insulin-stimulated conditions and during treatment with an ACPD in liver (FIGS. 19A and 19C) and muscle (FIGS. 19B and 19D) lysates of lean ob$^+$ and obese-phase ob/ob mice. Over 10 weeks, lean ob$^+$ mice and ob/ob mice were injected subcutaneously daily with 0.2 ml physiologic saline or saline containing ACPD (10 mg/kg body weight). Before killing, ad libitum fed mice were treated for 15 min±insulin (1 U/kg body-weight, intraperitoneally). Values are mean±SEM of (N) determinations. Asterisks: *, $P<0.05$: , $P<0.01$; *, $P<0.001$.

FIGS. 20A-20E demonstrates phosphorylation of Akt substrates, FoxO1 (FIG. 20A), mTOR (FIG. 20B) and GSK3β (FIG. 20C). Association of aPKC (FIG. 20D) and Akt (FIG. 20E) with hepatic WD40/ProF in livers of lean ob$^+$ and obese-phase ob/ob mice during resting/basal and insulin-stimulated conditions and during treatment with ACPD is also demonstrated in FIGS. 20A-20E. Mice were treated with ACPD and insulin as in FIGS. 19A-19D. In FIGS. 20A, 20B and 20C, liver lysates were blotted directly. In FIGS. 20D and 20E, WD40/ProF was immunoprecipitated from liver lysates, and portions of immunoprecipitates were blotted. Values are mean±SEM of (N) determinations. Asterisks: *, $P<0.05$: , $P<0.01$; *, $P<0.001$. Representative blots are shown; note unchanged level s of FoxO1 in lysates and WD40/ProF in immunoprecipitates.

FIGS. 21A-21F demonstrate the effects of treatment with aPKC inhibitor, ACPD, on mRNA levels of hepatic SREBP-1c (FIG. 21A), FAS (FIG. 21B), ACC (FIG. 21C), TNF-α (FIG. 21D), PEPCK (FIG. 21E) and G6Pase (FIG. 21F) in obese ob/ob mice. Mice were treated with ACPD and insulin as 19. 15-min insulin treatment did not alter mRNA or protein levels of these enzymes. Values are mean±SEM of (N) determinations. Asterisks: *, $P<0.05$: , $P<0.01$; *, $P<0.001$.

Figure 22:
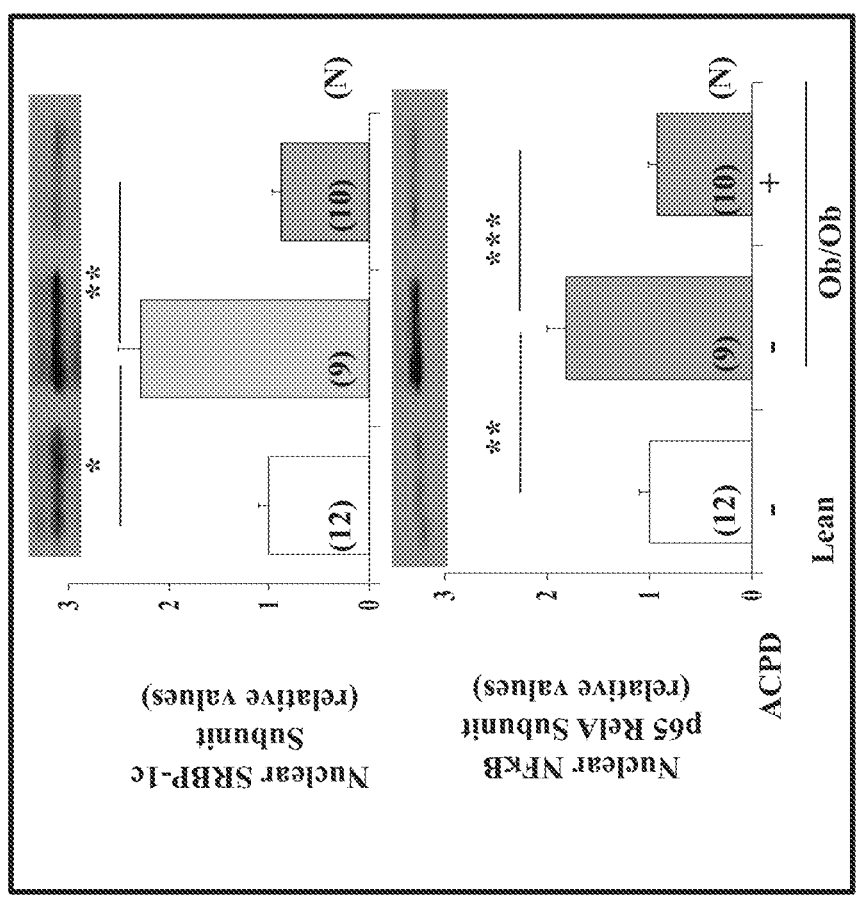
Figures 23A, 23B, 23C, 23D:
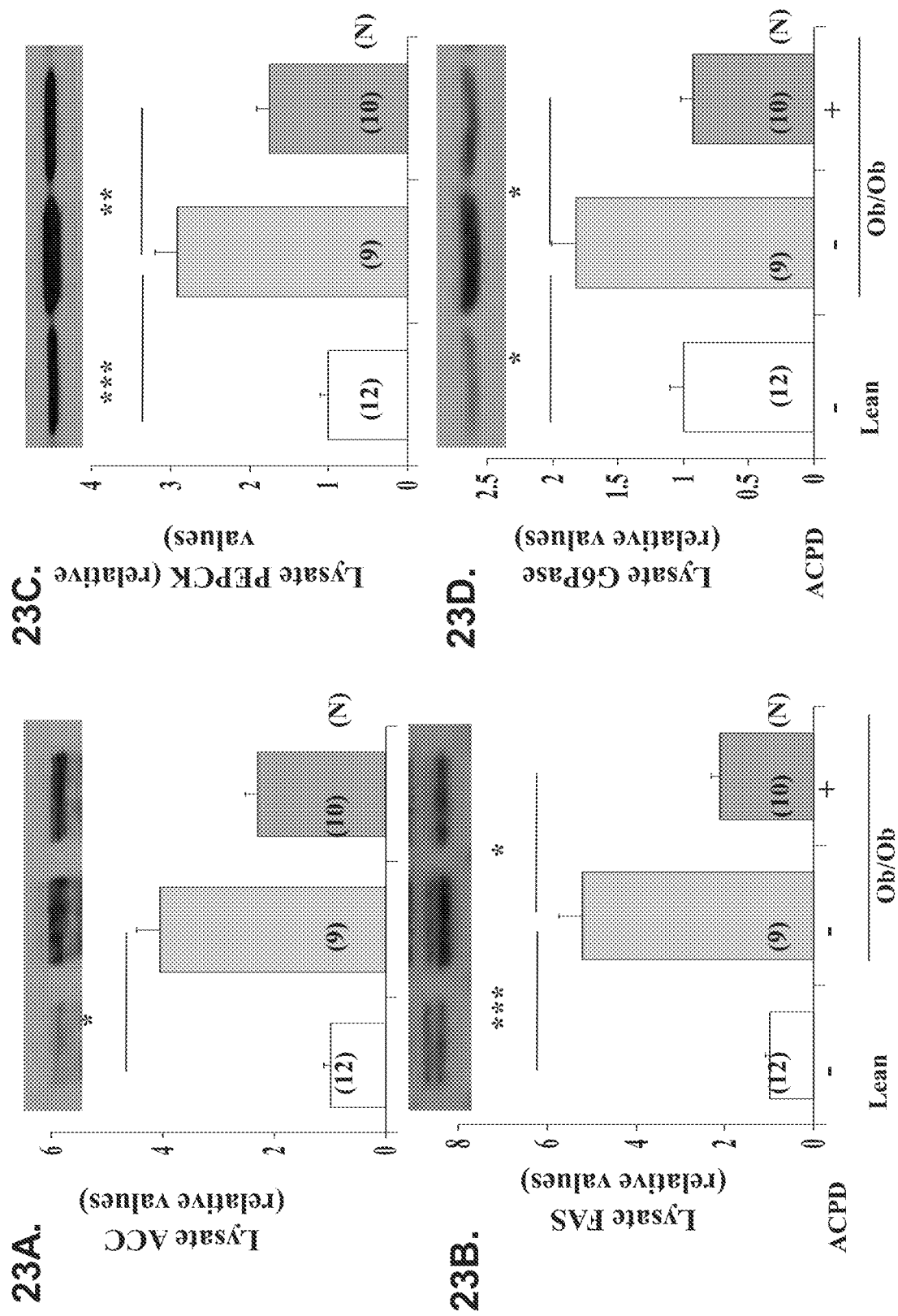

FIG. 22 demonstrates the effects of treatment with aPKC inhibitor, ACPD, on hepatic nuclear levels of the active 60-70 kDa proteolytic fragment of SREBP-1c and the active p65/RelA subunit of NFκB in obese ob/ob mice. Mice were treated with ACPD and insulin prior to killing as previously described 15-min insulin treatment did not alter mRNA or protein levels of these enzymes. Values are mean±SEM of (N) determinations. Asterisks: *, $P<0.05$: , $P<0.01$; *, $P<0.001$. Representative blots are shown.

FIGS. 23A-23D demonstrate the effects of treatment with aPKC inhibitor, ACPD, on hepatic lysate protein levels of ACC (FIG. 23A), FAS (FIG. 23B), PEPCK (FIG. 23C), and G6Pase (FIG. 23D) in obese ob/ob mice. Mice were treated with ACPD and insulin as in FIG. 22. 15-min insulin treatment did not alter mRNA or protein levels of these enzymes. Values are mean±SEM of (N) determinations. Asterisks: *, $P<0.05$: , $P<0.01$; *, $P<0.001$. Representative blots are shown.

Figure 24:
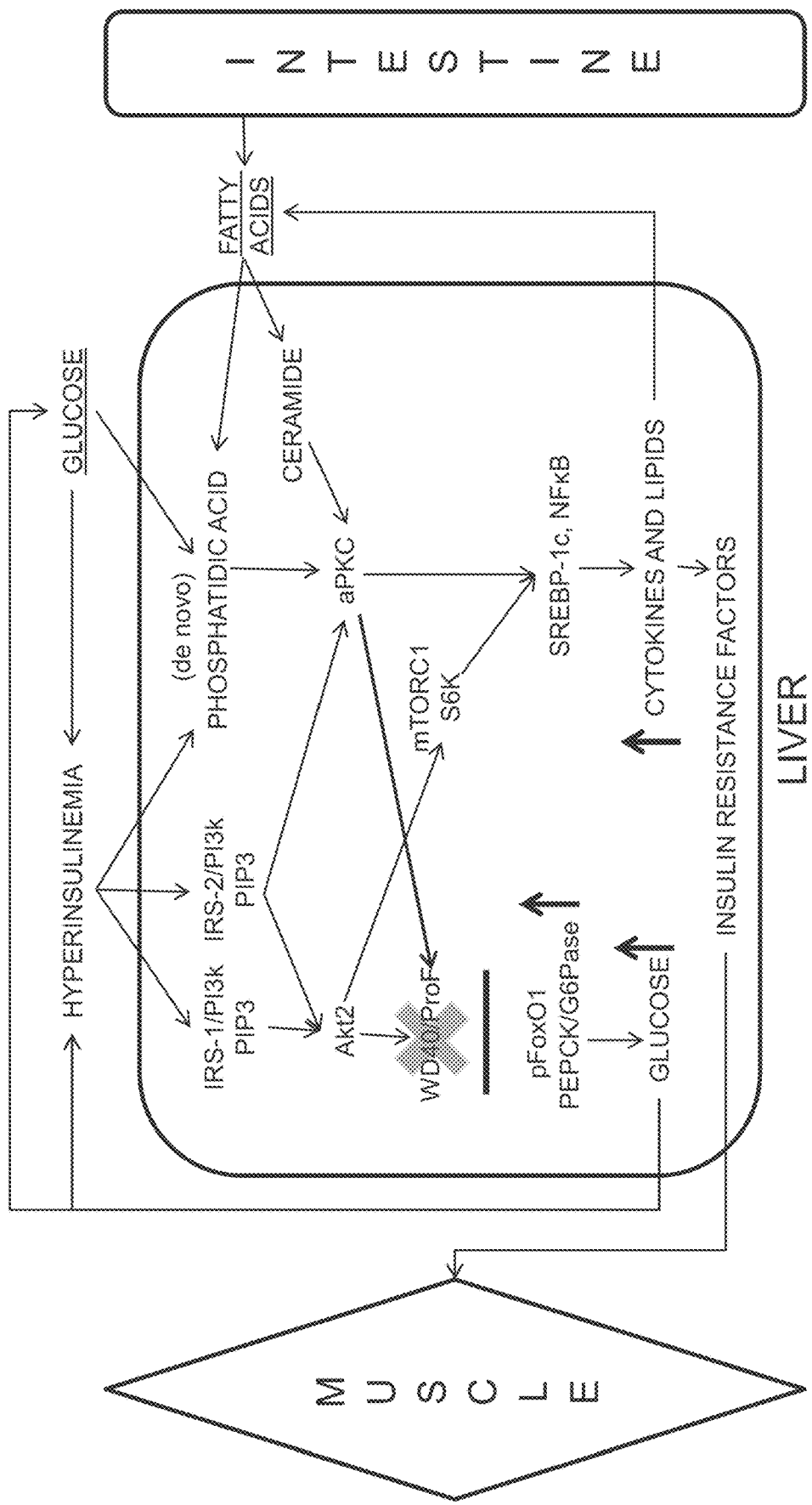

FIG. 24 is a schematic showing factors involved in early development of hepatic insulin resistance in diet-induced obesity.

Figure 25A:
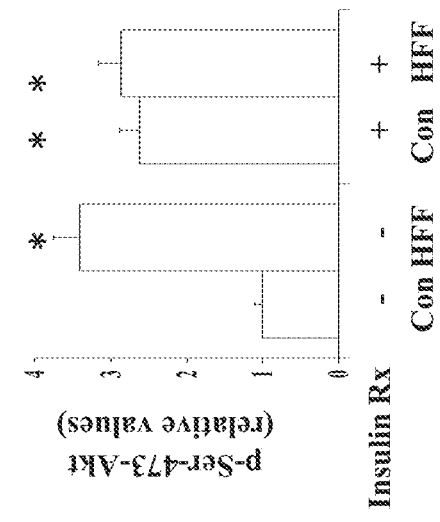
Figure 25B:
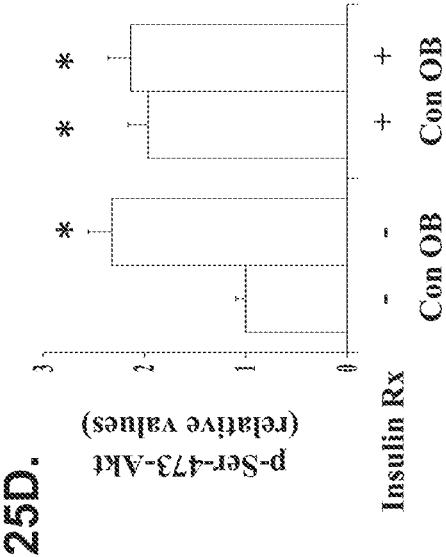
Figure 25C:
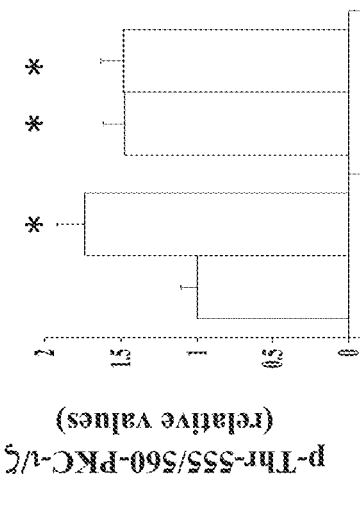
Figure 25D:
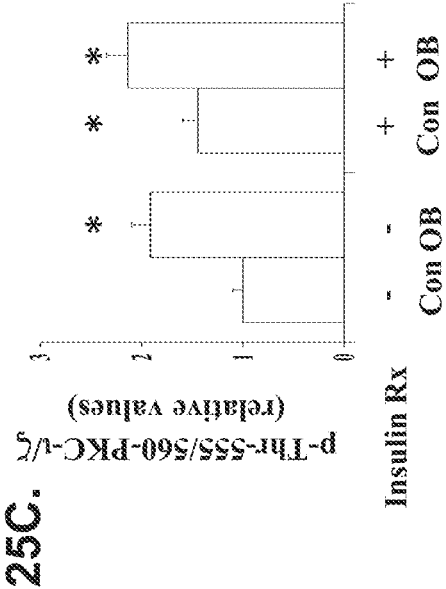

FIGS. 25A-25D demonstrate the resting/basal and insulin-stimulated activities of aPKC (FIGS. 25A and 25C) and Akt2 (FIGS. 25B and 25D) in the brains of control (Con) and high-fat fed (HFF) mice (FIGS. 25A and 25B) and in the brains of control (Con) and ob/ob (OB) mice (FIGS. 25C and 25D). HFF mice were fed a diet containing 40% of calories derived from milk fats and all other mice were fed standard mice chow containing 10% fat. All mice were fed these diets over a 10 week period. Where indicated (+), mice were acutely treated with insulin (1 U/kg body weight) that was administered intraperitoneally 15 minutes prior to killing. Activity/activation was assessed by Western blot analyses of phospho-protein immunoreactivity and quantitative scanning of the blots. The results were normalized to an endogenous control. Values of scans are shown as the mean±SEM of 4-6 determinations. Asterisks indicated $P<0.05$ (as per ANOVA) versus the basal control.

FIGS. 26A-26D demonstrate the resting/basal and insulin-stimulated phosphorylation of Akt substrates FoxO1

Figure 26A:
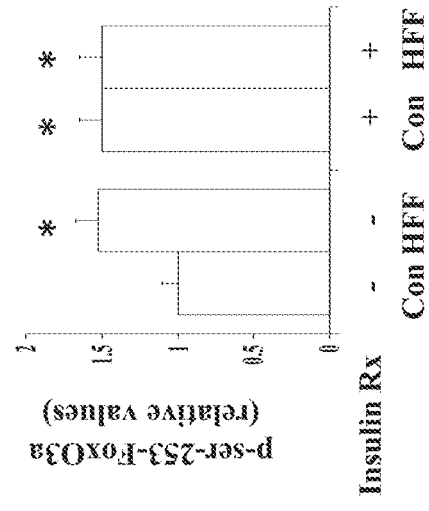
Figure 26B:
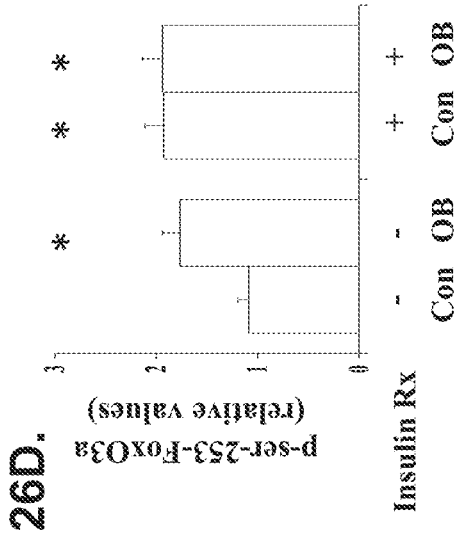
Figure 26C:
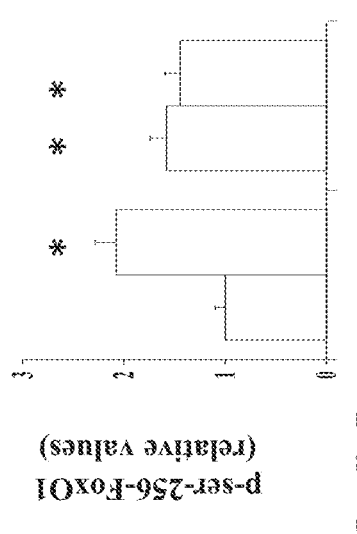
Figure 26D:
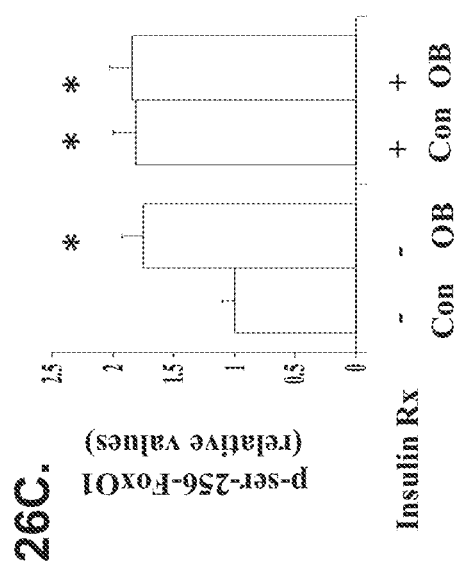

(FIGS. 26A and 26C) and FoxO3a (FIGS. 26B and 26D) in the brains of control (Con) and high-fat fed (HFF) mice (FIGS. 26A and 26B) and in the brains of control (Con) and ob/ob (OB) mice (FIGS. 26C and 26D). HFF mice were fed a diet containing 40% of calories derived from milk fats and all other mice were fed standard mice chow containing 10% fat. All mice were fed these diets over a 10 week period. Where indicated (+), mice were acutely treated with insulin (1 U/kg body weight) that was administered intraperitoneally 15 minutes prior to killing. Levels of phospho-proteins were assessed by Western blot analyses using phospho-peptide-specific antisera followed by quantitative scanning of the blots. The results were normalized to an endogenous control. Values of scans are shown as the mean±SEM of 4-6 determinations. Asterisks indicated P<0.05 (as per ANOVA) versus the basal control.

Figure 27A:
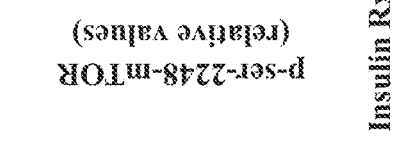
Figure 27B:
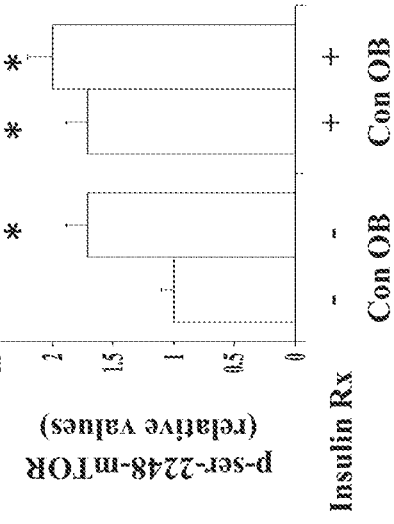
Figure 27C:
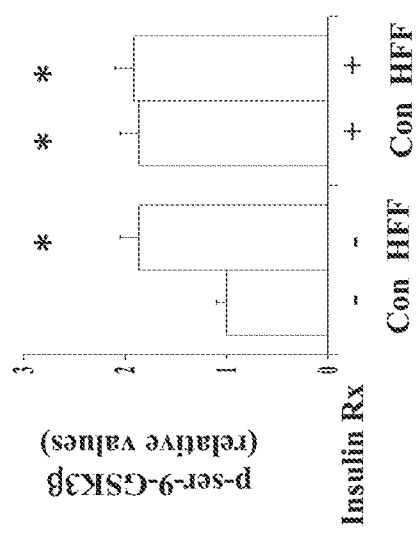
Figure 27D:
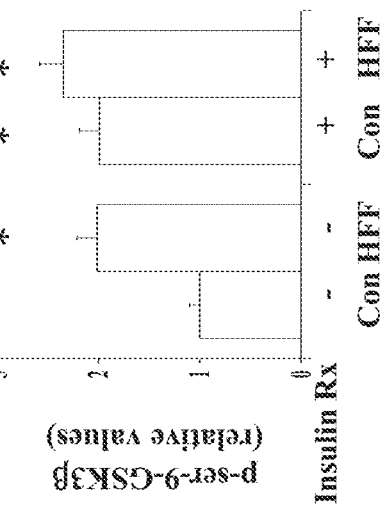

FIGS. 27A-27D demonstrate the resting/basal and insulin-stimulated phosphorylation of Akt substrates GSK3β (FIGS. 27A and 27C) and mTOR (FIGS. 27B and 27D) in the brains of control (Con) and high-fat fed (HFF) mice (FIGS. 27A and 27B) and in the brains of control (Con) and ob/ob (OB) mice (FIGS. 27C and 27D). HFF mice were fed a diet containing 40% of calories derived from milk fats and all other mice were fed standard mice chow containing 10% fat. All mice were fed these diets over a 10 week period. Where indicated (+), mice were acutely treated with insulin (1 U/kg body weight) that was administered intraperitoneally 15 minutes prior to killing. Levels of phospho-proteins were assessed by Western blot analyses using phospho-peptide-specific antisera followed by quantitative scanning of the blots. The results were normalized to an endogenous control. Values of scans are shown as the mean±SEM of 4-6 determinations. Asterisks indicated P<0.05 (as per ANOVA) versus the basal control.

Figure 28:
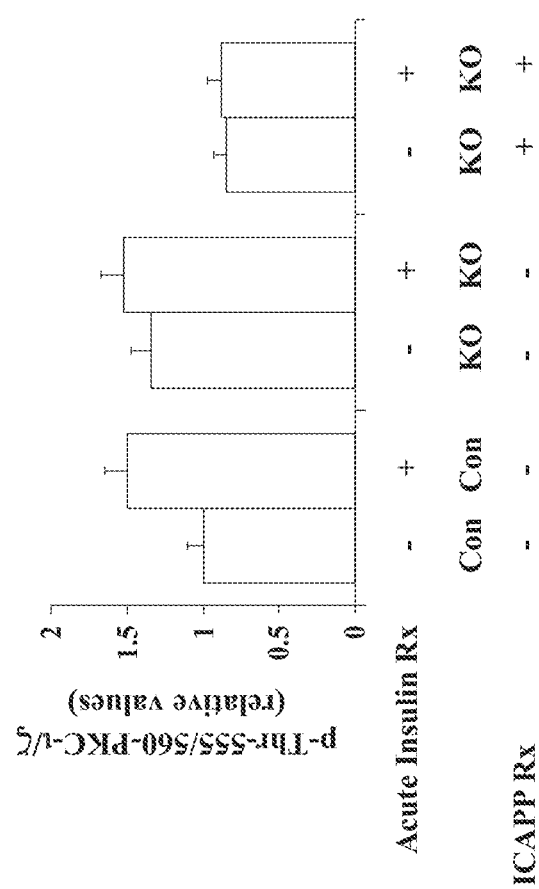

FIG. 28 demonstrates the resting/basal and insulin-stimulated activities of aPKC (in the brains of control (Con) versus heterozygous muscle-specific PKC-λ knockout (KO) mice. All mice were fed standard chow containing 10% fat. Where indicated (+), mice were acutely treated with insulin (1 U/kg body weight) that was administered intraperitoneally 15 minutes prior to killing. Where indicated, mice were treated for 8 days with ICAPP. Activity/activation of aPKC was assessed by Western blot analyses of phospho-protein immunoreactivity followed by quantitative scanning of the blots. The results were normalized to an endogenous control. Values of scans are the mean±SEM of 4-6 determinations. Asterisks indicate P<0.05 (as per ANOVA) versus the basal control.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with side various groups As used herein, "active derivative" and the like means a derivative compound that retains an ability to inhibit or reduce the activity one or more PKCs, PKC-zeta, and PKC-lambda/iota of a subject to which it is administered, as compared uninhibited (or normal PKCs).

As used herein, "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

As used herein, "composition" refers to a combination of an active agent(s) and another compound or composition, inert (for example, a detectable agent or label) or active, such as an adjuvant.

As used herein, "control" is an alternative subject or sample used in an experiment for comparison purposes and included to minimize or distinguish the effect of variables other than an independent variable. A control can be positive or negative.

As used herein, "concentrated" refers to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "diluted" refers to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" refers to a dog, cat, guinea pig, mouse, rat, rabbit, ferret, and the like. The term "farm animal" refers to a horse, sheep, goat, chicken, pig, cow, donkey, llama, alpaca, turkey, and the like.

As used interchangeably herein, "biocompatible" and "biologically compatible" refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments, a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

As used herein, "therapeutic" refers to curing or treating a symptom of a disease or condition.

As used herein, "preventative," "preventing," "prevent" and the like refer to partially or completely delaying or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms.

As used herein, "mitigate" refers to reducing a particular characteristic, symptom, or other biological or physiological parameter associated with a disease or disorder.

As used herein, "separated" refers to the state of being physically divided from the original source or population such that the separated compound, agent, particle, chemical compound, or molecule can no longer be considered part of the original source or population.

As used herein, "tangible medium of expression" refers to a medium that is physically tangible and is not a mere abstract thought or an unrecorded spoken word. Tangible medium of expression includes, but is not limited to, words on a cellulosic or plastic material or electronic data stored on a suitable device such as a flash memory or CD-ROM.

As used herein, "about," "approximately," and the like, when used in connection with a numerical variable, generally refers to the value of the variable and to all values of the variable that are within the experimental error (e.g., within the 95% confidence interval for the mean) or within +−10% of the indicated value, whichever is greater.

As used herein, "synergistic effect," "synergism," or "synergy" refers to an effect arising between two or more molecules, compounds, substances, factors, or compositions that that is greater than or different from the sum of their individual effects.

As used herein, "additive effect" refers to an effect arising between two or more molecules, compounds, substances, factors, or compositions that is equal to or the same as the sum of their individual effects.

As used herein, "mammal" refers to any animal classified as a mammal, including a human, domestic and farm animals, nonhuman primates, and zoo, sports, or pet animals, such as dogs, horses, cats, cows, etc.

As used herein, "pharmaceutically acceptable" refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

The terms "sufficient" and "effective," as used interchangeably herein, refer to an amount (e.g. mass, volume, dosage, concentration, and/or time period) needed to achieve one or more desired result(s). For example, a therapeutically effective amount refers to an amount needed to achieve one or more therapeutic effects.

As used herein, "pharmaceutically acceptable carrier or excipient" refers to a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used herein also includes both one and more than one such carrier or excipient. Pharmaceutically acceptable carriers include, but are not limited to, diluents, preservatives, binders, lubricants, disintegrators, swelling agents, fillers, stabilizers, and combinations thereof.

As used herein, "pharmaceutically acceptable salts" refers to any acid or base addition salt whose counter-ions are non-toxic to the subject to which they are administered in pharmaceutical doses of the salts. Specific examples of pharmaceutically acceptable salts are known to those of ordinary skill in the art.

As used herein, "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, "suitable substituent" means a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, C1-C6 alkyl, C2-C6 alkenyl, C1-C6 haloalkyl, C1-C6 alkoxy, C1-C6 haloalkoxy, C2-C6 alkynyl, C3-C8 cycloalkenyl, (C3-C8 cycloalkyl)C1-C6 alkyl, (C3-C8 cycloalkyl)C2-C6 alkenyl, (C3-C8 cycloalkyl) C1-C6 alkoxy, C3-C7 heterocycloalkyl, (C3-C7 heterocycloalkyl) C1-C6 alkyl, (C3-C7 heterocycloalkyl)C2-C6 alkenyl, (C3-C7 heterocycloalkyl)C1-C6 alkoxyl, hydroxy, carboxy, oxo, sulfanyl, C1-C6 alkylsulfanyl, aryl, heteroaryl, aryloxy, heteroaryloxy, aralkyl, heteroaralkyl, aralkoxy, heteroaralkoxy, nitro, cyano, amino, C1-C6 alkylamino, di-(C1-C6 alkyl) amino, carbamoyl, (C1-C6 alkyl)carbonyl, (C1-C6 alkoxy) carbonyl, (C1-C6 alkyl)aminocarbonyl, di-(C1-C6 alkyl) aminocarbonyl, arylcarbonyl, aryloxycarbonyl, (C1-C6 alkyl)sulfonyl, and arylsulfonyl. The groups listed above as suitable substituents are as defined hereinafter except that a suitable substituent may not be further optionally substituted.

As used herein, "optically substituted" indicates that a group may be unsubstituted or substituted with one or more substituents as defined herein.

The term "alkyl" refers to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl has 30 or fewer carbon atoms in its backbone (e.g., $C_1$-$C_{30}$ for straight chains, and $C_3$-$C_{30}$ for branched chains). In other embodiments, a straight chain or branched chain alkyl contains 20 or fewer, 15 or fewer, or 10 or fewer carbon atoms in its backbone. Likewise, in some embodiments cycloalkyls have 3-10 carbon atoms in their ring structure. In some of these embodiments, the cycloalkyl have 5, 6, or 7 carbons in the ring structure.

The term "alkyl" (or "lower alkyl") as used herein is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl," as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy," as used herein, refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

The terms "amine" and "amino" (and its protonated form) are art-recognized and refer to both unsubstituted and substituted amines, e.g., a moiety that can be represented by the general formula:

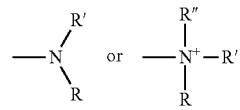

wherein R, R', and R" each independently represent a hydrogen, an alkyl, an alkenyl, —$(CH2)_m$-$R_C$ or R and R' taken together with the N atom to which they are attached complete a heterocycle having from 4 to 8 atoms in the ring structure; $R_C$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

The term "amido" is art-recognized as an amino-substituted carbonyl and includes a moiety that can be represented by the general formula:

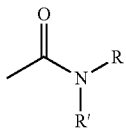

wherein R and R' are as defined above.

As used herein, "Aryl" refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

The term "aralkyl," as used herein, refers to an alkyl group substituted with an aryl group (e.g., an aromatic or heteroaromatic group).

The term "aralkyloxy" can be represented by —O-aralkyl, wherein aralkyl is as defined above.

The term "carbocycle," as used herein, refers to an aromatic or non-aromatic ring(s) in which each atom of the ring(s) is carbon.

"Heterocycle" or "heterocyclic," as used herein, refers to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbonyl" is art-recognized and includes such moieties as can be represented by the general formula:

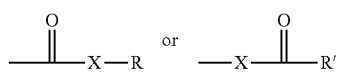

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

The term "heteroatom" as used herein means an atom of any element other than carbon or hydrogen. Exemplary heteroatoms include, but are not limited to, boron, nitrogen, oxygen, phosphorus, sulfur, silicon, arsenic, and selenium.

As used herein, the term "nitro" refers to —NO$_2$; the term "halogen" designates—F, —Cl, —Br, or —I; the term "sulfhydryl" refers to —SH; the term "hydroxyl" refers to —OH; and the term "sulfonyl" refers to —SO$_2$—.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C$_3$-C$_{20}$ cyclic, substituted C$_3$-C$_{20}$ cyclic, heterocyclic, substituted heterocyclic, amino acid, peptide, and polypeptide groups.

Heteroatoms, such as nitrogen, may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "effective amount" refers to the amount of an aPKC inhibitor or derivative thereof described herein that will elicit the biological or medical response of a tissue, system, animal, or human that is being sought by the researcher, veterinarian, medical doctor or other clinician. "Effective amount" includes that amount of an aPKC inhibitor or derivative thereof described herein that, when administered, is sufficient to prevent development of, alleviate to some extent, one or more of the symptoms of an atypical protein kinase C enzyme (aPKC) abnormality being treated. The effective amount will vary depending on the exact chemical structure of the aPKC inhibitor or derivative thereof, the severity of the aPKC abnormality, the route of administration, the time of administration, the rate of excretion, the drug combination, the judgment of the treating physician, the dosage form, and the age, weight, general health, sex and/or diet of the subject to be treated.

The terms "treat," "treating," "treatment," and grammatical variations thereof as used herein include partially or completely delaying, alleviating, mitigating or reducing the intensity of one or more attendant symptoms of a disorder or condition such as an atypical protein kinase C enzyme abnormality and/or alleviating, mitigating or impeding one or more causes of a disorder or condition such as an atypical protein kinase C enzyme abnormality. Treatments according to the embodiments disclosed herein may be applied preventively, prophylactically, palliatively, or remedially. In some instances, the terms "treat," "treating," "treatment," and grammatical variations thereof include partially or completely reducing a condition or symptom associated with an atypical protein kinase C enzyme abnormality as compared with prior to treatment of the subject or as compared with the incidence of such condition or symptom in a general or study population.

As used herein, "about," "approximately," and the like, when used in connection with a numerical variable, generally refers to the value of the variable and to all values of the variable that are within the experimental error (e.g., within the 95% confidence interval for the mean) or within .+−.10% of the indicated value, whichever is greater.

As used herein, "dosage form" or "unit dosage form" refers to a pharmaceutical formulation that is administered to a subject in need of treatment and generally may be in the form of tablets, capsules, sachets containing powder or granules, liquid solutions or suspensions, patches, and the like.

As used herein, "aPKC abnormality" refers to any symptom, condition, disease, disorder, syndrome that involves aberrant aPKC activity or function. Examples include but are not limited to, obesity, insulin resistance, glucose intolerance, hyperinsulinemia, any form of diabetes, weight gain, metabolic syndrome, Alzheimer's disease, hepatosteatosis, non-alcoholic cirrhosis, hypertriglyceridemia, hypercholesterolemia, polycystic ovary disease, and any disorder, disease, condition, or symptom arising from local or systemic hyperinsulinemia and/or metabolic syndrome that arise from abnormal or aberrant aPKC activity or function, including but not limited to, brain disorders such as Alzheimer's disease and cardiovascular diseases and disorders.

Discussion

Insulin-resistant states of obesity, metabolic syndrome, and type 2 diabetes mellitus (T2DM) are pandemic in Western societies. Insulin resistance implies an impairment in glucose metabolism that initially increases insulin secretion. There is no cure for insulin-resistant states of obesity, metabolic syndrome, or T2DM. However, diet, exercise, and weight loss may help alleviate symptoms. When these fail, many of these individuals rely on insulin therapy or other therapeutic compounds, many of which have harsh side effects, to regulate blood glucose levels. As such, there exists a need for improved treatments for insulin-resistant states of obesity, metabolic syndrome, and T2DM.

Protein kinase C (PKC) enzymes are involved in regulating gluconeogenesis and lipogenesis and therefore play a role in overall glucose metabolism and insulin sensitivity. In particular, as shown in FIG. 24, aPKC plays a key role in the development of hepatic and secondary systemic insulin resistance in dietary-induced obesity. In response to dietary excess, availability of lipids that directly activate aPKC, e.g., ceramide and phosphatidic acid, increases. Subsequent activation of hepatic aPKC increases binding of aPKC to ProF, a scaffolding protein that couples Akt and FoxO1, and this leads to impaired ability of Akt2 to phosphorylate FoxO1 on $Ser^{256}$; as a result, expression of PEPCK and G6Pase and hepatic glucose output increase. Ensuing increases in blood glucose levels stimulate insulin secretion, and both glucose and insulin, as well as fatty acids, increase phosphatidic acid production via the de novo pathway. Increased insulin secretion activates hepatic Akt2, as well as aPKC, which together increase hepatic lipid production, thereby providing more substrates for phosphatidic acid and ceramide synthesis. In short, a vicious cycle is set up for lipid production and aPKC activation. This cycle is abetted in human (but not rodent) liver by virtue of the fact that increased aPKC activity provokes increases in levels of PKC-ι mRNA and protein. As a by-product of increases in circulating levels of liver-derived lipids and cytokines, insulin signaling in muscle and certain other tissues (e.g., adipose tissue) is impaired, adding further to diminished glucose disposal and systemic insulin resistance.

As demonstrated herein, atypical PKC (aPKC) inhibitors act to counter aPKC abnormalities, which dysregulate hepatic and secondary insulin sensitivity through altering the pathways involved in gluconeogenesis and lipogenesis. For example, aPKC inhibitors reduce dietary induced obesity. With that in mind, provided herein are compounds and pharmaceutical formulations for treating an atypical protein kinase C enzyme abnormality. In some instances the aPKC abnormality results in a disease or condition, such as insulin-resistant obesity, metabolic syndrome, or diabetes (including T2DM and Type 1).

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

aPKC Inhibitors and Formulations Thereof

Provided herein are aPKC inhibitors and formulations thereof. An "aPKC inhibitor," as used herein, refers generally to a molecule that can bind to PKC and/or PKC ζ/ι and inhibit or reduce the ability of the PKC to function relative to a non-inhibited (normal or wild-type) PKC. aPKC inhibitors include derivatives, including but not limited to active derivatives, of the aPKC inhibitors described herein. In some embodiments, the aPKC inhibitor or derivative thereof contains one or more suitable substituents.

aPKC Inhibitors

The aPKC inhibitor can have a structure according to Formula I or a derivative thereof:

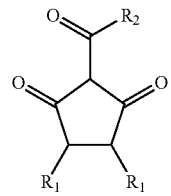

Formula I wherein $R_1$ are each independently selected from the following: hydrogen, halo, C1-C6 alkyl, C2-C6 alkenyl, C1-C6 haloalkyl, C1-C6 alkoxy, C1-C6 haloalkoxy, C2-C6 alkynyl, C3-C8 cycloalkenyl, (C3-C8 cycloalkyl)C1-C6 alkyl, (C3-C8 cycloalkyl)C2-C6 alkenyl, (C3-C8 cycloalkyl) C1-C6 alkoxy, C3-C7 heterocycloalkyl, (C3-C7 heterocycloalkyl)C1-C6 alkyl, (C3-C7 heterocycloalkyl) C2-C6 alkenyl, (C3-C7 heterocycloalkyl)C1-C6 alkoxyl, hydroxy, carboxy, oxo, sulfanyl, C1-C6 alkylsulfanyl, aryl, heteroaryl, aryloxy, heteroaryloxy, aralkyl, heteroaralkyl, aralkoxy, heteroaralkoxy, nitro, cyano, amino, C1-C6 alkylamino, di-(C1-C6 alkyl)amino, carbamoyl, (C1-C6 alkyl) carbonyl, (C1-C6 alkoxy)carbonyl, (C1-C6 alkyl)aminocarbonyl, di-(C1-C6 alkyl)aminocarbonyl, arylcarbonyl, aryloxycarbonyl, (C1-C6 alkyl)sulfonyl, and arylsulfonyl, and wherein $R_2$ is selected from the following: hydrogen, halo, C1-C6 alkyl, tert-butyl, C2-C6 alkenyl, C1-C6 haloalkyl, C1-C6 alkoxy, C1-C6 haloalkoxy, C2-C6 alkynyl, C3-C8 cycloalkenyl, (C3-C8 cycloalkyl)C1-C6 alkyl, (C3-C8 cycloalkyl)C2-C6 alkenyl, (C3-C8 cycloalkyl) C1-C6 alkoxy, C3-C7 heterocycloalkyl, (C3-C7 heterocycloalkyl) C1-C6 alkyl, (C3-C7 heterocycloalkyl)C2-C6 alkenyl, (C3-C7 heterocycloalkyl)C1-C6 alkoxyl, hydroxy, carboxy, oxo, sulfanyl, C1-C6 alkyl furan, C2-C6 alkenyl furan, C1-C6 alkylsulfanyl, aryl, heteroaryl, aryloxy, heteroaryloxy, aralkyl, heteroaralkyl, aralkoxy, heteroaralkoxy, nitro, cyano, amino, C1-C6 alkylamino, di-(C1-C6 alkyl)amino, carbamoyl, (C1-C6 alkyl)carbonyl, (C1-C6 alkoxy)carbonyl, (C1-C6 alkyl)aminocarbonyl, di-(C1-C6 alkyl)aminocarbonyl, arylcarbonyl, aryloxycarbonyl, (C1-C6 alkyl) sulfonyl, arylsulfonyl, and 2-acetyl-3-oxobutanimidoyl cyanide.

In some embodiments, each $R_1$ together from a $C_5$-$C_{10}$-membered aromatic, heterocyclic, fused aromatic, fused heterocyclic, biaromatic, or bihetereocyclic ring system. In one such embodiment, each $R_1$ together form benzene. In some of these embodiments, $R_2$ is tert-butyl. In other of these embodiments, $R_2$ is 2-acetyl-3-oxobutanimidoyl cyanide (Formula II). In some other of these embodiments, $R_2$ is a C1-C6 alkyl furan, such as 2-propylfuran (Formula III), or a C2-C6 alkenyl furan, such as (E)-2-(prop-1-en-1-yl) furan (Formula IV).

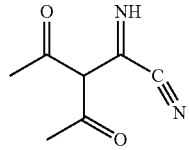

Formula II

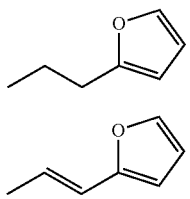

Formula III

Formula IV

In an embodiment, each $R_1$ is hydrogen. In some of these embodiments, $R_2$ is tert-butyl. In other of these embodiments, $R_2$ is 3-oxobutanimidoyl cyanide having a structure according to formula II. In some other of these embodiments, $R_2$ is a C1-C6 alkyl furan, such as 2-propylfuran, or a C2-C6 alkenyl furan, such as (E)-2-(prop-1-en-1-yl) furan.

The aPKC inhibitor or derivative thereof can exist as a salt or alcohol thereof, depending on protonation of the core compound as shown below:

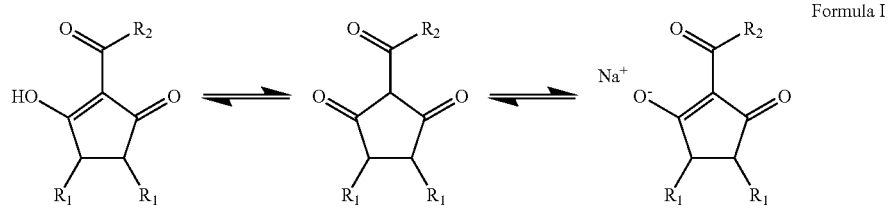

Formula I

Pharmaceutical Formulations

Also provided herein are pharmaceutical formulations that contain an effective amount of an aPKC inhibitor and/or derivative thereof described herein and a pharmaceutically acceptable carrier appropriate for administration to an individual in need thereof. In some embodiments, the aPKC inhibitor or derivative thereof is in the form of a pharmaceutically acceptable salt. Suitable pharmaceutically acceptable salts include, but are not limited to, sulfate, citrate, acetate, oxalate, chloride, hydrochloride, bromide, hydrobromide, iodide, nitrate, bisulfate, phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, malonate, mandelate, malate, phthalate, and pamoate. The pharmaceutical formulations or salts thereof can be administered to a subject in need thereof. In some embodiments, the subject has an aPKC abnormality. In further embodiments, the compounds described herein are used in the manufacture of a medicament for the treatment of an aPKC abnormality.

Pharmaceutically Acceptable Carriers and Auxiliary Ingredients and Agents

The pharmaceutical formulations containing an effective amount of an aPKC inhibitor and/or derivative thereof further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the effective amount of an aPKC inhibitor and/or derivative thereof, the pharmaceutical formulations can also include an effective amount of active agents, including but not limited to, antisense or RNA interference molecules, traditional chemotherapeutics, antineoplasic agents, immunomodulating compounds, hormones, antibiotics, antivirals, and/or antibodies or fragments thereof.

Effective Amounts of the aPKC Inhibitor, Derivative Thereof, and Auxiliary Active Agents The effective amount of the aPKC inhibitor or derivative thereof contained in the pharmaceutical formulation can range from about 0.001 micrograms to about 1000 grams. In some embodiments, the effective amount ranges of the aPKC inhibitor or derivative thereof from about 0.001 micrograms to about 0.01 micrograms. In other embodiments, the effective amount of the aPKC inhibitor or derivative thereof ranges from about 0.01 micrograms to about 0.1 micrograms. In further embodiments, the effective amount of the aPKC inhibitor or derivative thereof ranges from about 0.1 micrograms to about 1.0 grams. In yet further embodiments, the effective amount of the aPKC inhibitor or derivative thereof ranges from about 1.0 grams to about 10 grams. In other embodiments, the effective amount of the aPKC inhibitor or derivative thereof ranges from about 10 grams to about 100 grams. In still other embodiments, the effective amount of the aPKC inhibitor or derivative thereof ranges from about 100 grams to about 1000 grams.

In embodiments where there is an auxiliary active agent contained in the aPKC inhibitor or derivative thereof pharmaceutical formulation, the effective amount of the auxiliary active agent will vary depending on the auxiliary active agent. In some embodiments, the effective amount of the auxiliary active agent ranges from 0.001 micrograms to about 1000 grams. In other embodiments, the effective amount of the auxiliary active agent ranges from about 0.01 IU to about 1000 IU. In further embodiments, the effective amount of the auxiliary active agent ranges from 0.001 mL to about 1000 mL. In yet other embodiments, the effective amount of the auxiliary active agent ranges from about 1% w/w to about 50% w/w of the total pharmaceutical formulation. In additional embodiments, the effective amount of the auxiliary active agent ranges from about 1% v/v to about 50% v/v of the total pharmaceutical formulation. In still other embodiments, the effective amount of the auxiliary active agent ranges from about 1% w/v to about 50% w/v of the total pharmaceutical formulation.

The auxiliary active agent can be included in the pharmaceutical formulation or can exist as a stand-alone compound or pharmaceutical formulation that is administered contemporaneously or sequentially with the aPKC inhibitor, derivative thereof or pharmaceutical formulation thereof. In embodiments where the auxiliary active agent is a stand-alone compound or pharmaceutical formulation, the effective amount of the auxiliary active agent can vary depending on the auxiliary active agent used. In some of these embodiments, the effective amount of the auxiliary active agent ranges from 0.001 micrograms to about 1000 grams. In other embodiments, the effective amount of the auxiliary active agent ranges from about 0.01 IU to about 1000 IU. In further embodiments, the effective amount of the auxiliary active agent ranges from 0.001 mL to about 1000 mL. In yet other embodiments, the effective amount of the auxiliary active agent ranges from about 1% w/w to about 50% w/w of the total auxiliary active agent pharmaceutical formulation. In additional embodiments, the effective amount of the auxiliary active agent ranges from about 1% v/v to about 50% v/v of the total pharmaceutical formulation. In still other embodiments, the effective amount of the auxiliary active agent ranges from about 1% w/v to about 50% w/v of the total auxiliary agent pharmaceutical formulation.

Dosage Forms

In some embodiments, the pharmaceutical formulations described herein may be in a dosage form. The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intramuscular, intravenous, and intradermal. Such formulations may be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. The oral dosage form can be administered to a subject in need thereof. In some embodiments, this is a subject having an aPKC abnormality.

Where appropriate, the dosage forms described herein can be microencapsulated. The dosage form can also be prepared to prolong or sustain the release of any ingredient. In some embodiments, the aPKC inhibitor is the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Where appropriate, the dosage forms described herein can be a liposome. In these embodiments, the aPKC inhibitor, derivative thereof, auxiliary active ingredient, and/or pharmaceutically acceptable salt thereof are incorporated into a liposome. In some embodiments, an aPKC inhibitor, derivative thereof, auxiliary active ingredient, and/or pharmaceutically acceptable salts thereof is integrated into the lipid membrane of the liposome. In other embodiments, an aPKC inhibitor, derivative thereof, auxiliary active ingredient, and/or pharmaceutically acceptable salt thereof are contained in the aqueous phase of the liposome. In embodiments where the dosage form is a liposome, the pharmaceutical formulation is thus a liposomal formulation. The liposomal formulation can be administered to a subject in need thereof. In some embodiments, this is a subject having an aPKC abnormality.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the aPKC inhibitor, derivative thereof, auxiliary active ingredient, and/or pharmaceutically acceptable salt thereof can be formulated with a parafinnic or water-misicible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the aPKC inhibitor, derivative thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators.

In some embodiments, the dosage forms are aerosol formulations suitable for administration by inhalation. In some of these embodiments, the aerosol formulation contains a solution or fine suspension of an aPKC inhibitor, derivative thereof, auxiliary active ingredient, and/or pharmaceutically acceptable salt thereof a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of an aPKC inhibitor, derivative thereof, auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation.

For some dosage forms suitable and/or adapted for inhaled administration, the pharmaceutical formulation is a dry powder inhalable formulations. In addition to the aPKC inhibitor, derivative thereof, auxiliary active ingredient, and/or pharmaceutically acceptable salt thereof, such a dosage form can contain a powder base such as lactose, glucose, trehalose, manitol, and/or starch. In some of these embodiments, the aPKC inhibitor, derivative thereof, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the one or more of the compounds described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for injection can include aqueous and/or non-aqueous sterile injection solutions, which can contain antioxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Methods of Making aPKC Inhibitors and Derivatives Thereof

The aPKC inhibitors and derivatives thereof can be synthesized via many methods generally known to those skilled in the art. The present disclosure is not intended to be limited by the particular methods of synthesizing the aPKC inhibitors. For example, the core compound of Formula 1, wherein $R_1$ are each hydrogen and $R_2$ is a methyl group, can be synthesized from acid anhydrides and isopropenyl acetate as described in Merenyi and Nilsson, 1964. Acta. Chem. Scan. 18:1368-1372. Other aPKC inhibitors and derivatives thereof may or may not be synthesized starting from the core compound of Formula I. The skilled artisan will recognize additional methods of synthesizing the aPKC inhibitors described herein. For example, Muxfeldt, et al., 1968. J. Org. Chem. 33(4):1645-1647 describes the synthesis of derivatives of cyclopentane-1,3-dione from oxazolones; U.S. Pat. No. 3,381,035 describes methods of synthesizing 2-substituted cyclopentane-1,3-diones; and U.S. Pat. No. 3,773,622 describes methods of synthesizing 2-substituted-4-hydroxy-cyclopentane-1,3-diones.

Methods of Using aPKC Inhibitors and Formulations Thereof

Any amount, but particularly the effective amount of the aPKC inhibitors, derivatives thereof, and formulations thereof described herein can be administered as a dose one or more times per day, week, month, or year. Multiple doses can be give contemporaneously, such as in the case of an aerosol formulation, or can be given non-contemporaneously, such as multiple times per day where the administration is separated by at least about 2 minutes. The effective amount of the aPKC inhibitor can be given in a single dose. In other embodiments, the effective amount of the aPKC inhibitor compound or derivative thereof can be administered over multiple doses, in which each contains a fraction of the total effective amount to be administered ("sub-doses").

In some embodiments, the amount of doses and/or sub-doses delivered per day is 2, 3, 4, 5, or 6. In further embodiments, the doses or sub-doses are administered one or more times per week, such as 1, 2, 3, 4, 5, or 6 times per week. In other embodiments, the doses and/or sub-doses are administered one or more times per month, such as 1 to 8 times per month. In still further embodiments, doses and/or sub-doses one or more times per year, such as 1 to 11 times per year.

In some embodiments, an auxiliary active agent is used with an aPKC inhibitor, derivative thereof, or formulation thereof but is not directly included in the pharmaceutical formulation. In some of these embodiments, the aPKC inhibitor, derivative thereof, or formulation thereof the auxiliary agent can be administered contemporaneously with the aPKC inhibitor or derivative thereof. In one non-limiting example, during or at the time of oral administration of a dose or sub dose of the aPKC inhibitor formulation, the patient can receive an injection of the auxiliary agent. In another non-limiting example, the patient could take one tablet containing a dose of the aPKC inhibitor formulation and another tablet containing a dose of the aPKC inhibitor. In other embodiments, the auxiliary agent can be administered sequentially with the aPKC inhibitor, derivative thereof, or formulation thereof, wherein the administration of the aPKC inhibitor, derivative thereof, or formulation thereof and the auxiliary active agent is separated by an amount of time greater than about 10 minutes.

Kits Containinci an aPKC Inhibitor or Formulations Thereof

The compounds and pharmaceutical formulations described herein can be presented as a combination kit. As used herein, the terms "combination kit" or "kit of parts," or "kit" refers to the compound or pharmaceutical formulations and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

In some embodiments, the aPKC inhibitor or derivative thereof is kept separate from a diluent or other ingredient (active or inactive) until immediately prior to use. In these embodiments, the kit contains the aPKC inhibitor or derivative thereof in separate packaging from the other ingredient.

In embodiments where the aPKC inhibitor, derivative thereof, or pharmaceutical formulation thereof are administered along with a separate auxiliary active agent, the combination kit can contain each agent in separate pharmaceutical formulations. The separate pharmaceutical formulations (e.g. the aPKC inhibitor pharmaceutical formulation and the auxiliary active agent formulation) can be contained in a single package or in separate packages within the kit.

In some embodiments, the combination kit also includes instructions printed on or otherwise contained in a tangible medium of expression. The instructions can provide information regarding the content of the compound or pharmaceutical formulations contained therein, safety information regarding the content of the compound(s) or pharmaceutical formulation(s) contained therein, information regarding the dosages, indications for use, and/or recommended treatment regimen(s) for the compound(s) and/or pharmaceutical formulations contained therein. In some embodiments, the instructions provide directions for administering the compounds, pharmaceutical formulations, or salts thereof to a subject having an aPKC abnormality. In some embodiments, the aPKC abnormality is obesity, glucose intolerance, metabolic syndrome, hyperinsulinemia, hepatosteatosis, non-alcoholic cirrhosis, hypertriglyceridemia, hypercholesterolemia, polycystic ovary disease, and Alzheimer's disease.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. References cited incorporated by reference as if expressed in their entirety.

Example 1

Potential aPKC Inhibitor Compounds

A computational approach was used to identify potential aPKC inhibitor compounds. Some of these compounds are commercially available and others can be made using techniques known to the skilled artisan as described above. Briefly, a theoretical structure of PKCι was used to screen compounds from a database to identify compounds with structures that can fit in the binding pocket and thus bind aPKCs. A compound (2-acetylcyclopentane-1,3-dione (ACPD), Formula XI) having the general core structure described herein was identified and tested for its ability to bind and inhibit aPKC as described in the Examples herein. ACPD can be synthesized as described above or obtained commercially.

2-acetylcyclopentane-1,3-dione (ACPD)

Formula XI

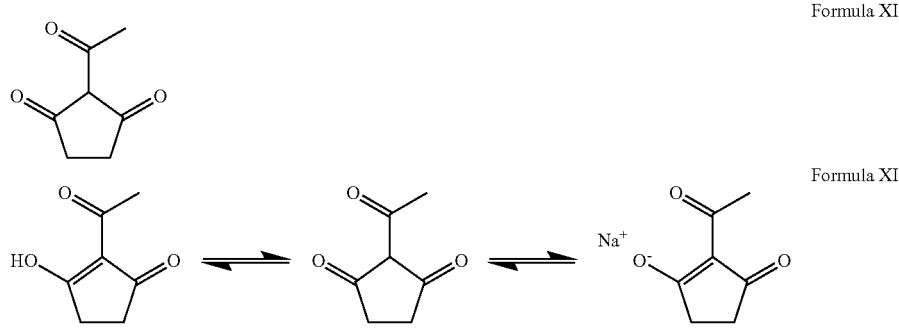

Formula XI

Other compounds were identified from the computational database search that contained the same core structure as ACPD, and are thus also expected to be aPKC inhibitors. These additional compounds are as follows:

2-(3-(furan-2-yl)propanoyl)cyclopentane-1,3-dione 2-(3-(furan-2-yl)propanoyl)cyclopentane-1,3-dione is an example potential aPKC inhibitor and is shown according to Formula V.

Formula V

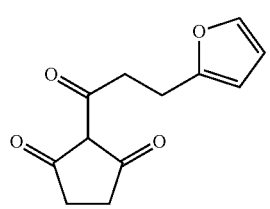

-continued
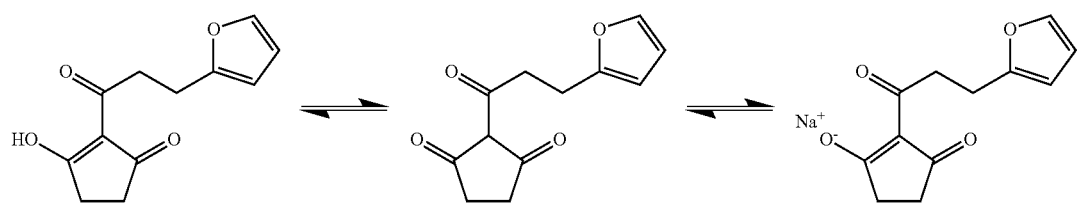
(E)-2-(3-(furan-2-yl)acryloyl)cyclopentane-1,3-dione
(E)-2-(3-(furan-2-yl)acryloyl)cyclopentane-1,3-dione is an example potential aPKC inhibitor and is shown according to Formula VI.
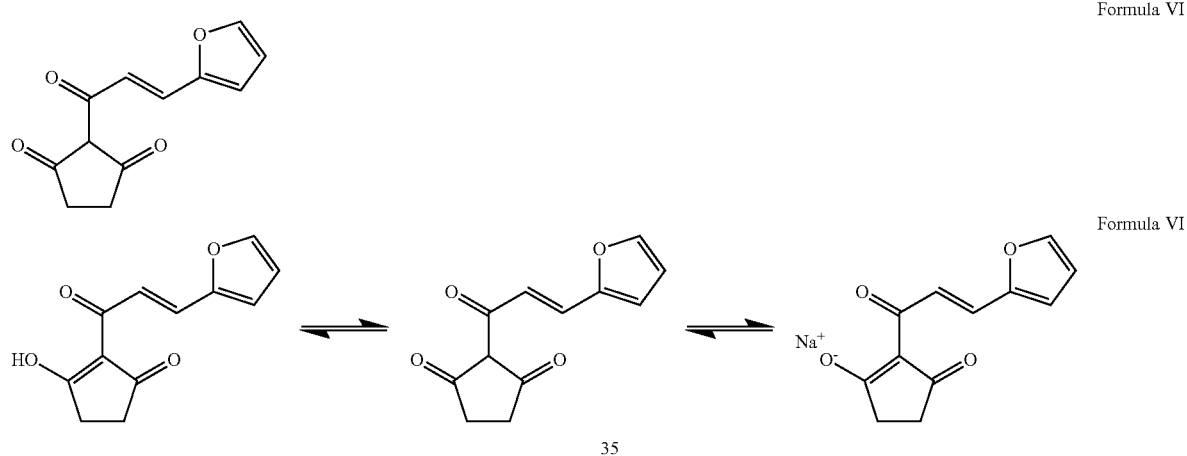
Formula VI
2-(3-(furan-2-yl)propanoyl)-1H-indene-1,3(2H)-dione
2-(3-(furan-2-yl)propanoyl)-1H-indene-1,3(2H)-dione is an example potential aPKC inhibitor and is shown according to Formula VII.
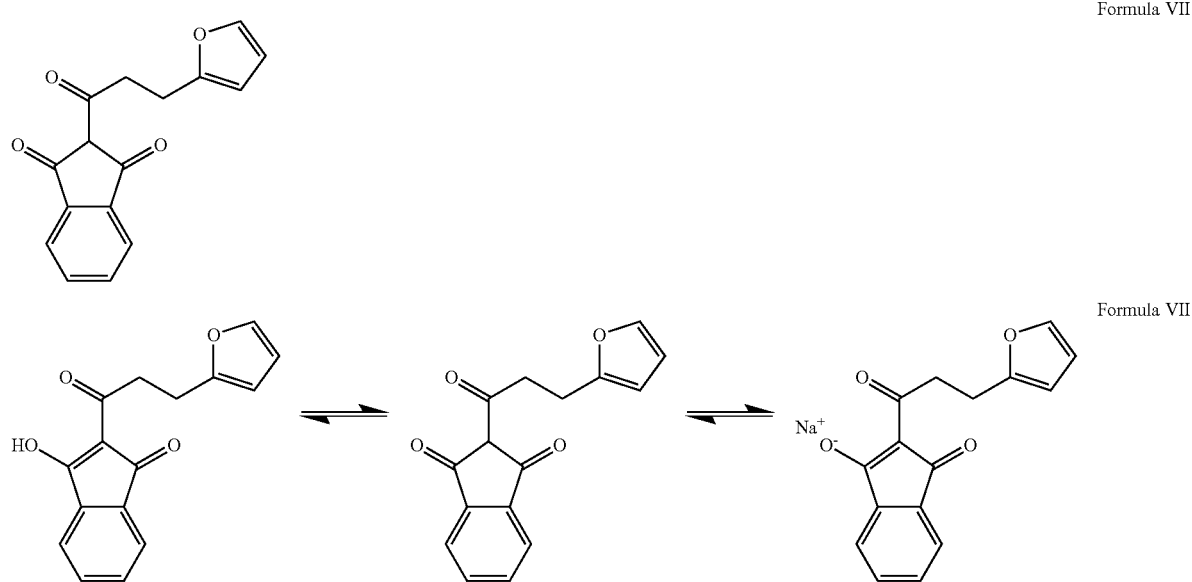
Formula VII

(E)-2-(3-(furan-2-yl)acryloyl)-1H-indene-1,3(2H)-dione (E)-2-(3-(furan-2-yl)acryloyl)-1H-indene-1,3(2H)-dione is an example potential aPKC inhibitor and is shown according to Formula VIII.

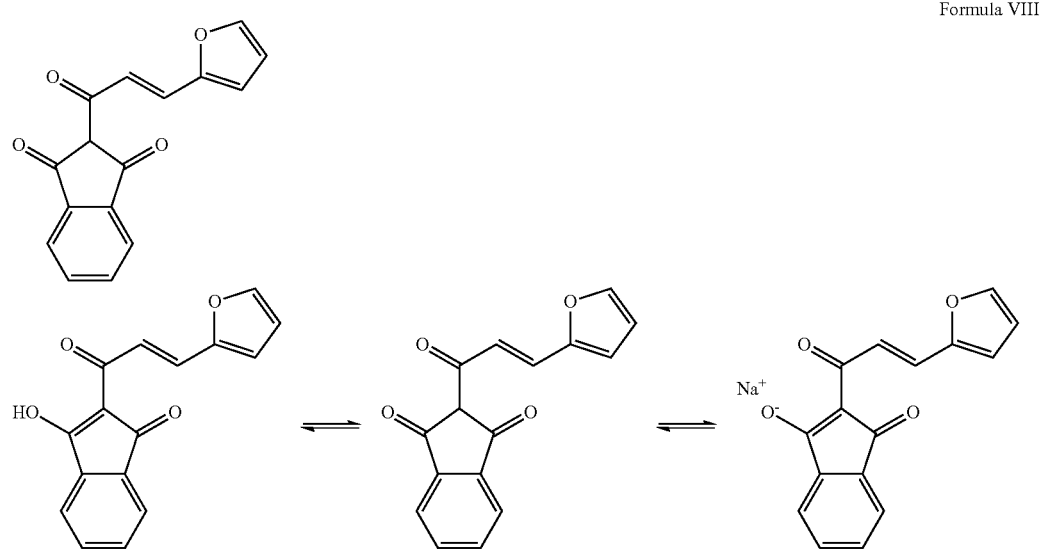

Formula VIII

2-pivaloyl-1H-indene-1,3(2H)-dione and Synthesis Thereof 2-pivaloyl-1H-indene-1,3(2H)-dione is an example potential aPKC inhibitor and is shown according to Formula IX.

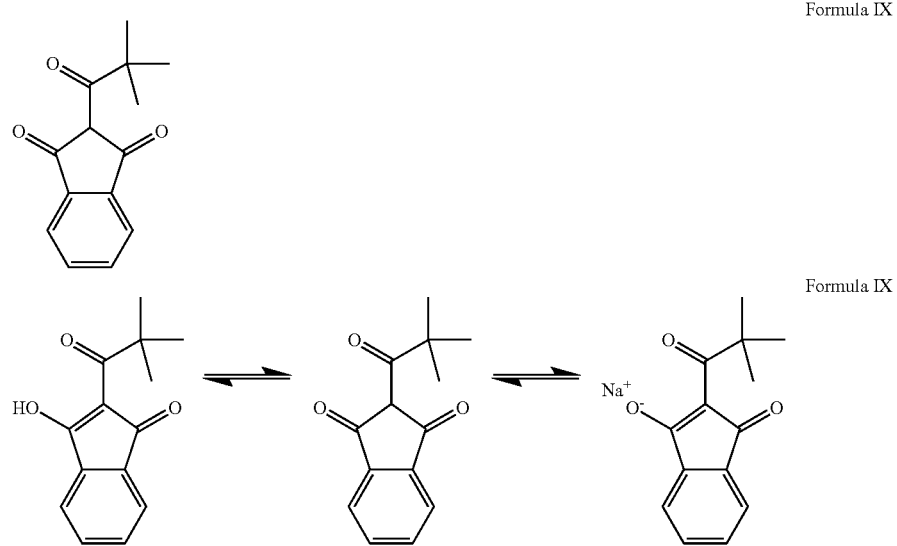

Formula IX

2-pivaloylcyclopentane-1,3-dione 2-pivaloylcyclopentane-1,3-dione is an example potential aPKC inhibitor and is shown according to Formula X.

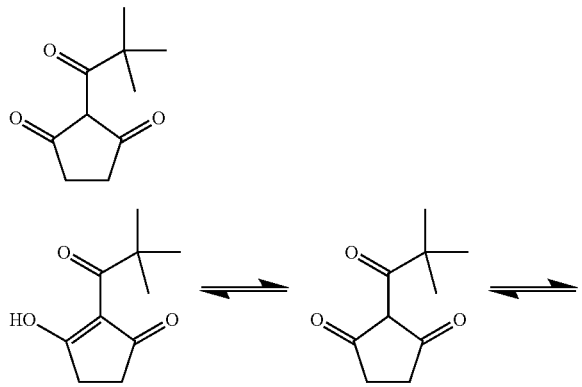

Formula X

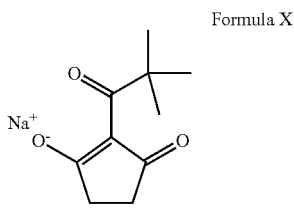

Formula X

Example 2

Dose-Related Effects of ACPD on PIP3-Stimulated Activities of PKC-ι and PKC-ζ and PMA-Stimulated Activities of PKC-α, PKC-β2, PKC-δ, and PKC-ε

Methods

ACPD used in this Example was obtained from Sigma (St. Louis, Mo., USA). PIP3-stimulated activities of PKC-ι and PKC-ζ were measured as follows. 10 ng of recombinant forms of human aPKCs (PKC-ι and PKC-ζ) (Biovision, Mountain, Calif., USA) were assayed for aPKC activity in the presence of 10 fmol/l phosphatidylinositol-3,4,5-$(PO_4)_3$ ($PIP_3$) (Matreya, Pleasant Gap, Pa., USA) with and without addition of varying amounts of ACPD. $PIP_3$ was added to activate and define aPKC activity. The aPKC activity assay was performed as described in (for example) Sajan et al. 2012. Metabolism. 61:459-469. Briefly, recombinant aPKCs were incubated for 8 minutes at 30° C. in 100 μl buffer containing 50 mmol/l Tris/HCl (pH,7.5), 100 μmol/l $Na_3VO_4$, 100 μmol/l $Na_4 P_2O_4$, 1 mmol/l NaF, 100 μmol/l PMSF, 4 μg phosphatidylserine (Sigma, St. Louis, Mo., USA), 50 μmol/l [γ-$^{32}PO_4$]ATP (NEN Life Science Products, Beverly, Mass., USA), 5 mmol/l $MgCl_2$, and, as substrate, 40 μmol/l serine analogue of the PKC-ε pseudo-substrate (Millipore, Bedford, Mass., USA). After incubation, $^{32}$P-labeled substrate was trapped on P-81 filter paper and counted. This assay reflects the specific activity of a constant amount of the aPKCs.

Additionally, recombinant forms of human PKC-α, PKC-β2, PKC-δ and PKC-ε (gifts from Sphinx Division, Lilly Corp., Indianapolis, Ind., USA) were assayed for their activity, as previously described with respect to the recombinant aPKCs, in the presence of 1 mmol/l CaCl2 and 100 nmol/l phorbol myristoyl acetate (PMA) for PKC-α and PKC-β2, and in the presence of 100 nmol/l PMA for PKC-δ and PKC-ε to activate and define respective PKC activities. PMA was added to activate and define the PKC activity.

Data are expressed as mean±SEM, and P values were determined by one-way ANOVA and least-significant multiple comparison methods.

Results

Figures 1A, 1B:
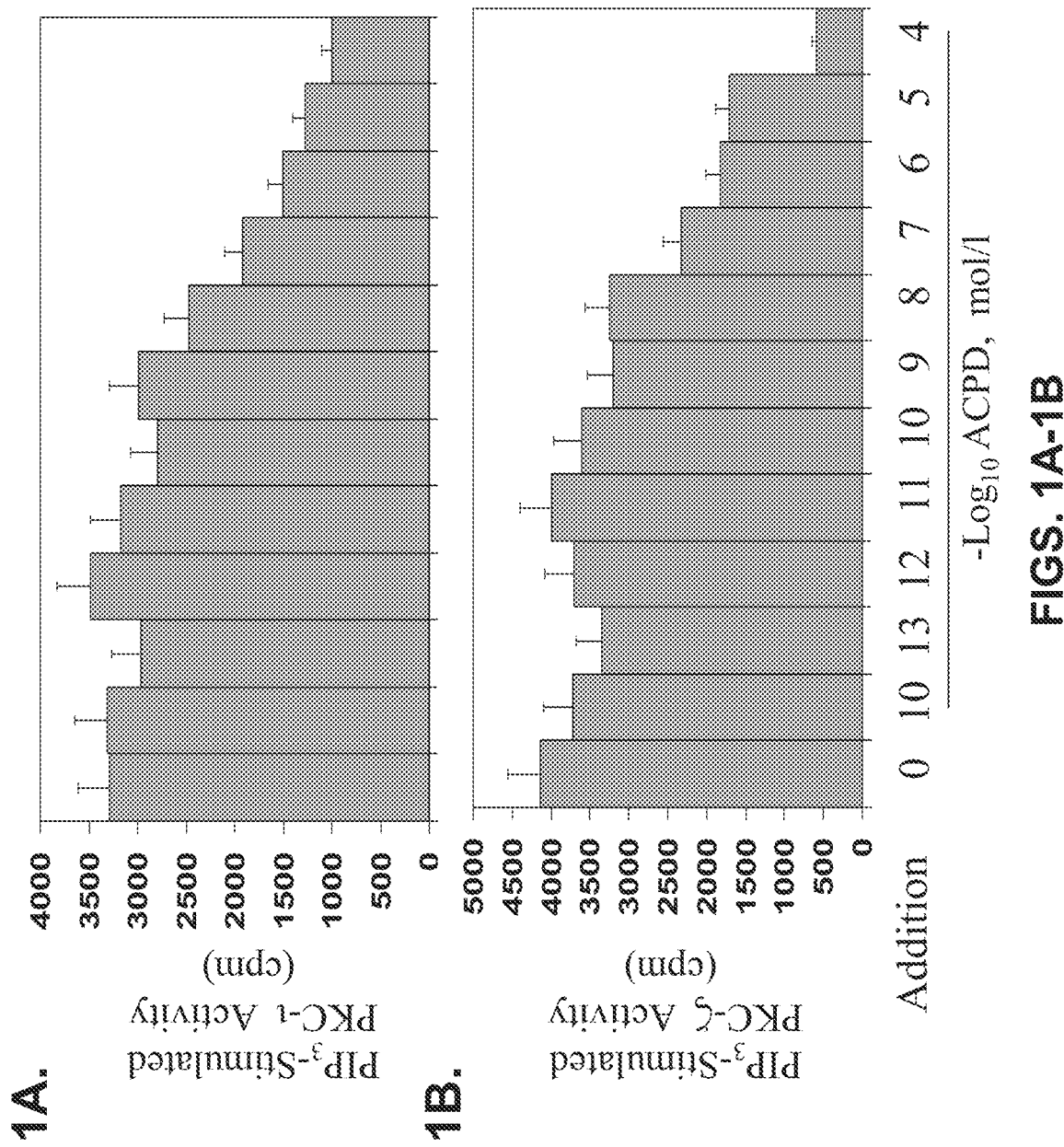
FIGS. 1A-1B show dose-related effects of ACPD on PIP3-stimulated activities of PKC-ι (FIG. 1A) and PKC-ζ (FIG. 1B). Recombinant preparations of PKC-ι and PKC-ζ were incubated with 10 fmol/l PIP3, indicated concentrations of ACPD, and other components of the aPKC assay system and examined for $^{32}PO_4$-labeling of substrate. Values are mean±SEM of 4 determinations.
Figure 2A:
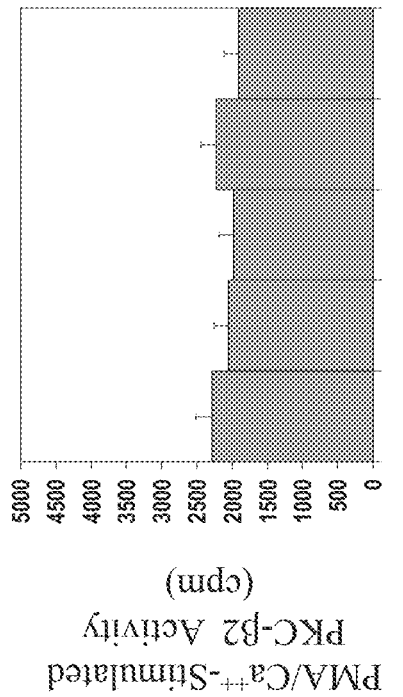
FIGS. 2A-2D show dose-related effects of ACPD on Phorbol Myristoyl Acetate (PMA)-±CaCl$_2$-stimulated Activities of PKC-α (FIG. 2A), PKC-β2 (FIG. 2B), PKC-δ (FIG. 2C) and PKC-ε (FIG. 2D). Recombinant preparations of indicated PKCs were incubated with 100 nmol/l PMA±1 mmol/l CaCl$_2$, as indicated, and indicated concentrations of ACPD and other components of the PKC assay system, and examined for $^{32}PO_4$-labeling of substrate. Values are Mean±SEM of 4 determinations.
Figure 2B:
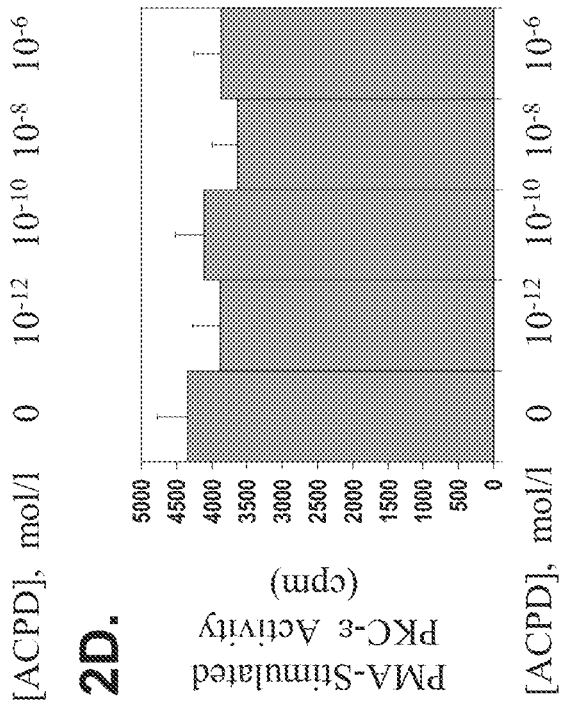
Figure 2C:
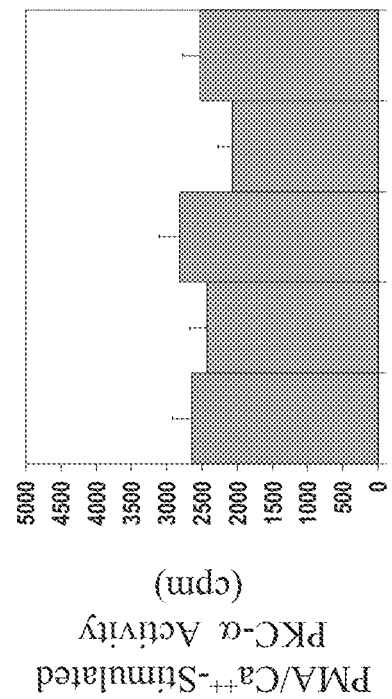
Figure 2D:
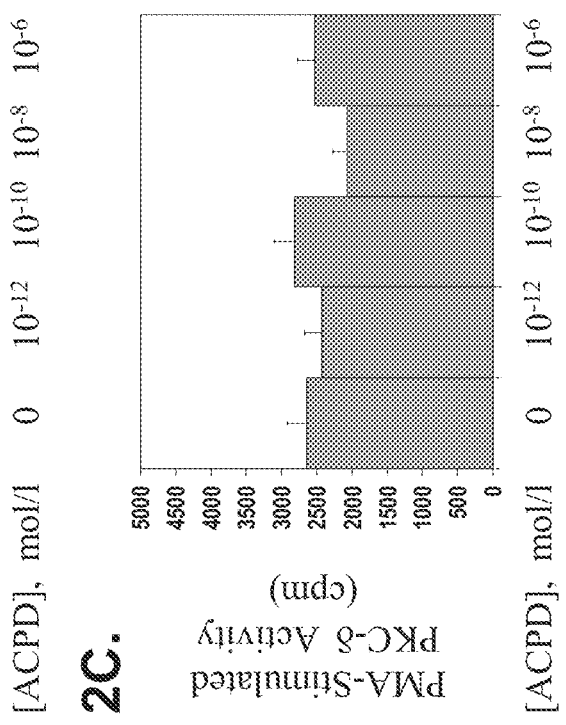

Results from the aPKC and PKC activity assays are shown in FIGS. 1A-1B and 2A-2D. FIGS. 1A-1B show the dose-related effects of ACPD on PIP3-stimulated activities of PKC-ι (FIG. 1A) and PKC-ζ (FIG. 1B). Values are mean±SEM of 4 determinations. FIGS. 2A-2D show dose-related effects of ACPD on Phorbol Myristoyl Acetate (PMA)-±$CaCl_2$-stimulated Activities of PKC-α (FIG. 2A), PKC-β2 (FIG. 2B), PKC-δ (FIG. 2C) and PKC-ε (FIG. 2D). As shown in FIGS. 1A-1B, ACPD reduces the activities of PKC-ι (FIG. 1A) and PKC-ζ (FIG. 1B) in a dose-dependent manner. ACPD did not reduce activities of PKC-α (FIG. 2A), PKC-β2 (FIG. 2B), PKC-δ (FIG. 2C) and PKC-ε (FIG. 2D). As shown in FIGS. 1A-1B, ACPD had comparable potencies (approximately Ki, $10^{-7}$ mol/l) for diminishing the activities of both PKC-ζ and PKC-ι. Moreover, ACPD was without effect on activities of recombinant forms of PKC-α, PKC-β2, PKC-δ and PKC-ε stimulated maximally with phorbol±calcium chloride (FIGS. 2A-2D), suggesting that ACPD is an aPKC-specific, pan-aPKC inhibitor, meaning that ACPD inhibits both forms of aPKC enzymes without having an effect on the activity of other PKC enzymes.

Example 3

Dose-Related Effects of ACPD on Activities of Total aPKC and Akt2 in Control and Insulin-Stimulated Hepatocytes of Non-Diabetic Humans Methods Hepatocyte Incubations: Cryo-preserved hepatocytes (70-90% viability; purchased from Zen-Bio Corp, Research Triangle, N.C., USA, were harvested from perfused livers of non-diabetic subjects [2 females and 6 males; ages, 43-60 years, 51±3 (mean±SEM); BMI, 30±2] and type 2 diabetic subjects [2 females and 4 males, ages, 46-68 years, 60±4; BMI, 27±2] maintained on life support as transplant donors (these hepatocytes were obtained from the same patient groups described in Sajan and Farese. 2012. Diabetologia. 55:1446-1457). Diabetic subjects were hyperglycaemic and undergoing insulin treatment. Other pertinent laboratory and clinical data are not available in transplant donors.

Hepatocytes were incubated (about $10^6$ cells/100 mm plate) overnight (approx.16 hours) in Dulbecco's minimal essential medium containing about 5% fetal calf serum, about 100 units/ml sodium-penicillin, about 100 μg/ml streptomycin-sulfate, about 2 μmol/l dexamethasone, followed by incubation for about 2 hours in William's E medium (Sigma, St. Louis, Mo., USA) containing Glutamax (Invitrogen, Carlsbad, Calif., USA), 100 units/ml sodium-penicillin, 100 μg/ml streptomycin-sulfate, 100 nmol/l dexamethasone, followed by incubation for about 4 hours in similar medium supplemented with about 25 mg/ml transferrin and about 0.25 µg/ml sodium selenite. Where indicated, about 1 µmol/l insulin and varying concentrations of ACPD were present in the media throughout all incubations. This concentration of insulin was added to maintain a high level of insulin activation of aPKC during prolonged incubation. For comparison, about 100 nmol/l insulin was less effective than about 1 µmol/l insulin in maintaining increases in aPKC and Akt activity in non-diabetic hepatocytes.

All experimental procedures involving human materials were approved by the Institutional Review Board of the University of South Florida College of Medicine and the James A. Haley Veterans Administration Medical Center Research and Development Committee, Tampa, Fla., and conducted in accordance with the Declaration of Helsinki and Good Clinical Practice.

Activity Assays: As described in Sajan and Farese. 2012. Diabetologia. 55:1446-1457, aPKCs were immunopercipitated from lysates with rabbit polyclonal antiserum (Santa Cruz Biotechnologies, Santa Cruz, Calif., USA) which recognizes C-termini of PKC-ζ and PKC-λ/ι. Note that PKC-ι is the human homolog of mouse PKC-ζ with 98% homology; human and mouse muscle contain primarily PKC-ι/λ and little PKC-ζ; mouse and human liver contain substantial amounts of both PKC-ι/ζ and PKC-ζ (Farese and Sajan. 2010. Am. J. Physiol. Endocrinol. Metab. 298:E385-394).

To measure aPKC activity, immunoprecipitates were collected on Sepharose-AG beads (Santa Cruz Biotechnologies) and incubated for 8 minutes at 30° C. in 100 µl buffer containing 50 mmol/l Tris/HCl (pH,7.5), 100 µmol/l $Na_3VO_4$, 100 µmol/l $Na_2P_2O_4$, 1 mmol/l NaF, 100 µmol/l PMSF, 4 µg phosphatidylserine (Sigma, St. Louis, Mo., USA), 50 µmol/l [γ-$^{32}PO_4$]ATP (NEN Life Science Products, Beverly, Mass., USA), 5 mmol/l $MgCl_2$, and, as substrate, 40 µmol/l serine analogue of the PKC-ε pseudo-substrate (Millipore, Bedford, Mass., USA). After incubation, $^{32}P$-labeled substrate was trapped on P-81 filter paper and counted. aPKC activation was also assessed by immunoblotting for phosphorylation of the auto(trans)phosphorylation site, thr-555/560 in PKC-ι/ζ, required for, and reflective of, activation (Farese and Sajan. 2010. Am. J. Physiol. Endocrinol. Metab. 298:E385-394).

Akt2 enzyme activity was assayed in immunoprecipitates using a kit purchased from Millipore, as described in Sanjan et. al. 2010. Am. J. Physiol. Endocrinol. Metab. 298:E179-192 and Sajan and Farese (2012). Diabetologia. 55:1446-1457. Akt activity was also assessed by immunoblotting for phosphorylation of ser-473-Akt.

Data are expressed as mean±SEM, and P values were determined by one-way ANOVA and least-significant multiple comparison methods.

Results

Figures 3A, 3B:
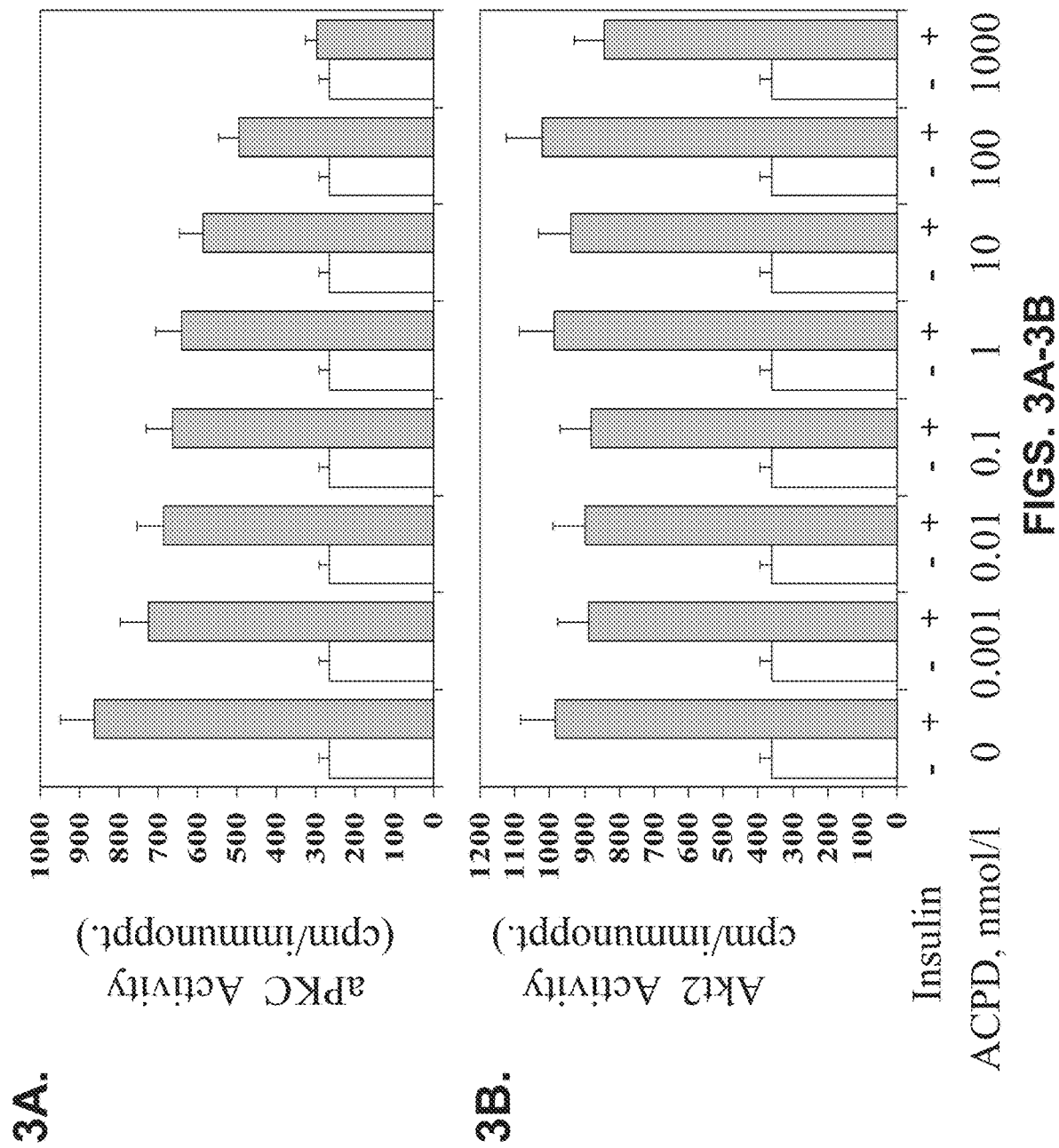
FIGS. 3A-3B show dose-related effects of ACPD on Activities of Total aPKC (FIG. 3A) and Akt2 (FIG. 3B) in control and insulin-stimulated hepatocytes of non-diabetic humans. Hepatocytes were incubated for 24 hours±1 μmol/l insulin and indicated concentrations of ACPD and examined for immunoprecipitable activities of total aPKC and Akt2. Values are mean±SEM of 4 determinations.

As shown in FIG. 3A, ACPD inhibited insulin-stimulated increases in total aPKC activity in hepatocytes of non-diabetic humans, with half-maximal and maximal inhibition occurring at approximately $10^{-7}$ and $10^{-6}$ mol/ml. The concentrations of ACPD required for inhibition of total aPKC in human hepatocytes were similar to those required for inhibition of recombinant forms of PKC-ι and PKC-ζ. Basal activity (FIG. 3A, open bars), on the other hand, was not affected by ACPD, suggesting that either the activated form of aPKC is more open and accessible for interaction with inhibitor or non-aPKC kinases co-immunoprecipitate with aPKC and are not inhibited by ACPD. In any case, it is only the stimulated activity that can more clearly be attributed to aPKC. As shown in FIG. 3B, ACPD did not inhibit basal (open bars) or insulin-stimulated increases in hepatic Akt2 activity. Similarly, ACPD had no effects on activity of AMP-activated protein kinase (AMPK).

Example 4

Effect of ACPD on Expression of Lipogenic and Gluconeogenic Factors in Basal and Insulin-Stimulated Hepatocytes of Non-Diabetic and Type 2 Diabetic (T2DM) Humans Methods Hepatocyte Incubations: Cryo-preserved hepatocytes (70-90% viability; purchased from Zen-Bio Corp, Research Triangle, N.C., USA, were harvested from perfused livers of non-diabetic subjects [2 females and 6 males; ages, 43-60 years, 51±3 (mean±SEM); BMI, 30±2] and type 2 diabetic subjects [2 females and 4 males, ages, 46-68 years, 60±4; BMI, 27±2] maintained on life support as transplant donors (these hepatocytes were obtained from the same patient groups described in Sajan and Farese. 2012. Diabetologia. 55:1446-1457). Diabetic subjects were hyperglycaemic and undergoing insulin treatment. Other pertinent laboratory and clinical data are not available in transplant donors.

Hepatocytes were incubated (about $10^6$ cells/100 mm plate) overnight (approx. 16 hours) in Dulbecco's minimal essential medium containing about 5% fetal calf serum, about 100 units/ml sodium-penicillin, about 100 µg/ml streptomycin-sulfate, about 2 µmol/l dexamethasone, followed by incubation for about 2 hours in William's E medium (Sigma, St. Louis, Mo., USA) containing Glutamax (Invitrogen, Carlsbad, Calif., USA),100 units/ml sodium-penicillin, 100 µg/ml streptomycin-sulfate, 100 nmol/l dexamethasone, followed by incubation for about 4 hours in similar medium supplemented with about 25 mg/ml transferrin and about 0.25 µg/ml sodium selenite. Where indicated, about 1 µmol/l insulin and varying concentrations of ACPD were present in the media throughout all incubations. This concentration of insulin was added to maintain a high level of insulin activation of aPKC during prolonged incubation. For comparison, about 100 nmol/l insulin was less effective than about 1 µmol/l insulin in maintaining increases in aPKC and Akt activity in non-diabetic hepatocytes.

All experimental procedures involving human materials were approved by the Institutional Review Board of the University of South Florida College of Medicine and the James A. Haley Veterans Administration Medical Center Research and Development Committee, Tampa, Fla., and conducted in accordance with the Declaration of Helsinki and Good Clinical Practice.

Cell preparation: The treated hepatocytes were homogenized in ice-cold buffer containing 0.25 mol/l sucrose, 20 mmol/l Tris/HCl (pH, 7.5), 2 mmol/l EGTA, 2 mmol/l EDTA, 1 mmol/l phenlysulfonlyfluoride (PMSF), 20 µg/ml leupeptin, 10 µg/ml aprotinin, 2 mmol/l Na4P2O7, 2 mmol/l Na3VO4, 2 mmol/l NaF, and 1 µmol/l microcystin, and then supplemented with 1% TritonX-100, 0.6% Nonidet and 150 mmol/l NaCl, and cleared by low-speed centrifugation.

mRNA quantification: Cell preparations were added to Trizol reagent (Invitrogen) and RNA was extracted and purified with RNA-Easy Mini-Kit and RNAase-free DNAase Set (Qiagen, Valencia, Calif., USA), quantified ($A_{260}/A_{280}$), checked for purity by electrophoresis on 1.2% agarose gels, and quantified by quantitative real-time reverse transcriptase-polymerase chain reaction (RT-PCR), using TaqMan reverse transcription reagent and SYBR Green kit (Applied Biosystems, Carlsbad, Calif., USA) with human nucleotide primers shown in Table 1 and as described in Sajan et al. 2012. Metabolism. 61:459-469. mRNA expression is normalized to hypoxanthine phosphoribosyl-transferase (HPT) mRNA expression.

TABLE 1

| GENE | Forward Primer Sequence (5'→3') | Reverse Primer Sequence (5'→3') |
|---|---|---|
| SREBP 1 | SEQ ID NO: 1<br>ATCGGCGCGGAAGCTGTCGGGGTAGCGTC | SEQ ID NO: 2<br>ACTGTCTTGGTTGATGAGCTGGAGCAT |
| PEPCK | SEQ ID NO: 3<br>GACAGCCTGCCCCAGGCAGTGA | SEQ ID NO: 4<br>CTGGCCACATCTCGAGGGTCAG |
| FAS | SEQ ID NO: 5<br>ACCGACTTCATGAATTTGCTGAT | SEQ ID NO: 6<br>AAGCTGAAAGCTTTCTGTCT |
| G6Pase | SEQ ID NO: 7<br>TGCTGCTCACTTTCCCCACCAG | SEQ ID NO: 8<br>TCTCCAAAGTCCACAGGAGGT |
| HPT | SEQ ID NO: 9<br>TGAAAGACTTGCTCGAGATGT | SEQ ID NO: 10<br>AAAGAACTTATAGCCCCCCTT |

Data are expressed as mean±SEM, and P values were determined by one-way ANOVA and least-significant multiple comparison methods.

Results

As demonstrated in FIGS. 4A-4D, ACPD diminished insulin-dependent increases in expression of lipogenic factors, SREBP-1c (FIG. 4A) and FAS (FIG. 4C), in hepatocytes of non-diabetic humans. ACPD also diminished diabetes-dependent increases in SREBP-1c and FAS in hepatocytes of type 2 diabetic humans (FIGS. 4A and 4C, respectively). Insulin did not increase SREBP-1c and FAS mRNA beyond the increases provoked by type 2 diabetes. This suggests that aPKC activity is already maximally or near maximally activated in diabetic hepatocytes and consequently unable to respond to further stimulation.

ACPD diminished basal expression of PEPCK and G6Pase in non-diabetic hepatocytes (FIGS. 4B and 4D, respectively). ACPD also diminished diabetes-dependent increases in PEPCK and G6Pase expression in hepatocytes of type 2 diabetic humans (FIGS. 4B and 4D, respectively). Insulin diminished the expression of PEPCK and G6Pase in non-diabetic hepatocytes, but not in hepatocytes of type 2 diabetic humans (FIGS. 4B and 4D, respectively). This suggests diminished activation of Akt by insulin is seen in these hepatocytes or uncoupling of Akt from downstream factors that directly control gluconeogenic gene transcription, such as FoxO1, or both. See e.g. FIG. 24.

Example 5

Effect of ACPD on Resting/Basal and Insulin-Stimulated aPKC Activity in Mouse Liver and Muscle Methods Standard (C57Bl/6/SV129) mice consuming standard low-fat mouse chow were injected subcutaneously (s.c.) with a single injection of ACPD (10 mg/kg body weight). At about 0, 24, 48, and 72 hours post injection, mice were treated with or without an intraperitoneal injection of insulin (1 U/kg body weight) or control 15 minutes prior to killing. Post mortem, liver and muscle tissues were removed and examined for immunoprecipitable aPKC activity as described below.

Tissue Preparation: liver and muscle tissue samples were homogenized in an ice-cold buffer containing 0.25 mol/l sucrose, 20 mmol/l Tris/HCl (pH, 7.5), 2 mmol/l EGTA, 2 mmol/l EDTA, 1 mmol/l phenlysulfonlyfluoride (PMSF), 20 µg/ml leupeptin, 10 µg/ml aprotinin, 2 mmol/l Na4P2O7, 2 mmol/l Na3VO4, 2 mmol/l NaF, and 1 µmol/l microcystin, and then supplemented with 1% TritonX-100, 0.6% Nonidet and 150 mmol/l NaCl, and cleared by low-speed centrifugation.

aPKC Activity Assay: As described in Sajan and Farese. 2012. Diabetologia. 55:1446-1457, aPKCs were immunopercipitated from lysates with rabbit polyclonal antiserum (Santa Cruz Biotechnologies, Santa Cruz, Calif., USA) which recognizes C-termini of PKC-□ and PKC-λ/ι. Note that PKC-ι is the human homolog of mouse PKC-ζ with 98% homology; human and mouse muscle contain primarily PKC-ι/λ and little PKC-ι; mouse and human liver contain substantial amounts of both PKC-ζ/λ and PKC-ζ (Farese and Sajan. 2010. Am. J. Physiol. Endocrinol. Metab. 298: E385-394).

To measure aPKC activity, immunoprecipitates were collected on Sepharose-AG beads (Santa Cruz Biotechnologies) and incubated for 8 minutes at 30° C. in 100 µl buffer containing 50 mmol/l Tris/HCl (pH,7.5), 100 µmol/l Na$_3$VO$_4$, 100 µmol/l Na$_4$P$_2$O$_4$, 1 mmol/l NaF, 100 µmol/l PMSF, 4 µg phosphatidylserine (Sigma, St. Louis, Mo., USA), 50 µmol/l [γ-$^{32}$PO$_4$]ATP (NEN Life Science Products, Beverly, Mass., USA), 5 mmol/l MgCl$_2$, and, as substrate, 40 µmol/l serine analogue of the PKC-ε pseudo-substrate (Millipore, Bedford, Mass., USA). After incubation, $^{32}$P-labeled substrate was trapped on P-81 filter paper and counted. aPKC activation was also assessed by immunoblotting for phosphorylation of the auto(trans)phosphorylation site, thr-555/560 in PKC-ι/ζ, required for, and reflective of, activation (Farese and Sajan. 2010. Am. J. Physiol. Endocrinol. Metab. 298:E385-394).

Data are expressed as mean±SEM, and P values were determined by one-way ANOVA and least-significant multiple comparison methods.

Results

As shown in FIGS. 5A-5B, treatment of normal mice with a single s.c. dose of ACPD (10 mg/kg body weight) elicited a decrease in hepatic insulin-stimulated aPKC activity that was observed at 24 hours post ACPD treatment and returned to pre-treatment levels over the following 48 hours (FIG. 5A). In contrast, insulin-stimulated aPKC activity in muscle was not altered by ACPD treatment at any time point (FIG.

5B), This suggests that in normal, low-fat fed mice and as administered in this Example, ACPD selectively inhibited hepatic aPKC.

Example 6

Shows the Effect of High Fat Feeding (HFF) and ACPD or ICAP (s.c. Injection of ICAP, 1 mg/kg Body Weight, or ACPD; 10 mg/kg Body Weight) on Basal and Insulin-Stimulated Activity of aPKC and Akt2 in Muscle and Liver Methods Standard (C57Bl/6/SV129) mice consuming standard low-fat mouse chow were injected subcutaneously (s.c.) with a daily single injection of ICAP (1 mg/kg body weight) or ACPD (10 mg/kg body weight). After 10 weeks of feeding a low fat diet (10% calories from fat) (control mice) or a high fat diet (40% of calories from milk fat) and daily treatment with or without aPKC inhibitor (ACPD or 1H-imidazole-4-carboxamide, 5-amino-1-[2,3-dihydroxy-4-[(phosphono-oxy)methyl]cyclopentyl-[1R-(1a,2b,3b,4a) (ICAP)), mice were injected with or without insulin (1 U/kg body weight given intraperitoneally) and killed 15 minutes post insulin injection. Post mortem, liver and muscle tissues were removed and examined for immunoprecipitable aPKC activity and akt2 as described below.

Tissue Preparation: Liver and muscle tissue samples were homogenized in ice-cold buffer containing 0.25 mol/l sucrose, 20 mmol/l Tris/HCl (pH, 7.5), 2 mmol/l EGTA, 2 mmol/l EDTA, 1 mmol/l phenlysulfonlyfluoride (PMSF), 20 µg/ml leupeptin, 10 µg/ml aprotinin, 2 mmol/l Na4P2O7, 2 mmol/l Na3VO4, 2 mmol/l NaF, and 1 µmol/l microcystin, and then supplemented with 1% TritonX-100, 0.6% Nonidet and 150 mmol/l NaCl, and cleared by low-speed centrifugation.

aPKC Activity Assay: As described in Sajan and Farese. 2012. Diabetologia. 55:1446-1457, aPKCs were immunopercipitated from lysates with rabbit polyclonal antiserum (Santa Cruz Biotechnologies, Santa Cruz, Calif., USA) which recognizes C-termini of PKC-ζ and PKC-λ/ι. Note that PKC-ι is the human homolog of mouse PKC-ζ with 98% homology; human and mouse muscle contain primarily PKC-ι/λ and little PKC-ζ; mouse and human liver contain substantial amounts of both PKC-ζ/λ and PKC-ζ (Farese and Sajan. 2010. Am. J. Physiol. Endocrinol. Metab. 298: E385-394).

To measure aPKC activity, immunoprecipitates were collected on Sepharose-AG beads (Santa Cruz Biotechnologies) and incubated for 8 minutes at 30° C. in 100 µl buffer containing 50 mmol/l Tris/HCl (pH,7.5), 100 µmol/l Na$_3$VO$_4$, 100 µmol/l Na$_4$P$_2$O$_4$, 1 mmol/l NaF, 100 µmol/l PMSF, 4 µg phosphatidylserine (Sigma, St. Louis, Mo., USA), 50 µmol/l [γ-$^{32}$PO$_4$]ATP (NEN Life Science Products, Beverly, Mass., USA), 5 mmol/l MgCl$_2$, and, as substrate, 40 µmol/l serine analogue of the PKC-ε pseudosubstrate (Millipore, Bedford, Mass., USA). After incubation, $^{32}$P-labeled substrate was trapped on P-81 filter paper and counted. aPKC activation was also assessed by immunoblotting for phosphorylation of the auto(trans)phosphorylation site, thr-555/560 in PKC-ι/ζ, required for, and reflective of, activation (Farese and Sajan. 2010. Am. J. Physiol. Endocrinol. Metab. 298:E385-394).

Akt2 enzyme activity was assayed in immunoprecipitates using a kit purchased from Millipore, as described in Sanjan et. al. 2010. Am. J. Physiol. Endocrinol. Metab. 298:E179-192 and Sajan and Farese (2012). Diabetologia. 55:1446-1457.

Data are expressed as mean±SEM, and P values were determined by one-way ANOVA and least-significant multiple comparison methods.

Results

In control mice consuming a standard chow, low fat diet (10% calories from fat), insulin increased phosphorylation and enzyme activity of both aPKC and Akt2 in liver and muscle (FIGS. 6A-6D). However, in HFF mice basal hepatic activities of both aPKC and Akt2 were elevated (FIGS. 6A and 6C). This most likely reflects hyperinsulinemia in these mice. For aPKC, this suggests increases in lipid activators of aPKC in these mice. Insulin appeared to have provoked further increases in the activities of hepatic aPKC and Akt2 to levels comparable to or exceeding those attained in control mice (FIGS. 6A and 6C). These data suggest that insulin signaling to both hepatic factors was fully intact in this model of modestly increased dietary fat.

Treatment of HFF mice with the doses of ICAP (1 mg/kg body-weight) and ACPD (10 mg/kg body-weight) diminished resting and insulin-stimulated hepatic aPKC activity to control levels (FIG. 6A). On the other hand, hepatic Akt2 activity, if anything, increased further with ICAP and ACPD treatment (FIG. 6C). These data suggest that both inhibitors specifically inhibited aPKC and at least spared Akt2 and may have enhanced Akt2 activation. ICAP is specific for PKC-ι/λ, whereas ACPD is specific for both PKC-ι/λ and PKC-ζ. Neither ICAP nor ACPD affects other PKCs.

In contrast to liver, basal, and insulin-stimulated phosphorylation, activities of both aPKC and Akt2 were diminished in muscles of HFF mice (FIGS. 6B and 6D, respectively). Moreover, in muscle, treatment with ICAP or ACPD increased both aPKC and Akt2 activity toward, albeit not fully to, normal levels (FIGS. 6A and 6B). The reason for the hepatic selectivity of both ICAP and ACPD is beneficial for simultaneously improving muscle and liver.

Example 7

Effects of HFF Diet and ICAP (I) or ACPD (A) on Hepatic Resting/Basal and Insulin Stimulated Phosphorylation of Ser$^{473}$-Akt, Ser9-GSK3β, Thr$^{555/560}$-PKC-λ/ζ, and Thr$^{2448}$-mTOR Methods Standard (C57Bl/6/SV129) mice consuming standard low-fat mouse chow were injected subcutaneously (s.c.) with a daily single injection of ICAP (1 mg/kg body weight) or ACPD (10 mg/kg body weight). After 10 weeks of feeding a low fat diet (10% calories from fat) (control mice) or a high fat diet (40% of calories from milk fat) and daily treatment with or without aPKC inhibitor (ACPD or 1H-imidazole-4-carboxamide, 5-amino-1-[2,3-dihydroxy-4-[(phosphono-oxy)methyl]cyclopentyl-[1R-(1a,2b,3b,4a) (ICAP)), mice were injected with or without insulin (1 U/kg body weight given intraperitoneally) and killed 15 minutes post insulin injection. Post mortem, liver tissue was removed and examined for immunoreactivity of the indicated signaling factors.

Tissue Preparation: To prepare cell lysates, liver and muscle tissue samples were homogenized in ice-cold buffer containing 0.25 mol/l sucrose, 20 mmol/l Tris/HCl (pH, 7.5), 2 mmol/l EGTA, 2 mmol/l EDTA, 1 mmol/l phenlysulfonlyfluoride (PMSF), 20 µg/ml leupeptin, 10 µg/ml aprotinin, 2 mmol/l Na4P2O7, 2 mmol/l Na3VO4, 2 mmol/l NaF, and 1 µmol/l microcystin, and then supplemented with 1% TritonX-100, 0.6% Nonidet and 150 mmol/l NaCl, and cleared by low-speed centrifugation.

Western Analysis: Western analysis for the indicated signaling factors and GAPDH (endogenous control) were conducted as described in Sajan and Farese. 2012 Diabetologia. 55:1446-1457, Standaert et al. 2004. J. Biol. Chem. 279:24929-24934, Sajan et al. 2012. Metabolism. 61:459-469, Sajan et al. 2009. Diabetologia. 52:1197-1207, Sajan et al. 2009. J. Lipid Res. 50:1133-1145, and Sajan et al. 2013. Diabetologia. 56:2507-2516 using rapid anti-phospho-Ser$^{473}$-Akt antiserum, rabbit anti-glyceraldehyde-phosphate dehydrogenase (GAPDH) antiserum, rabbit anti-WD40-ProF antiserum, and rabbit anti-aPKC antiserum (Santa Cruz Biotechnologies, Santa Cruz, Calif.); rabbit anti-phospho-Thr560/555 PKC-ζ/λ/ι antiserum (Invitrogen, Carlsbad, Calif.); rabbit anti-p-Ser$^{256}$-FoxO1 and anit-FoxO1 antiserum (Abnova, Walnut, Calif.); mouse monoclonal anti-PKC-λ/ι antibodies (Transduction Antibodies, Bedford, Mass.); and rabbit anti-phospho-Ser$^9$-GSK3β antiserum, rabbit anti-phosphoSer$^{2248}$-mTOR antiserum, and mouse anti-Akt antibodies (Cell Signaling Technologies, Danvers, Mass.). Samples from experimental groups were compared on the same blots and corrected for recovery as needed by measurement of GAPDH immunoreactivity.

Data are expressed as mean±SEM, and P values were determined by one-way ANOVA and least-significant multiple comparison methods.

Results

FIGS. 7A-7D demonstrate the effects of HFF diet and ICAP (I) or ACPD (A) on hepatic resting/basal and insulin stimulated phosphorylation of Ser$^{473}$-Akt (FIG. 7A), Ser9-GSK3β (FIG. 7B), Thr$^{555/560}$-PKC-λ/ζ (FIG. 7C), and Thr$^{2448}$-mTOR (FIG. 7D). In control low-fat-fed mice, insulin provoked rapid increases in the activity of both aPKC (FIG. 7C) and Akt2 (FIG. 7A) in the liver. In HFF mice, basal/resting and insulin-stimulated activities of aPKC (FIG. 7C) and Akt2 (FIG. 7A) were elevated. This is possibly due to hyperinsulinemia. Further, in HFF mice basal/resting and insulin-stimulated activities of aPKC (FIG. 7C) and Akt2 (FIG. 7A) were increased after acute insulin treatment to levels comparable with those of low fat fed mice.

ACPD and ICAP reduced basal/resting and exogenous insulin-stimulated hepatic aPKC activities to levels observed in control low fat fed mice (FIG. 7C). In contract, ACPD and ICAP treatment did not alter resting Akt2 activity in livers of HFF mice, but increased insulin-stimulated Akt2 activity therein (FIG. 7A).

Example 8

Effect of High Fat Feeding and ICAP or ACPD on Expression and Phosphorylation of Lipogenic and Gluconeogenic Enzymes, Recovery of aPKC, FoxO1, and WD40/ProF in WD40/ProF Immunopercipitates, and Recovery of aPKC and Akt2 Activity in Liver Methods Standard (C57Bl/6/SV129) mice consuming standard low-fat mouse chow were injected subcutaneously (s.c.) with a daily single injection of ICAP (1 mg/kg body weight) or ACPD (10 mg/kg body weight). After 10 weeks of feeding a low fat diet (10% calories from fat) (control mice) or a high fat diet (40% of calories from milk fat) and daily treatment with or without aPKC inhibitor (ACPD or 1H-imidazole-4-carboxamide, 5-amino-1-[2,3-dihydroxy-4-[(phosphono-oxy)methyl]cyclopentyl-[1R-(1a,2b,3b,4a) (ICAP)), mice were injected with or without insulin (1 U/kg body weight given intraperitoneally) and killed 15 minutes post injection. Post mortem, liver tissue was removed and examined for immunoreactivity of the indicated signaling factors.

For the results shown in FIGS. 8A-8D, liver tissue was prepared and mRNA levels of SREVP-1c, FAS, PEPCK, and G6PAse were analyzed as described in Example 4.

For results shown in FIGS. 9A-9D, cell lysates were prepared as described in Example 7. Nuclear preparations were also prepared as described in Sajan et al. 2009. Diabetologia. 52:1197-1207. Western analysis was conducted to evaluate the indicated immunoreactive proteins as in Example 7, except in this Example, rabbit polyclonal anti-GAPDH antiserum, rabbit polyclonal anti-FAS antiserum, rabbit polyclonal anti-PEPCK antiserum, rabbit polyclonal anti-G6Pase antiserum (Santa Cruz Biotechnologies, Santa Cruz, Calif.), and mouse monoclonal anti-SREBP-1 antibodies (Lab Vision Corp., Freemont, Calif.) were used to detect the indicated proteins.

For the results shown in FIG. 10A, liver cell lysates were prepared as previously described. Phosphorylated FoxO1 and un-phosphorylated FoxO1 were analyzed using western blotting as previously described except rabbit anti-phospho-Ser$^{256}$-FoxO1 antisera and anti-FoxO1 antiserum was used.

For the results shown in FIGS. 10B, 10C, and 10D, immunopercipitates were prepared from liver cell lysates that were prepared as previously described using an anit-WD40/ProF antibody. For the results in FIG. 10B, the indicated immunoreactive proteins were analyzed in the immunopercipitates via western blot as previously described except that rabbit anti-aPKC-λ/ι, FoxO1, or WD40/ProF antisera were used. For the results in FIGS. 10O and 10D, activities of Akt2 (FIG. 10C) and aPKC (FIG. 10D) were evaluated in the immunopercipitates as described in Example 3.

Data are expressed as mean±SEM, and P values were determined by one-way ANOVA and least-significant multiple comparison methods.

Results

FIGS. 8A-8D demonstrates the effects of a HFF diet and ICAP (I) or ACPD (A) treatment on mRNA levels of lipogenic enzymes SREBP-1c (FIG. 8A) and FAS (FIG. 8B), as well as mRNA levels of gluconeogenic enzymes PEPCK (FIG. 8C) and G6Pase (FIG. 8D) in the livers of ad libitum-fed mice. As shown in FIGS. 8A-8D, HFF stimulated increases in hepatic mRNA levels of lipogenic enzymes sterol receptor element-binding protein-1c (SREBP-1c) (FIG. 8A) and fatty acid synthase (FAS) (FIG. 8C), as measured in the fed state. HFF also stimulated increases in hepatic mRNA levels of gluconeogenic enzymes PEPCK (FIG. 8B) and glucose-6-phosphatase (G6Pase) (FIG. 8D), as measured in the fed state. The increase in mRNA levels for each enzyme correlated to increases in protein levels as shown in FIGS. 9A-9D.

However, mRNA (FIGS. 8A-8D) and protein (FIGS. 9A-9D) levels of SREPB-1c, FAS, PEPCK, and G6Pase in HFF mice were not significantly different from control/low-fat fed mice after ICAP or ACPD treatment and reduction of hepatic aPKC activity. Consonant with the idea that diminished hepatic aPKC activity was responsible for improvements in expression of lipogenic and gluconeogenic enzymes in HFF mice treated with ICAP or ACPD, aPKC plays a significant role in 1) feeding- and insulin-dependent increases in activity and expression of SREBP-1c, which is implicated in the increase in expression of multiple lipogenic enzymes; and 2) fasting-dependent increases in expression of PEPCK and G6Pase.

In livers of T2DM humans, and rodents, Akt activity/activation is diminished and expression of PEPCK/G6Pase is increased. However, in the HFF mice in this Example, the presence of increased PEPCK/G6Pase expression in the face of elevated hepatic Akt2 activity seemed at odds. This conundrum was resolved by finding that Akt2-dependent phosphorylation of Ser256-FoxO1, which by its phosphorylation and nuclear exclusion mediates insulin-dependent decreases in gluconeogenic enzyme expression, was markedly diminished basally and almost completely unresponsive to exogenous insulin treatment in livers of HFF mice (FIG. 10A).

In contrast to FoxO1 phosphorylation but in keeping with increases in hepatic Akt2 activity in HFF mice, Akt-dependent phosphorylation of both $Ser^9$-glycogensynthase kinase (GSK)-3β, which, by inhibiting GSK3β, mediates stimulatory effects on glycogen synthesis, and $Ser^{2448}$-mTOR, which, by activating S6 kinase, mediates stimulatory effects on lipogenesis, was increased by high fat feeding, as well as by exogenous insulin treatment. Moreover, this was not altered by ICAP or ACPD treatment (FIGS. 7B and 7D, Example 7). Accordingly, the defect in FoxO1 phosphorylation in HFF mice was relatively specific and did not reflect a generalized defect in hepatic Akt-dependent phosphorylation.

Treatment of HFF mice with ICAP or ACPD fully or partially restored basal/resting and insulin-stimulated hepatic FoxO1 phosphorylation (FIG. 10A). This restoration suggested that activation of hepatic aPKC contributed to the impairment of FoxO1 phosphorylation in HFF liver. Moreover, the stimulatory effect of ICAP or ACPD on FoxO1 phosphorylation provided a reasonable explanation for the improvement/suppression of gluconeogenic enzyme expression in HFF mice (FIGS. 8A-8D).

Findings that FoxO1 phosphorylation was diminished despite heightened Akt2 activity, and was increased in basal/resting conditions by ICAP or ACPD without change in overall cellular Akt2 activity, suggested that Akt-dependent FoxO1 phosphorylation and inhibition thereof by HFF-activated aPKC might be compartmentalized. In adipocytes, the scaffold protein WD40/ProF binds FoxO1 and activated forms of both Akt and aPKC and, moreover, is needed for Akt-mediated phosphorylation of FoxO1 but not other Akt substrates, such as GSK3β and mTORC1, i.e., a pattern of selective inhibition of Akt substrates identical to that observed above in HFF liver. Indeed, as shown in FIGS. 10A-10D, liver levels and activity of aPKC recovered in WD40/ProF immunoprecipitates were increased, particularly by HFF and to a lesser degree by exogenous insulin treatment (FIGS. 10B and 10D).

Activity of Akt recovered in WD40/ProF immunoprecipitates was increased by insulin in control/LFF mice (FIG. 10O). Basal/resting and insulin-stimulated activities of Akt associated with WD40/ProF were diminished by HFF (FIG. 10C). Treatment of HFF mice with ICAP or ACPD diminished aPKC binding to WD40/Prof (FIGS. 10B and 10D) but simultaneously increased WD40/ProF-associated Akt activity (FIG. 10O) and total cellular FoxO1 phosphorylation (FIG. 10A), thereby decreasing gluconeogenic enzyme expression (FIGS. 8A-8D).

Example 9

Effect of High Fat Feeding and ICAP or ACPD on Glucose Tolerance, Serum Levels of Glucose, Insulin, Triglycerides, and Cholesterol, Body Weight, Food Intake, Liver Triglycerides, Abdominal Fat Deposits, and Hepatic Fat Methods Standard (C57Bl/6/SV129) mice consuming standard low-fat mouse chow were injected subcutaneously (s.c.) with a daily single injection with or without either ICAP (1 mg/kg body weight) or ACPD (10 mg/kg body weight)). After 9 weeks of treatments, mice were subjected to glucose tolerance testing using methods generally known in the art. Briefly, 2 mg glucose/kg body weight was injected intraperitoneally. After the glucose injection, blood glucose levels were measured at 0, 30, 60, 90 and 120 minutes post-injection. 15 minutes prior to killing, mice were injected with or without insulin (1 U/kg body weight). Serum glucose, triglycerides, and serum cholesterol were measured using methods generally known in the art. Liver triglycerides were also measured using methods generally known in the art. Over the 10 weeks, body weight and food intake were measured weekly. Overall change in bodyweight was also evaluated. Additionally, epididymal plus retroperitoneal fat (also abbreviated PG/PN fat) was measured and evaluated as g/100 g of body weight. After killing, liver tissue samples were sectioned and prepared for Oil red O staining by methods generally known in the art. Samples were Oil Red O stained to observe hepatic fat contents.

Where appropriate, data are expressed as mean±SEM, and P values were determined by one-way ANOVA and least-significant multiple comparison methods.

Results

Treatment with ICAP or ACPD improved glucose tolerance, basal glucose levels in fasting and fed conditions, and acute effects of insulin on serum glucose levels in HFF to levels indistinguishable from those seen in control chow-fed mice (FIGS. 11A-11E). On the other hand, although fasting insulin levels in HFF mice were improved by ICAP or ACPD treatment, serum insulin levels were still modestly elevated (FIG. 11C). It is possible that the remaining hyperinsulinemia in ICAP- and ACPD-treated HFF mice was sufficient to compensate for any residual insulin resistance.

In addition to normalization or near normalization of glucose homeostasis, treatment with ICAP and ACPD largely prevented (a) weight gain without altering food intake (FIGS. 12A, 12B and 12E); (b) increases in liver triglycerides (FIG. 12C) and fat content (FIGS. 13A-D); and (c) increases in serum triglycerides and cholesterol levels (FIGS. 11D and 11E). In addition, HFF-induced increases in abdominal fat depots were improved by ICAP and trended downward with ACPD treatment (FIGS. 12A-12E). Remaining abnormalities in lipid homeostasis may reflect effects of residual hyperinsulinemia on lipid synthesis in adipocytes or remaining small increases in lipogenic enzymes in ICAP- and ACPD-treated HFF mice.

Example 10

Effect of Ceramide on Hepatic aPKC Activity and the Effect of HFF Diet on Hepatic Levels of Ceramide and Sphingomyelin Species Methods Standard (C57Bl/6/SV129) mice consumed a standard low-fat or high-fat diet for 10 weeks. At 10 weeks mice were treated with or without insulin for 15 min prior to killing. Liver cell lysates were prepared as in Example 5 and aPKC activity assay was performed on the aPKC immunoprecipitate as in Example 5, except here the activity assays were carried out in the presence of the indicated concentrations of ceramide. Additionally, the levels of ceramide and sphingomyelin species in lipid extracts prepared from the liver cell lysates. Ceramide and sphingomyelin species were measured by liquid chromatography tandem mass spectrometry analysis of the lipid extracts of the liver lysates.

Where appropriate, data are expressed as mean±SEM, and P values were determined by one-way ANOVA and least-significant multiple comparison methods.

Results

Figures 9A, 9B, 9C, 9D:
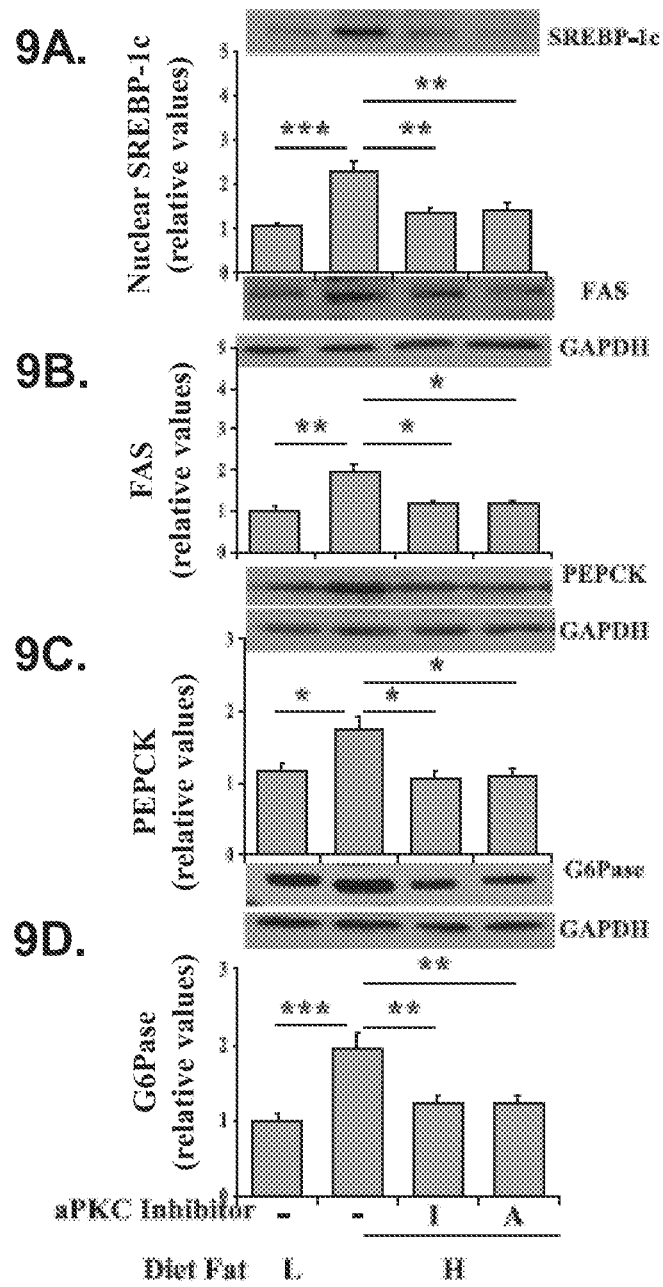

As ceramide provokes hepatic abnormalities in HFF mice and directly activates aPKC it was tested whether ceramide contributed to increases in aPKC activity in the HFF mice. Ceramide strongly activated aPKC when added to immunoprecipitates prepared from liver lysates of LFF/control mice but had only a weak effect on aPKC immunoprecipitated from lysates of HFF mice and diminished activity of aPKC immunoprecipitated from lysates of HFF mice treated acutely with insulin (FIG. 14). (Note: ceramide has biphasic effects on aPKC activity, with inhibition after stimulation in dose response studies) Similarly, PIP3 inhibits aPKC activity when added in excess). On the other hand, acute insulin treatment, possibly acting via PIP3, elicited further increases in aPKC activity in HFF mice (FIG. 14 [compare with FIG. 9A]). Ceramide levels were increased in HFF mice as shown in FIG. 14.

Example 11

Effect of ACPD in Lean or Ob/Ob Mice on Glucose Tolerance and Phosphorylation of aPKC and Akt Methods Male mice, 3-5 months of age, were used throughout these studies. The ob/ob mice and their lean counterparts (ob$^+$) were purchased from Jackson Laboratories (Bar Harbor, Me., USA) at 2-3 months of age and studied over a 10-week period. During the 3rd to 5th month, they were injected subcutaneously once daily with ACPD (10 mg/kg body weight) in physiological saline vehicle or vehicle alone. During the 9th week, glucose tolerance was measured after an overnight fast by intraperitoneal injection of 2 mg glucose per kg body weight, as described in Example 9. At the 10th week, mice were injected with or without insulin (1 U/kg body weight) 15 minutes prior to killing and rapid harvesting of tissues.

All experimental procedures involving animals were approved by the Institutional Animal Care and Use Committees of the University of South Florida College of Medicine, and the James A. Haley Veterans Administration Medical Center Research and Development Committee, Tampa, Fla.

Tissue lysates were prepared and western blotting to detect immunoreactive p-ser473-Akt and p-thr555/560-PKC-ι/λ/ζ was performed as previously described in the Examples herein. Where appropriate, data are expressed as mean±SEM, and P values were determined by one-way ANOVA and least-significant multiple comparison methods.

Results

Figures 16A, 16B, 16C, 16D:
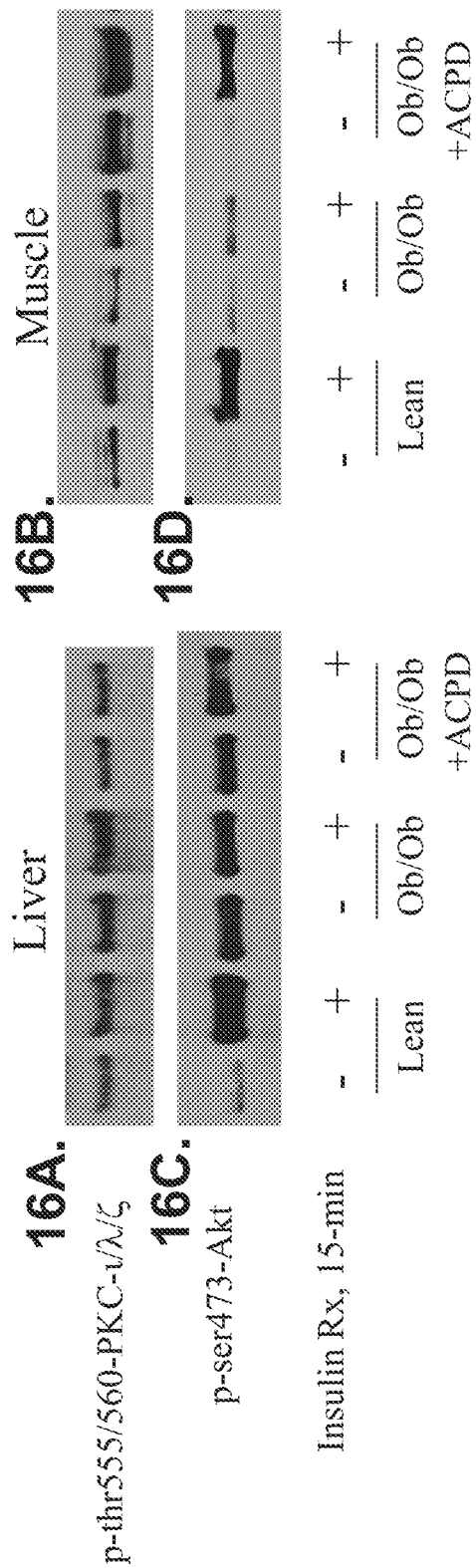

Treatment of ob/ob mice with ACPD (10 mg/kg body weight given once daily subcutaneously for 10 weeks) led to partially decreased phosphorylation of hepatic aPKC in both resting (but stimulated by endogenous hyperinsulinaemia-See Example 12) and exogenous-insulin-stimulated conditions (FIG. 16A). In contrast to aPKC, the increases in Akt phosphorylation observed in livers of ob/ob mice were not altered by ACPD treatment (FIG. 16C). Additionally, the impairment insulin-stimulated phosphorylation of aPKC was improved in muscles of ob/ob mice following ACPD treatment (FIG. 16B), and Akt phosphorylation tended to increase (FIG. 16D).

As seen in FIGS. 17A-17B, although fasting blood glucose levels were only mildly increased in ob/ob mice relative to lean control mice, glucose tolerance, as measured in the peritoneal glucose tolerance test (GTT), was more strikingly diminished. Treatment of ob/ob mice with ACPD led to improvements in both fasting blood glucose levels and GTT-determined glucose tolerance (FIG. 17A). On the other hand, the elevated fasting and post-glucose insulin levels seen in ob/ob mice during the GTT (FIG. 17B), showed little or no change.

Example 12

Effect of ACPD on Food Intake, Body Weight, Fat Deposition, Serum Triglycerides, and Liver Triglycerides in Ob/Ob Mice Methods Male mice, 3-5 months of age, were used throughout these studies. The ob/ob mice and their lean counterparts (ob$^+$) were purchased from Jackson Laboratories (Bar Harbor, Me., USA) at 2-3 months of age and studied over a 10-week period. During the 3rd to 5th month, they were injected subcutaneously once daily with ACPD (10 mg/kg body weight) in physiological saline vehicle or vehicle alone. During the 9th week, glucose tolerance was measured after an overnight fast by intraperitoneal injection of 2 mg glucose per kg body weight, as described in Example 9. At the 10th week, mice were injected with or without insulin (1 U/kg body weight) 15 minutes prior to killing and rapid harvesting of tissues. Body weight and food intake was measured weekly. The combined weight of epididymal plus retroperitoneal fat depots (abdominal fat depots) was measured. Serum and liver triglycerides were obtained and measured as previously described in the Examples herein.

Data are expressed as mean±SEM, and P values were determined by one-way ANOVA and least-significant multiple comparison methods.

All experimental procedures involving animals were approved by the Institutional Animal Care and Use Committees of the University of South Florida College of Medicine, and the James A. Haley Veterans Administration Medical Center Research and Development Committee, Tampa, Fla.

Results

Figures 18A, 18B, 18C, 18D, 18E:
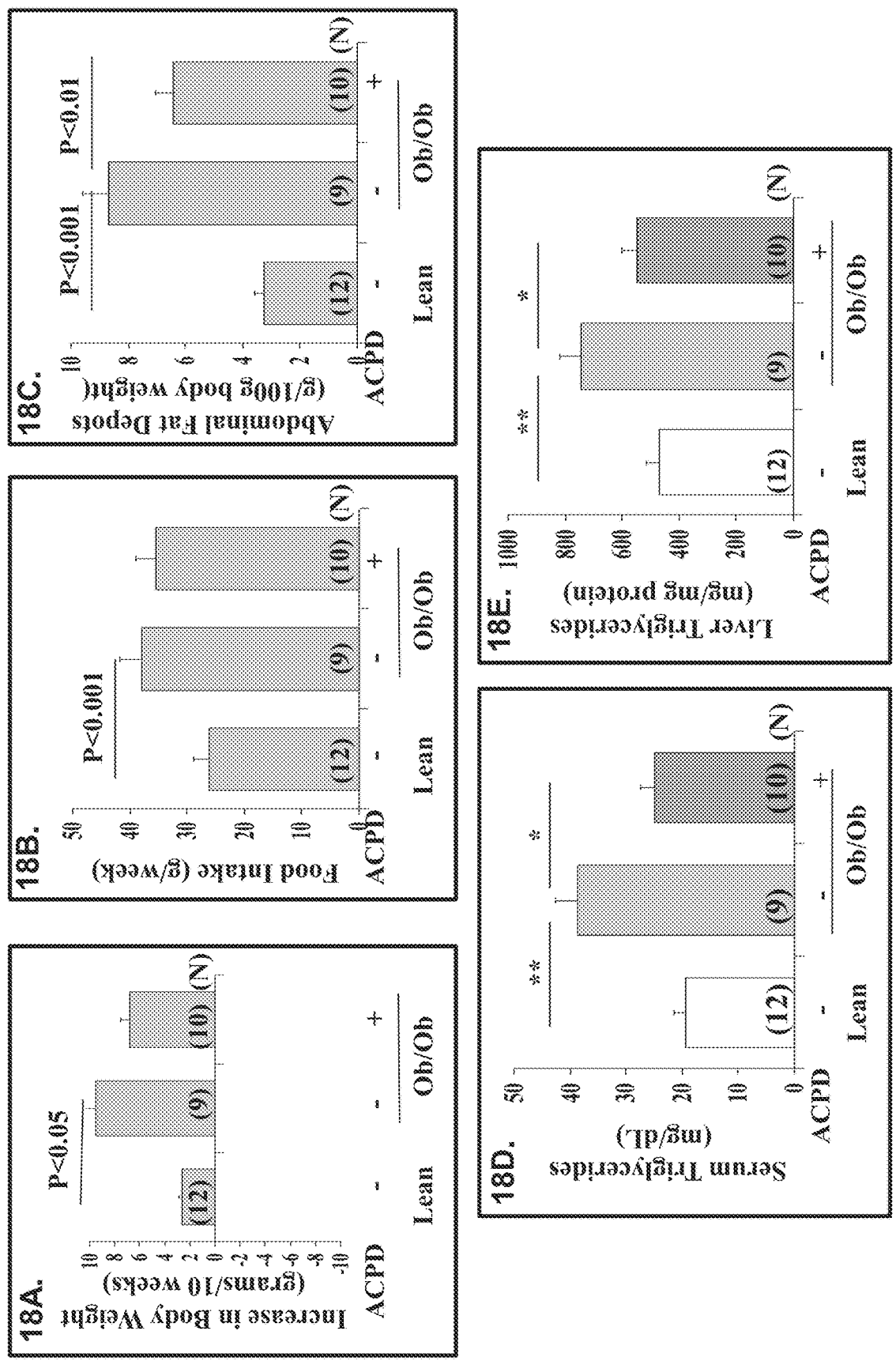

Food intake was increased in ob/ob mice and ACPD treatment had little or no effect on food intake as shown in FIG. 18B. On the other hand, increases in body weight during the 10-wek study period trended downward in ob/ob mice treated with ACPD (FIG. 18A). Further, in ob/ob mice, the combined weights of epididymal plus retroperitoneal fat depots (FIG. 18C), serum triglycerides (FIG. 18D), and liver triglycerides (FIG. 18E) diminished following ACPD treatment.

Example 13

Effects of ACPD on Phosphorylation/Activities of pSer$^{473}$-Akt and p-Thr$^{556/560}$-PKC-λ/ζ in Resting/Basal and Insulin-Stimulated Conditions and During Treatment with aPKC Inhibitor in Liver and Muscle Lysates of Lean Ob$^+$ and Obese-Phase Ob/Ob Mice Methods Male mice, 3-5 months of age, were used throughout these studies. The ob/ob mice and their lean counterparts (ob+) were purchased from Jackson Laboratories (Bar Harbor, Me., USA) at 2-3 months of age and studied over a 10-week period. During the 3rd to 5th month, they were injected subcutaneously once daily with ACPD (10 mg/kg body weight) in physiological saline vehicle or vehicle alone. During the 9th week, glucose tolerance was measured after an overnight fast by intraperitoneal injection of 2 mg glucose per kg body weight, as described in Example 9. At the 10th week, mice were injected with or without insulin (1 U/kg body weight) 15 minutes prior to killing and rapid harvesting of tissues. Body weight and food intake was measured weekly. ACPD in all of the Examples disclosed herein does not inhibit kinases, Akt2, FGFR1/2/3/4, mTOR, GSK3β, IRAK1/4, JAK1/2, MEK1, ERK1/2, JNK 1/2, PKA, Src, ROCK 2, ROS1, or PI3Kα/α as tested by Life Technologies (Madison Wis., USA)

Liver and muscle cell lysates were prepared as described as in Example 5. Western analyses were conducted as described in these Example 7 except using: rabbit polyclonal anti-phospho-serine-473-Akt, anti-glyceraldehyde-phosphate dehydrogenase (GAPDH), anti-WD40/ProF, anti-aPKC antisera, anti-FAS, ant-G6Pase, anti-PEPCK, anti-p65/RelA/NFκB antisera (Santa Cruz Biotechnologies, Santa Cruz, Calif., USA); rabbit polyclonal anti-phospho-threonine-560/555-PKC-ζ/ι/λ antiserum (Invitrogen, Carlsbad, Calif., USA); rabbit polyclonal anti-p-serine-256-FoxO1 and anti-FoxO1 antisera (Abnova, Walnut, Calif., USA); mouse monoclonal anti-PKC-λ/ι antibodies (Transduction Antibodies, Bedford, Mass., USA); rabbit polyclonal anti-phospho-serine-9-GSK3β, anti-ACC and anti-phospho-serine-2248-mTOR antisera, and mouse monoclonal anti-Akt antibodies (Cell Signaling Technologies, Danvers, Mass., USA); mouse monoclonal anti-SREBP-1 antibodies (Lab Vision Corp., Freemont, Calif., USA); horseradish-peroxidase-conjugated goat anti-mouse and anti-rabbit secondary antibodies (Biorad, Hercules, Calif., USA); and horseradish-peroxidase-conjugated AffiniPure donkey anti-mouse and anti-rabbit secondary antibodies (Jackson ImmunoResearch Labs, West Grove, Pa., USA). Samples from experimental groups were compared on the same blots and routinely checked with loading controls.

Data are expressed as mean±SEM, and P values were determined by one-way ANOVA and least-significant multiple comparison methods.

Results

Figure 19A:
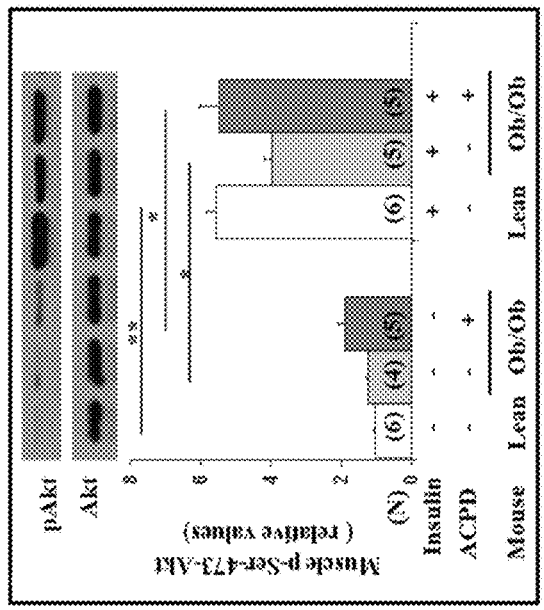

Results are shown in FIGS. 19A-19 D. In lean control ob$^+$ mice, insulin increased phosphorylation of both aPKC and Akt in liver and muscle (FIGS. 19A, 19B, 19C, 19D). However, in muscles of ob/ob mice, resting/basal and insulin-stimulated increases in phosphorylation of aPKC were significantly diminished. Insulin-stimulated Akt phosphorylation trended downward, relative to findings in lean ob$^+$ mice (FIGS. 19B and 19D).

In contrast to muscle, phosphorylation of hepatic aPKC in ob/ob mice was increased in resting/basal conditions to a level comparable to if not greater than that seen with insulin treatment in lean ob$^+$ mice, and acute exogenous insulin treatment had no further effect on aPKC phosphorylation (FIG. 19C), suggesting that hepatic aPKC was maximally activated in obese-phase ob/ob mice by endogenous hyperinsulinemia (see below) and/or other factors. Partly similar to hepatic aPKC, resting/basal hepatic Akt phosphorylation was elevated in ob/ob mice, and with acute exogenous insulin treatment, Akt phosphorylation was elevated to levels not significantly different from those seen in lean ob$^+$ mice (FIG. 19A).

Figure 19B:
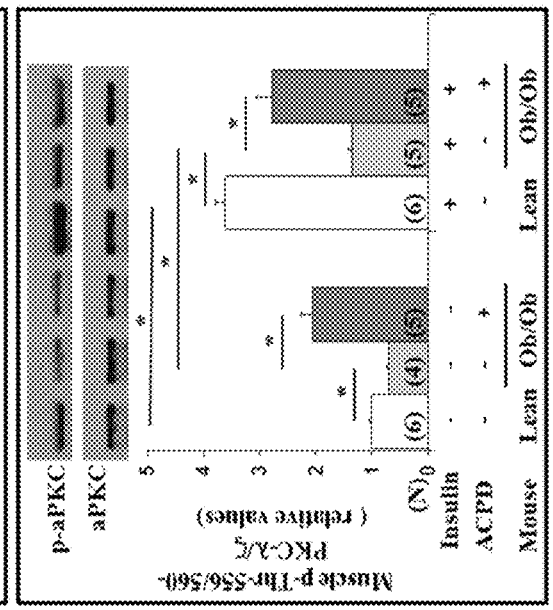
Figure 19C:
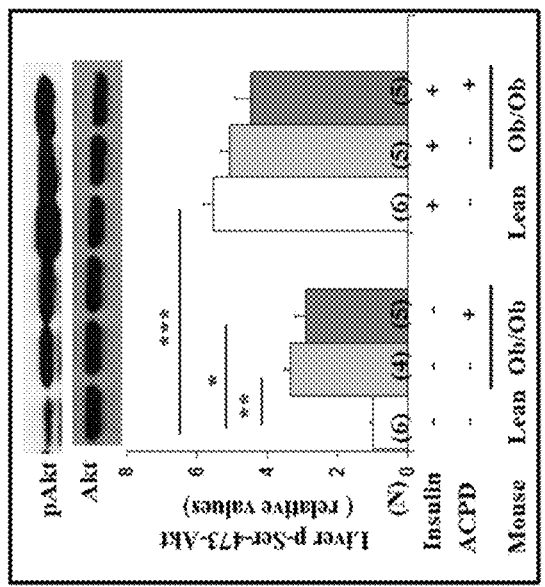
Figure 19D:
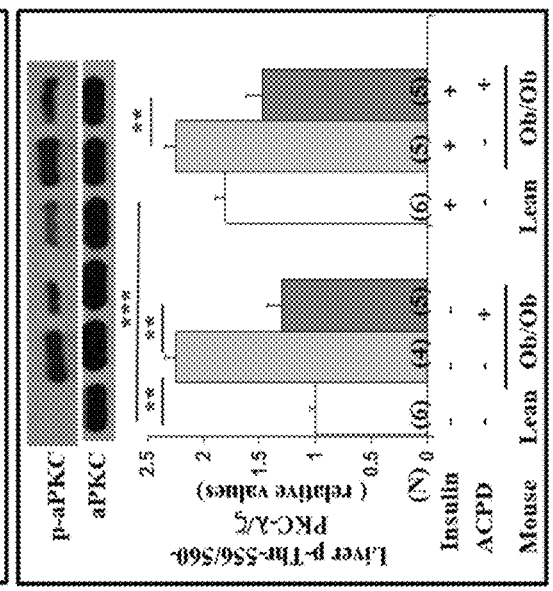

Treatment of ob/ob mice with ACPD reduced the elevated resting/basal levels of hepatic aPKC phosphorylation almost to normal and substantially diminished stimulatory effects of exogenous insulin treatment on hepatic aPKC phosphorylation (FIG. 19C). In contrast to aPKC, hepatic Akt phosphorylation in ob/ob mice was not altered significantly by ACPD treatment (FIG. 19A). Impairments in insulin-stimulated phosphorylation of both aPKC and Akt in muscles of ob/ob mice were significantly improved or trended upward with ACPD treatment (FIGS. 19B and 19D).

Example 14

Phosphorylation of Akt Substrates and Association of aPKC with Hepatic WD40/Prof in Resting/Basal and Insulin-Stimulated Conditions, and During Treatment with aPKC Inhibitor, ACPD, in Livers of Lean Ob$^+$ and Obese-Phase Ob/Ob Mice Methods Male mice, 3-5 months of age, were used throughout these studies. The ob/ob mice and their lean counterparts (ob+) were purchased from Jackson Laboratories (Bar Harbor, Me., USA) at 2-3 months of age and studied over a 10-week period. During the 3rd to 5th month, they were injected subcutaneously once daily with ACPD (10 mg/kg body weight) in physiological saline vehicle or vehicle alone. During the 9th week, glucose tolerance was measured after an overnight fast by intraperitoneal injection of 2 mg glucose per kg body weight, as described in Example 9. At the 10th week, mice were injected with or without insulin (1 U/kg body weight) 15 minutes prior to killing and rapid harvesting of tissues. Body weight and food intake was measured weekly. ACPD in all of the examples disclosed herein does not inhibit kinases, Akt2, FGFR1/2/3/4, mTor, GSK3β, IRAK1/4, JAK1/2, MEK1, ERK1/2, JNK 1/2, PKA, Src, ROCK 2, ROS1, or PI3Kα/α as tested by Life Technologies (Madison Wis., USA)

Liver cell lysates were prepared as described as in Example 5. Western analyses were conducted as described in Example 7 except using: rabbit polyclonal anti-phospho-serine-473-Akt, anti-glyceraldehyde-phosphate dehydrogenase (GAPDH), anti-WD40/ProF, anti-aPKC antisera, anti-FAS, ant-G6Pase, anti-PEPCK, anti-p65/RelA/NFκB antisera (Santa Cruz Biotechnologies, Santa Cruz, Calif., USA); rabbit polyclonal anti-phospho-threonine-560/555-PKC-ζ/ι-λ antiserum (Invitrogen, Carlsbad, Calif., USA); rabbit polyclonal anti-p-serine-256-FoxO1 and anti-FoxO1 antisera (Abnova, Walnut, Calif., USA); mouse monoclonal anti-PKC-λ/ι antibodies (Transduction Antibodies, Bedford, Mass., USA); rabbit polyclonal anti-phospho-serine-9-GSK3β, anti-ACC and anti-phospho-serine-2248-mTOR antisera, and mouse monoclonal anti-Akt antibodies (Cell Signaling Technologies, Danvers, Mass., USA); mouse monoclonal anti-SREBP-1 antibodies (Lab Vision Corp., Freemont, Calif., USA); horseradish-peroxidase-conjugated goat anti-mouse and anti-rabbit secondary antibodies (Biorad, Hercules, Calif., USA); and horseradish-peroxidase-conjugated AffiniPure donkey anti-mouse and anti-rabbit secondary antibodies (Jackson ImmunoResearch Labs, West Grove, Pa., USA). Samples from experimental groups were compared on the same blots, and routinely checked with loading controls.

To determine association of aPKC and Akt, aPKC and Akt immunoreactive protein was evaluated in WD40/ProF immunopercipitates as previously described in Example 8.

Data are expressed as mean±SEM, and P values were determined by one-way ANOVA and least-significant multiple comparison methods.

Results

In lean $ob^+$ mice, in conjunction with increases in Akt phosphorylation, insulin increased hepatic FoxO1 phosphorylation (FIG. 20A). In ob/ob mice, however, despite hyperinsulinemia and elevated levels of hepatic Akt phosphorylation in resting/basal and insulin-stimulated conditions, FoxO1 phosphorylation remained at a lower or modestly diminished resting/basal level, and, moreover, responded poorly if at all to acute insulin treatment (FIG. 20A). Yet, with ACPD treatment of ob/ob mice, both resting/basal and insulin-stimulated FoxO1 phosphorylation increased to levels comparable to those seen in insulin-stimulated lean $ob^+$ mice (FIG. 20A).

In contrast to FoxO1, phosphorylation of both mTOR and GSK3β was increased, not only by insulin in lean $ob^+$ mice, but also in resting/basal conditions (presumably this reflects hyperinsulinemia and increased Akt activation), and following exogenous insulin treatment in ob/ob mice (FIGS. 20B and 20C). Moreover, ACPD treatment did not substantially alter the elevations in mTOR and GSK3β phosphorylation seen in ob/ob mice (FIGS. 20B and 20C).

Insulin acutely increased recovery of aPKC and Akt in WD40/ProF immunoprecipitates (FIGS. 20D and 20E). However, in ob/ob mice the resting/basal level of aPKC associated with WD40/ProF was increased maximally, as it did not increase further with insulin treatment (FIG. 20D). In contrast, Akt associated with WD40/ProF was diminished basally and increased poorly following insulin treatment (FIG. 20E). Further, ACPD treatment diminished aPKC association with WD40/ProF (FIG. 20D). This was accompanied by increased association of Akt with WD40/ProF (FIG. 20E).

Example 15

Effects of ACPD on mRNA Levels of Hepatic SREBP-1c, FAS, ACC, TNF-α, PEPCK, G6PASE, Hepatic Nuclear Levels of the Proteolytic Fragment of SREBP-1c and Active Subunit of NFκB, and Hepatic Lysate Protein Level of FAS, ACC, PEPCK and G6Pase in Ob/Ob Mice Methods Male mice, 3-5 months of age, were used throughout these studies. The ob/ob mice and their lean counterparts (ob+) were purchased from Jackson Laboratories (Bar Harbor, Me., USA), at 2-3 months of age and studied over a 10-week period. During the 3rd to 5th month, they were injected subcutaneously once daily with ACPD (10 mg/kg body weight) in physiological saline vehicle or vehicle alone. During the 9th week, glucose tolerance was measured after an overnight fast by intraperitoneal injection of 2 mg glucose per kg body weight, as described in Example 9. At the 10th week, mice were injected with or without insulin (1 U/kg body weight) 15 minutes prior to killing and rapid harvesting of tissues.

mRNA Quantification. Tissues and RNA was prepared as described in Example 4. Quantification of mRNA was performed using quantitative PCR as described in Example 4. Primers, in addition to those used in Example 4 are as follows: TNF-α Forward SEQ ID NO: 11 ACGGCATG-GATCTCAAAGAC, TNF-α Reverse SEQ ID NO: 12 AGA-TAGCAAATCGGCTGACG ACC Forward SEQ ID NO: 13 GACTTCATGAATTTGCTGAT and ACC Reverse SEQ ID NO 14: AAGCTGAAAGCTTTCTGTCT.

Nuclear preparations were prepared as previously described in Example 6. Western analysis was performed as described in Example 14.

Data are expressed as mean±SEM, and P values were determined by one-way ANOVA and least-significant multiple comparison methods.

Results

Results are shown in FIGS. 21A-21F, 22, and 23A-23D. In ob/ob mice, hepatic expression of gluconeogenic enzymes, PEPCK (FIG. 21E) and G6Pase (FIG. 21F), lipogenic enzymes, SREBP-1c (FIG. 21A), FAS (FIG. 21B) and ACC (FIG. 21C), and proinflammatory tumor necrosis factor-α (TNF-α) (FIG. 21D) was elevated, but virtually restored to normal with ACPD treatment (FIG. 21A-F). Similarly, in ob/ob mice, nuclear protein levels of the active fragment of SREBP-1c and nuclear protein levels of the active p65/RelA subunit of NFκB were increased (FIG. 22), and lysate protein levels of ACC (FIG. 23A), FAS (FIG. 23B), PEPCK (FIG. 23C) and G6Pase (FIG. 23D) were increased, and ACPD treatment largely reversed these increases (FIGS. 23A-23D).

Example 16

Effect of Insulin Stimulation on aPKC and Akt2 Activity in the Brains of High Fat Fed and Ob/Ob Mice Introduction Insulin-resistant and (glucose intolerant) syndromes, including obesity and metabolic syndrome, and Alzheimer's disease (AD) are endemic closely related disorders. Insulin resistance predisposes a subject to AD development. In Western/Westernized populations, insulin-resistant obesity and the metabolic syndrome (O/MetSYN) are present in 34% of the adult population, and frequently progress to type 2 diabetes mellitus (T2DM), which is present in 27% of people over the age of 65 (CDC data, 2011). Moreover, Alzheimer's disease (AD) is estimated to afflict 13% of people over the age of 65 and 45% of people over the age of 85. Furthermore, AD is 50% more prevalent in T2DM, and T2DM prevalence is approximately 2-fold greater in AD. As O/MetSyn/T2DM generally precedes AD, it is suspected that O/MetSyn/T2DM predisposes to the development of AD.

In this Example, the effect of insulin stimulation on aPKC and Akt2 activity in the brains of high fat fed (HFF) and ob/ob mice was evaluated. HFF and ob/ob mice are insulin-resistant, hyperinsulinemic, and develop obesity, metabolic syndrome, and T2DM. Thus, these mice are a model of a subject predisposed to AD.

Methods

Standard lab mice were fed a high fat diet in which 40% of calories were derived from milk fat or a standard chow containing 10% fat ("control" or "con" mice) for 10 weeks. Standard lab mice ("control" or "con") and ob/ob (OB) mice were fed the standard chow containing 10% fat. At 10 weeks some mice in each group were administered 1 U/kg insulin intraperitoneally 15 minutes prior to killing. Brain tissue was removed. Preparations containing brain proteins from the brain tissue samples was analyzed for aPKC and Akt activities via Western Blot followed by quantitative scanning of the blots.

Results

Results from this experiment are demonstrated in FIGS. 25A-25D. Treatment of control mice intraperiotneally with a maximal dose of insulin leads to increases in brain activities and phosphorylation of both Akt (FIGS. 25B and 25D) and aPKC (FIGS. 25A and 25C). It has been demonstrated, Akt and aPKC are activated in parallel by the product of phosphatidylinositol 3-kinase (PI3K) and phosphatidytlinositol-3, 4, 5-$(PO_4)_3$ ($PIP_3$) during insulin action. Together, these mediate most metabolic actions of insulin in other tissues as well. However, as demonstrated in this Example, the basal/resting activities of both Akt and aPKC were elevated in HFF and ob/ob mice. Moreover, there was little or no further response of these proteins in response to exogenous insulin treatment (FIGS. 25A-25D). This suggests that the hyperinsulinemia present in the HFF and ob/ob mice had maximally activated both Akt and aPKC, even in basal/resting conditions.

Example 17

Effect of Insulin Stimulation on Phosphorylation of the Akt Substrates FoxO1, FoxO3a, GSK3β, and mTOR Introduction Insulin-resistant and (glucose intolerant) syndromes, including obesity and metabolic syndrome, and Alzheimer's disease (AD) are endemic closely related disorders. Insulin resistance predisposes a subject to AD development. In Western/Westernized populations, insulin-resistant obesity and the metabolic syndrome (O/MetSYN) are present in 34% of the adult population, and frequently progress to type 2 diabetes mellitus (T2DM), which is present in 27% of people over the age of 65 (CDC data, 2011). Moreover, Alzheimer's disease (AD) is estimated to afflict 13% of people over the age of 65 and 45% of people over the age of 85. Furthermore, AD is 50% more prevalent in T2DM, and T2DM prevalence is approximately 2-fold greater in AD. As O/MetSyn/T2DM generally precedes AD, it is suspected that O/MetSyn/T2DM predisposes to the development of AD.

In this Example, the effect of insulin stimulation on the phosphorylation of Akt substrates FoxO1, FoxO3a, GSK3β, and mTOR in the brains of high fat fed (HFF) and ob/ob mice was evaluated. The HFF and ob/ob mice are insulin-resistant, hyperinsulinemic, and develop obesity, metabolic syndrome, and T2DM. Thus, these mice are a model of a subject predisposed to AD.

Methods

Standard lab mice were fed a high fat diet in which 40% of calories were derived from milk fat or a standard chow containing 10% fat ("control" or "con" mice) for 10 weeks. Standard lab mice ("control" or "con") and ob/ob (OB) mice were fed the standard chow containing 10% fat. At 10 weeks some mice in each group were administered 1 U/kg insulin intraperitoneally 15 minutes prior to killing. Brain tissue was removed. Preparations containing brain proteins from the brain tissue samples was analyzed for aPKC and Akt activities via Western Blot using phospho-peptide-specific antisera followed by quantitative scanning of the blots.

Results

The results from this experiment are demonstrated in FIGS. 26A-26D and FIGS. 27A-27D. Phosphorylation of the four substrates evaluated was elevated in the basal/resting state of HFF and ob/ob mice (FIGS. 26A-26D and FIGS. 27A-27D) at levels comparable to those achieved by maximal insulin treatment of control mice (FIGS. 25A-25D). Moreover, there was little or no further phosphorylation of these proteins in response to exogenous insulin treatment (FIGS. 26A-26D and FIGS. 27A-27D). This suggests that the hyperinsulinemia present in the HFF and ob/ob mice had maximally activated both Akt and aPKC, even in basal/resting conditions.

Example 18

Effect of ICAPP on aPKC Activity in the Brains of Control and Heterozygous Muscle-Specific PKC-λ Knockout Mice Introduction Insulin-resistant and (glucose intolerant) syndromes, including obesity and metabolic syndrome, and Alzheimer's disease (AD) are endemic closely related disorders. Insulin resistance predisposes a subject to AD development. In Western/Westernized populations, insulin-resistant obesity and the metabolic syndrome (O/MetSYN) are present in 34% of the adult population, and frequently progress to type 2 diabetes mellitus (T2DM), which is present in 27% of people over the age of 65 (CDC data, 2011). Moreover, Alzheimer's disease (AD) is estimated to afflict 13% of people over the age of 65 and 45% of people over the age of 85. Furthermore, AD is 50% more prevalent in T2DM, and T2DM prevalence is approximately 2-fold greater in AD. As O/MetSyn/T2DM generally precedes AD, it is suspected that O/MetSyn/T2DM predisposes to the development of AD.

In this Example, the effect of ICAPP on aPKC activity in the brains of control and heterozygous muscle-specific PKC-λ knockout mice was evaluated. The heterozygous knockout mice are another model of systemic insulin resistance that stems from a specific defect in glucose transport in the skeletal muscle of these mice. This defect, via hyperinsulinemia, activates hepatic aPKC and causes activation of gluconeogenesic and lipogenesic pathways. (See also FIG. 24). This leads to obesity, metabolic syndrome, and type 2 diabetes. Thus, these mice are a model of a subject predisposed to AD.

Methods

Standard lab mice ("control" or "con" mice) and heterozygous muscle-specific PKC-λ knockout mice were fed standard chow containing 10% fat. Some mice were treated for 8 days with ICAPP. Some mice were acutely treated with insulin (1 U/kg body weight administered intraperitoneally) 15 minutes prior to killing. Brain tissues were collected and prepared for phospho-protein analysis. Activity/activation of aPKC was assessed by Western blot analyses of phospho-protein immunoreactivity followed by quantitative scanning of the blots.

Results

The results from this experiment are demonstrated in FIG. 28. In this model, aPKC activity in the brain was decreased. It is not believed that ICAPP itself crosses the blood brain barrier. Thus, these results suggest that improvement in hepatic aPKC in these knockout mice and the subsequent restoration of relatively normal hepatic gluconeogenesis and overall glucose homeostasis can influence aPKC activity in the brain.

We claim:

1. A method of reducing weight gain in a subject in need thereof, the method comprising:
   administering an effective amount of 2-acetylcyclopentane-1,3-dione (ACPD) to the subject in need thereof, wherein the subject in need thereof has insulin resistance.

2. The method of claim 1, wherein the effective amount ranges from about 0.001 mg to about 1,000 mg.

3. The method of claim 1, wherein the effective amount ranges from about 1 mg/kg bodyweight to about 20 mg/kg body weight.

4. The method of claim 1, wherein the effective amount is about 10 mg/kg bodyweight.

5. The method of claim 1, wherein the effective amount is administered in a dosage form formulated for oral, vaginal, intravenous, transdermal, subcutaneous, intraperitoneal, or intramuscular administration.

6. The method of claim 1, wherein the effective amount reduces weight gain in the subject in need thereof by about 1% to about 50%.

7. The method of claim 1, wherein the effective amount reduces weight gain in the subject in need thereof by about 25% to about 50%.

8. The method of claim 1, wherein the effective amount reduces weight gain in the subject in need thereof by about 50%.

9. The method of claim 1, wherein the reduction in weight gain is not the result of decreased food intake by the subject in need thereof.

* * * * *